(12) United States Patent
Budge et al.

(10) Patent No.: US 10,655,111 B2
(45) Date of Patent: May 19, 2020

(54) MODULATION OF LIPID METABOLISM FOR PROTEIN PRODUCTION

(71) Applicant: LONZA LTD, Visp (CH)

(72) Inventors: James Budge, Canterbury (GB); Christopher Mark Smales, Canterbury (GB); Tanya Jeane Knight, Kent (GB); Robert Young, Berkshire (GB)

(73) Assignee: LONZA LTD., Visp (CH)

( * ) Notice: Subject to any disclaimer, the term of this patent is extended or adjusted under 35 U.S.C. 154(b) by 0 days.

(21) Appl. No.: 15/585,570

(22) Filed: May 3, 2017

(65) Prior Publication Data

US 2017/0321194 A1   Nov. 9, 2017

Related U.S. Application Data

(60) Provisional application No. 62/330,973, filed on May 3, 2016.

(51) Int. Cl.
| | |
|---|---|
| *C07K 16/00* | (2006.01) |
| *C12N 9/02* | (2006.01) |
| *C12P 21/02* | (2006.01) |
| *C07K 14/47* | (2006.01) |
| *C12N 5/071* | (2010.01) |

(52) U.S. Cl.
CPC ........ *C12N 9/0097* (2013.01); *C07K 14/4702* (2013.01); *C07K 16/00* (2013.01); *C12N 5/0682* (2013.01); *C12N 9/0071* (2013.01); *C12N 9/0083* (2013.01); *C12P 21/02* (2013.01); *C12Y 114/19001* (2013.01); *C07K 2317/14* (2013.01)

(58) Field of Classification Search
CPC ................ C12N 9/0097; C12N 5/0682; C12Y 114/19001; C07K 14/4702; C07K 16/10
See application file for complete search history.

(56) References Cited

U.S. PATENT DOCUMENTS

| | | | |
|---|---|---|---|
| 5,633,162 A | 5/1997 | Keen et al. | |
| 6,326,193 B1 | 12/2001 | Liu et al. | |
| 6,703,199 B1 | 3/2004 | Koide | |

FOREIGN PATENT DOCUMENTS

| | | |
|---|---|---|
| WO | 0129058 A1 | 4/2001 |
| WO | 0196584 A2 | 12/2001 |
| WO | 2002095008 A2 | 11/2002 |
| WO | 2004111194 A2 | 12/2004 |
| WO | 2005100573 A2 | 10/2005 |
| WO | 2009062789 A1 | 5/2009 |
| WO | 2017191165 A1 | 11/2017 |

OTHER PUBLICATIONS

Nakakuki et al. 2007; A transcription factor of lipid synthesis, sterol regulatory element binding protein (SREBP)-1a causes G1 cell cycle arrest after accumulation of cyclin-dependent kinase (cdk) inhibitors. FEBS J. 274: 4440-4452.*
Xu et al. (2011; Cloning and sequence analysis of SREBP-1 gene of Xinong saanen dairy goats.) EMBL: AEX31645.1. Alignment with SEQ ID No. 1.*
Xu et al. (2011; Cloning and sequence analysis of SREBP-1 gene of Xinong saanen dairy goats). Accession JN90254.1. Alignment with SEQ ID No. 2.*
Li et al. 2015; Fatty acid synthase promoter: Characterization, and transcriptional regulation by sterol regulatory element binding protein-1 in goat mammary epithelial cells. Gene. 561: 157-164.*
Brown et al. "The SREBP Pathway: Regulation of Cholesterol Metabolism by Proteolysis of a Membrane-Bound Transcription Factor" Cell (1997) vol. 89, pp. 331-340.
Carvell et al. "On-line measurements and control of viable cell destiny in cell culture manufacturing processes using radio-frequency impedance" Cytotechnology (2006) vol. 50, pp. 35-48.
Hagen et al. "An allostatic control of membrane lipid composition by SREBP1" REBS Letters (2010) vol. 584, pp. 2689-2698.
Hua et al. "Sterol Resistance in CHO Cells Traced to Point Mutation in SREBP Cleavage-Activating Protein" Cell (1996) vol. 87, pp. 415-426.
International Search Report and Written Opinion for International Application No. PCT/EP2017/060484 dated Aug. 9, 2017.
Kim et al. "Glycosylation pattern of humanized IgG-like bispecific antibody produced by recombinant CHO cells" Appl. Microbiol. Biotechnol. (2010) vol. 85, pp. 535-542.
Leader et al. "Protein therapeutics: a summary and pharmacological classification" Nature Reviews Drug Discovery (2008) vol. 7, pp. 21-39.
Nianjidsuren et al. "The transcription factor Ap-1 regulates monkey 20alpha-hydroxysteroid dehydrogenase promoter activity in CHO cells" BMC Biotechnology (2014) vol. 14, No. 71, pp. 1-11.
Walsh et al. "Biopharmaceutical benchmarks 2014" Nature Biotechnology (2014) vol. 32, No. 10, pp. 992-1000.
Wu et al. "Overexpression of stearoyl-CoA desaturase-1 results in an increase of conjugated linoleic acid (CLA) and n-7 fatty acides in 293 cells" Biochemical and Biophysical Research Communications (2010) vol. 398, pp. 473-476.
Xu et al. "Overexpression of SREBP1 (sterol regulatory element binding protein 1) promotes de novo fatty acid synthesis and triacylglycerol accumulation in goat mammary epithelial cells" J. Dairy Sci. (2016) vol. 99, No. 1, pp. 783-795.

(Continued)

*Primary Examiner* — Karen Cochrane Carlson
(74) *Attorney, Agent, or Firm* — Lucas & Mercanti, LLP

(57) ABSTRACT

The present disclosure features methods and compositions for modulating lipid metabolism to achieve improved production and quality of recombinant products, such as next generation biologics. Modulation of lipid metabolism as described herein includes, for example, introducing a lipid metabolism modulator described herein to a cell or a cell-free system. Also encompassed by the present disclosure are engineered cells with improved production capacity and improved product quality, methods for engineering such cells, and preparations and mixtures comprising the products from such cells.

7 Claims, 18 Drawing Sheets

Specification includes a Sequence Listing.

(56) References Cited

OTHER PUBLICATIONS

Yokoyama et al. "SREBP-1, as Basic-Helix-Loop-Helix-Leucine Zipper Protein That Controls Transcription of the Low Density Lipoprotein Receptor Gene" Cell (1993) vol. 75, pp. 187-197.
Zhang et al. "Recombinase-Mediated Cassette Exchange (RMCE) for Monoclonal Antibody Expression in the Commercially Relevant CHOK1SV Cell Line" Biotechnol. Prog. (2015) vol. 31, No. 6, pp. 1645-1655.

* cited by examiner

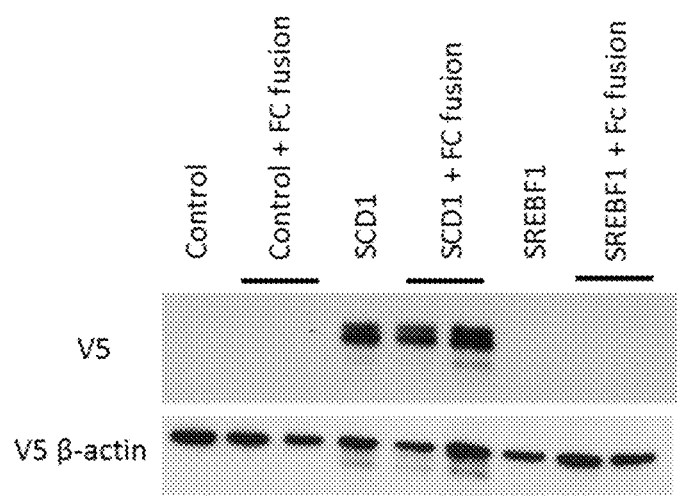
FIG. 3A
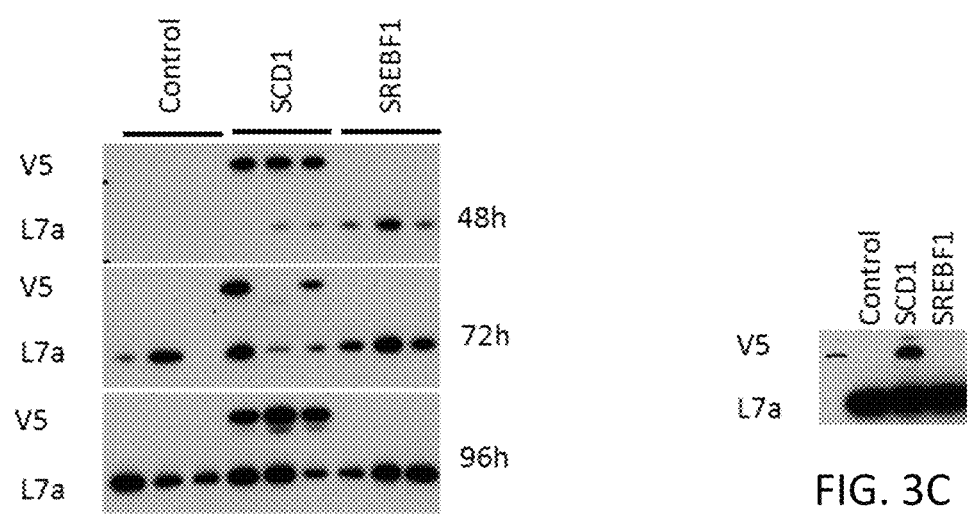
FIG. 3B
FIG. 3C

SEQUENCE LISTING

```
<160> NUMBER OF SEQ ID NOS: 36

<210> SEQ ID NO 1
<211> LENGTH: 1134
<212> TYPE: PRT
<213> ORGANISM: Mus musculus

<400> SEQUENCE: 1
```

-continued

```
Met Asp Glu Leu Ala Phe Gly Glu Ala Ala Leu Glu Gln Thr Leu Ala
1               5                   10                  15
Glu Met Cys Glu Leu Asp Thr Ala Val Leu Asn Asp Ile Glu Asp Met
            20                  25                  30
Leu Gln Leu Ile Asn Asn Gln Asp Ser Asp Phe Pro Gly Leu Phe Asp
            35                  40                  45
Ala Pro Tyr Ala Gly Gly Glu Thr Gly Asp Thr Gly Pro Ser Ser Pro
        50                  55                  60
Gly Ala Asn Ser Pro Glu Ser Phe Ser Ser Ala Ser Leu Ala Ser Ser
65                  70                  75                  80
Leu Glu Ala Phe Leu Gly Gly Pro Lys Val Thr Pro Ala Pro Leu Ser
                85                  90                  95
Pro Pro Pro Ser Ala Pro Ala Ala Leu Lys Met Tyr Pro Ser Val Ser
                100                 105                 110
Pro Phe Ser Pro Gly Pro Gly Ile Lys Glu Glu Pro Val Pro Leu Thr
            115                 120                 125
Ile Leu Gln Pro Ala Ala Pro Gln Pro Ser Pro Gly Thr Leu Leu Pro
            130                 135                 140
Pro Ser Phe Pro Ala Pro Pro Val Gln Leu Ser Pro Ala Pro Val Leu
145                 150                 155                 160
Gly Tyr Ser Ser Leu Pro Ser Gly Phe Ser Gly Thr Leu Pro Gly Asn
                165                 170                 175
Thr Gln Gln Pro Pro Ser Ser Leu Pro Leu Ala Pro Ala Pro Gly Val
            180                 185                 190
Leu Pro Thr Pro Ala Leu His Thr Gln Val Gln Ser Leu Ala Ser Gln
            195                 200                 205
Gln Pro Leu Pro Ala Ser Ala Ala Pro Arg Thr Asn Thr Val Thr Ser
    210                 215                 220
Gln Val Gln Gln Val Pro Val Val Leu Gln Pro His Phe Ile Lys Ala
225                 230                 235                 240
Asp Ser Leu Leu Leu Thr Ala Val Lys Thr Asp Ala Gly Ala Thr Val
                245                 250                 255
Lys Thr Ala Gly Ile Ser Thr Leu Ala Pro Gly Thr Ala Val Gln Ala
            260                 265                 270
Gly Pro Leu Gln Thr Leu Val Ser Gly Gly Thr Ile Leu Ala Thr Val
            275                 280                 285
Pro Leu Val Val Asp Thr Asp Lys Leu Pro Ile His Arg Leu Ala Ala
    290                 295                 300
Gly Ser Lys Ala Leu Gly Ser Ala Gln Ser Arg Gly Glu Lys Arg Thr
305                 310                 315                 320
Ala His Asn Ala Ile Glu Lys Arg Tyr Arg Ser Ser Ile Asn Asp Lys
                325                 330                 335
Ile Val Glu Leu Lys Asp Leu Val Val Gly Thr Glu Ala Lys Leu Asn
            340                 345                 350
Lys Ser Ala Val Leu Arg Lys Ala Ile Asp Tyr Ile Arg Phe Leu Gln
            355                 360                 365
His Ser Asn Gln Lys Leu Lys Gln Glu Asn Leu Thr Leu Arg Ser Ala
    370                 375                 380
His Lys Ser Lys Ser Leu Lys Asp Leu Val Ser Ala Cys Gly Ser Gly
385                 390                 395                 400
Gly Gly Thr Asp Val Ser Met Glu Gly Met Lys Pro Glu Val Val Glu
                405                 410                 415
```

Thr Leu Thr Pro Pro Ser Asp Ala Gly Ser Pro Ser Gln Ser Ser
            420             425             430

Pro Leu Ser Phe Gly Ser Arg Ala Ser Ser Gly Gly Ser Asp Ser
            435             440             445

Glu Pro Asp Ser Pro Ala Phe Glu Asp Ser Gln Val Lys Ala Gln Arg
450                 455                 460

Leu Pro Ser His Ser Arg Gly Met Leu Asp Arg Ser Arg Leu Ala Leu
465                 470                 475                 480

Cys Val Leu Ala Phe Leu Cys Leu Thr Cys Asn Pro Leu Ala Ser Leu
                485                 490                 495

Phe Gly Trp Gly Ile Leu Thr Pro Ser Asp Ala Thr Gly Thr His Arg
            500                 505                 510

Ser Ser Gly Arg Ser Met Leu Glu Ala Glu Ser Arg Asp Gly Ser Asn
            515                 520                 525

Trp Thr Gln Trp Leu Leu Pro Pro Leu Val Trp Leu Ala Asn Gly Leu
        530                 535                 540

Leu Val Leu Ala Cys Leu Ala Leu Leu Phe Val Tyr Gly Glu Pro Val
545                 550                 555                 560

Thr Arg Pro His Ser Gly Pro Ala Val His Phe Trp Arg His Arg Lys
                565                 570                 575

Gln Ala Asp Leu Asp Leu Ala Arg Gly Asp Phe Pro Gln Ala Ala Gln
            580                 585                 590

Gln Leu Trp Leu Ala Leu Gln Ala Leu Gly Arg Pro Leu Pro Thr Ser
        595                 600                 605

Asn Leu Asp Leu Ala Cys Ser Leu Leu Trp Asn Leu Ile Arg His Leu
            610                 615                 620

Leu Gln Arg Leu Trp Val Gly Arg Trp Leu Ala Gly Gln Ala Gly Gly
625                 630                 635                 640

Leu Leu Arg Asp Arg Gly Leu Arg Lys Asp Ala Arg Ala Ser Ala Arg
                645                 650                 655

Asp Ala Ala Val Val Tyr His Lys Leu His Gln Leu His Ala Met Gly
                660                 665                 670

Lys Tyr Thr Gly Gly His Leu Ala Ala Ser Asn Leu Ala Leu Ser Ala
            675                 680                 685

Leu Asn Leu Ala Glu Cys Ala Gly Asp Ala Ile Ser Met Ala Thr Leu
        690                 695                 700

Ala Glu Ile Tyr Val Ala Ala Leu Arg Val Lys Thr Ser Leu Pro
705                 710                 715                 720

Arg Ala Leu His Phe Leu Thr Arg Phe Phe Leu Ser Ser Ala Arg Gln
                725                 730                 735

Ala Cys Leu Ala Gln Ser Gly Ser Val Pro Leu Ala Met Gln Trp Leu
            740                 745                 750

Cys His Pro Val Gly His Arg Phe Phe Val Asp Gly Asp Trp Ala Val
        755                 760                 765

His Gly Ala Pro Pro Glu Ser Leu Tyr Ser Val Ala Gly Asn Pro Val
    770                 775                 780

Asp Pro Leu Ala Gln Val Thr Arg Leu Phe Arg Glu His Leu Leu Glu
785                 790                 795                 800

Arg Ala Leu Asn Cys Ile Ala Gln Pro Ser Pro Gly Ala Ala Asp Gly
                805                 810                 815

Asp Arg Glu Phe Ser Asp Ala Leu Gly Tyr Leu Gln Leu Leu Asn Ser
            820                 825                 830

Cys Ser Asp Ala Ala Gly Ala Pro Ala Cys Ser Phe Ser Val Ser Ser

```
                835                 840                 845
Ser Met Ala Ala Thr Thr Gly Pro Asp Pro Val Ala Lys Trp Trp Ala
    850                 855                 860
Ser Leu Thr Ala Val Val Ile His Trp Leu Arg Arg Asp Glu Glu Ala
865                 870                 875                 880
Ala Glu Arg Leu Tyr Pro Leu Val Glu His Ile Pro Gln Val Leu Gln
                885                 890                 895
Asp Thr Glu Arg Pro Leu Pro Arg Ala Ala Leu Tyr Ser Phe Lys Ala
                900                 905                 910
Ala Arg Ala Leu Leu Asp His Arg Lys Val Glu Ser Ser Pro Ala Ser
                915                 920                 925
Leu Ala Ile Cys Glu Lys Ala Ser Gly Tyr Leu Arg Asp Ser Leu Ala
930                 935                 940
Ser Thr Pro Thr Gly Ser Ser Ile Asp Lys Ala Met Gln Leu Leu Leu
945                 950                 955                 960
Cys Asp Leu Leu Leu Val Ala Arg Thr Ser Leu Trp Gln Arg Gln Gln
                965                 970                 975
Ser Pro Ala Ser Val Gln Val Ala His Gly Thr Ser Asn Gly Pro Gln
                980                 985                 990
Ala Ser Ala Leu Glu Leu Arg Gly Phe Gln His Asp Leu Ser Ser Leu
                995                 1000                1005
Arg Arg Leu Ala Gln Ser Phe Arg Pro Ala Met Arg Arg Val Phe
    1010                1015                1020
Leu His Glu Ala Thr Ala Arg Leu Met Ala Gly Ala Ser Pro Ala
    1025                1030                1035
Arg Thr His Gln Leu Leu Asp Arg Ser Leu Arg Arg Ala Gly
    1040                1045                1050
Ser Ser Gly Lys Gly Gly Thr Thr Ala Glu Leu Glu Pro Arg Pro
    1055                1060                1065
Thr Trp Arg Glu His Thr Glu Ala Leu Leu Leu Ala Ser Cys Tyr
    1070                1075                1080
Leu Pro Pro Ala Phe Leu Ser Ala Pro Gly Gln Arg Met Ser Met
    1085                1090                1095
Leu Ala Glu Ala Ala Arg Thr Val Glu Lys Leu Gly Asp His Arg
    1100                1105                1110
Leu Leu Leu Asp Cys Gln Gln Met Leu Leu Arg Leu Gly Gly Gly
    1115                1120                1125
Thr Thr Val Thr Ser Ser
    1130

<210> SEQ ID NO 2
<211> LENGTH: 3405
<212> TYPE: DNA
<213> ORGANISM: Mus musculus

<400> SEQUENCE: 2
atggacgagc tggccttcgg tgaggcggct ctggaacaga cactggccga gatgtgcgaa      60
ctggacacag cggttttgaa cgacatcgaa gacatgctcc agctcatcaa caaccaagac     120
agtgacttcc cgggcctgtt tgacgccccc tatgctgggg gtgagacagg ggacacaggc     180
cccagcagcc aggtgccaa ctctcctgag agcttctctt ctgcttctct ggcctcctct     240
ctggaagcct tcctgggagg acccaaggtg acacctgcac ccttgtcccc tccaccatcg     300
gcacccgctg ctttaaagat gtaccccgtcc gtgtcccccct tttccccctgg gcctgggatc     360
```

```
aaagaggagc cagtgccact caccatccta cagcctgcag cgccacagcc gtcaccgggg    420
accctcctgc ctccgagctt ccccgcacca cccgtacagc tcagccctgc gcccgtgctg    480
ggttactcga gcctgccttc aggcttctca gggacccttc caggaaacac tcagcagcca    540
ccatctagcc tgccgctggc ccctgcacca ggagtcttgc ccaccctgc cctgcacacc     600 caggtccaaa gcttggcctc ccagcagccg ctgccagcct cagcagcccc tagaacaaac    660
actgtgacct cacaggtcca gcaggtccca gttgtactgc agccacactt catcaaggca    720
gactcactgc tgctgacagc tgtgaagaca gatgcaggag ccaccgtgaa gactgcaggc    780
atcagcaccc tggctcctgg cacagccgtg caggcaggtc ccctgcagac cctggtgagt    840
ggagggacca tcttggccac agtaccttg gttgtggaca cagacaaact gcccatccac     900
cgactcgcag ctggcagcaa ggccctaggc tcagctcaga gccgtggtga aagcgcaca     960 gcccacaatg ccattgagaa cgctaccgg tcttctatca atgacaagat tgtggagctc    1020
aaagacctgg tggtgggcac tgaagcaaag ctgaataaat ctgctgtctt gcgcaaggcc   1080
atcgactaca tccgcttctt gcagcacagc aaccagaagc tcaagcagga aacctgacc    1140 ctacgaagtg cacacaaaag caaatcactg aaggacctgg tgtcagcttg tggcagtgga   1200
ggaggcacag atgtgtctat ggagggcatg aaacccgaag tggtggagac gcttacccct   1260
ccaccctcag acgccggctc accctcccag agtagcccct tgtcttttgg cagcagagct   1320
agcagcagtg gtggtagtga ctctgagccc gacagtccag cctttgagga tagccaggtc   1380
aaagcccagc ggctgccttc acacagccga ggcatgctgg accgctcccg cctggccctg   1440
tgtgtactgg cctttctgtg tctgacctgc aatcctttgg cctcgctttt cggctggggc   1500
attctcactc cctctgatgc tacgggtaca caccgtagtt ctgggcgcag catgctggag   1560
gcagagagca gagatggctc taattggacc cagtggttgc tgccacccct agtctggctg   1620
gccaatggac tactagtgtt ggcctgcttg gctcttctct ttgtctatgg ggaacctgtg   1680
actaggccac actctggccc ggctgtacac ttctggagac atcgcaaaca agctgacctg   1740
gatttggccc ggggagattt ccccccaggct gctcaacagc tgtggctggc cctgcaagcg   1800
ctgggccggc ccctgcccac ctcaaacctg gatctggcct gcagtctgct ttggaacctc   1860
atccgccacc tgctccagcg tctctgggtg gccgctggc tggcaggcca ggccgggggc    1920
ctgctgaggg accgtgggct gaggaaggat gcccgtgcca gtgcccggga tgcggctgtt   1980
gtctaccata agctgcacca gctgcatgcc atgggcaagt acacaggagg acatcttgct   2040
gcttctaacc tggcactaag tgccctcaac ctggctgagt gcgcaggaga tgctatctcc   2100
atggcaacac tggcagagat ctatgtggca gcggccctga gggtcaaaac cagcctccca   2160
agagccctgc acttcttgac acgtttcttc ctgagcagcg cccgccaggc ctgcctagca   2220
cagagcggct cggtgcctct tgccatgcag tggctctgcc accctgtagg tcaccgtttc   2280
tttgtggacg gggactgggc cgtgcacggt gccccccgg agagcctgta cagcgtggct    2340
gggaacccag tggatccgct ggcccaggtg accggctat ccgtgaaca tctcctagag     2400 cgagcgttga actgtattgc tcagcccagc ccaggggcag ctgacggaga cagggagttc   2460
tcagatgccc ttggatatct gcagttgcta aatagctgtt ctgatgctgc cggggctcct   2520
gcttgcagtt tctctgtcag ctccagcatg gctgccacca ctggcccaga cccagtggcc   2580
aagtggtggg cctcactgac agctgtggtg atccactggc tgaggcggga tgaagaggca   2640
gctgagcgct tgtacccact ggtagagcat atccccagg tgctgcagga cactgagaga    2700
cccctgccca gggcagctct gtactccttc aaggctgccc gggctctgct ggaccacaga   2760
```

```
aaggtggaat ctagcccagc cagcctggcc atctgtgaga aggccagtgg gtacctgcgg    2820
gacagcttag cctctacacc aactggcagt tccattgaca aggccatgca gctgctcctg    2880
tgtgatctac ttcttgtggc ccgtaccagt ctgtggcagc ggcagcagtc accagcttca    2940
gtccaggtag ctcacggtac cagcaatgga ccccaggcct ctgctctgga gctgcgtggt    3000
ttccaacatg acctgagcag cctgcggcgg ttggcacaga gcttccggcc tgctatgagg    3060
agggtattcc tacatgaggc cacagctcgg ctgatggcag gagcaagtcc tgcccggaca    3120
caccagctcc tggatcgcag tctgaggagg agggcaggtt ccagtggcaa aggaggcact    3180
acagctgagc tggagccacg gcccacatgg cgggagcaca ccgaggccct gctgttggca    3240
tcctgctatc tgcccctgc cttcctgtcg gctcctgggc agcgaatgag catgctggcc    3300
gaggcggcac gcaccgtaga gaagcttggc gatcaccggc tactgctgga ctgccagcag    3360
atgctcctgc gcctgggcgg cggaaccacc gtcacttcca gctag    3405
```

<210> SEQ ID NO 3
<211> LENGTH: 355
<212> TYPE: PRT
<213> ORGANISM: Mus musculus

<400> SEQUENCE: 3

```
Met Pro Ala His Met Leu Gln Glu Ile Ser Ser Tyr Thr Thr Thr
1               5                   10                  15

Thr Thr Ile Thr Ala Pro Pro Ser Gly Asn Glu Arg Glu Lys Val Lys
            20                  25                  30

Thr Val Pro Leu His Leu Glu Glu Asp Ile Arg Pro Glu Met Lys Glu
        35                  40                  45

Asp Ile His Asp Pro Thr Tyr Gln Asp Glu Gly Pro Pro Pro Lys
    50                  55                  60

Leu Glu Tyr Val Trp Arg Asn Ile Ile Leu Met Val Leu Leu His Leu
65                  70                  75                  80

Gly Gly Leu Tyr Gly Ile Ile Leu Val Pro Ser Cys Lys Leu Tyr Thr
                85                  90                  95

Cys Leu Phe Gly Ile Phe Tyr Tyr Met Thr Ser Ala Leu Gly Ile Thr
            100                 105                 110

Ala Gly Ala His Arg Leu Trp Ser His Arg Thr Tyr Lys Ala Arg Leu
        115                 120                 125

Pro Leu Arg Ile Phe Leu Ile Ile Ala Asn Thr Met Ala Phe Gln Asn
    130                 135                 140

Asp Val Tyr Glu Trp Ala Arg Asp His Arg Ala His His Lys Phe Ser
145                 150                 155                 160

Glu Thr His Ala Asp Pro His Asn Ser Arg Arg Gly Phe Phe Phe Ser
                165                 170                 175

His Val Gly Trp Leu Leu Val Arg Lys His Pro Ala Val Lys Glu Lys
            180                 185                 190

Gly Gly Lys Leu Asp Met Ser Asp Leu Lys Ala Glu Lys Leu Val Met
        195                 200                 205

Phe Gln Arg Arg Tyr Tyr Lys Pro Gly Leu Leu Leu Met Cys Phe Ile
    210                 215                 220

Leu Pro Thr Leu Val Pro Trp Tyr Cys Trp Gly Glu Thr Phe Val Asn
225                 230                 235                 240

Ser Leu Phe Val Ser Thr Phe Leu Arg Tyr Thr Leu Val Leu Asn Ala
                245                 250                 255
```

Thr Trp Leu Val Asn Ser Ala Ala His Leu Tyr Gly Tyr Arg Pro Tyr
            260                 265                 270

Asp Lys Asn Ile Gln Ser Arg Glu Asn Ile Leu Val Ser Leu Gly Ala
        275                 280                 285

Val Gly Glu Gly Phe His Asn Tyr His His Thr Phe Pro Phe Asp Tyr
    290                 295                 300

Ser Ala Ser Glu Tyr Arg Trp His Ile Asn Phe Thr Thr Phe Phe Ile
305                 310                 315                 320

Asp Cys Met Ala Ala Leu Gly Leu Ala Tyr Asp Arg Lys Lys Val Ser
                325                 330                 335

Lys Ala Thr Val Leu Ala Arg Ile Lys Arg Thr Gly Asp Gly Ser His
            340                 345                 350

Lys Ser Ser
        355

<210> SEQ ID NO 4
<211> LENGTH: 1068
<212> TYPE: DNA
<213> ORGANISM: Mus musculus

<400> SEQUENCE: 4
atgccggccc acatgctcca agagatctcc agttcttaca cgaccaccac caccatcact        60
gcacctccct ccggaaatga acgagagaag gtgaagacgg tgcccctcca cctggaagaa       120
gacatccgtc tgaaatgaa agaagatatt cacgacccca cctatcagga tgaggaggga       180
cccccgccca agctggagta cgtctggagg aacatcattc tcatggtcct gctgcacttg       240
ggaggcctgt acgggatcat actggttccc tcctgcaagc tctacacctg cctcttcggg       300
attttctact acatgaccag cgctctgggc atcacagccg ggctcatcg cctctggagc        360 cacagaactt acaaggcacg gctgcccctg cggatcttcc ttatcattgc caacaccatg       420
gcgttccaga tgacgtgta cgaatgggcc cgagatcacc gcgcccacca caagttctca        480
gaaacacacg ccgaccctca caattcccgc cgtggcttct tcttctctca cgtgggttgg       540
ctgcttgtgc gcaaacaccc ggctgtcaaa gagaagggcg aaaactgga catgtctgac        600 ctgaaagccg agaagctggt gatgttccag aggaggtact acaagcccgg cctcctgctg       660
atgtgcttca tcctgcccac gctggtgccc tggtactgct ggggcgagac ttttgtaaac       720
agcctgttcg ttagcacctt cttgcgatac actctggtgc tcaacgccac ctggctggtg       780
aacagtgccg cgcatctcta tggatatcgc ccctacgaca gaacattca atcccgggag        840 aatatcctgg tttccctggg tgccgtgggc gagggcttcc acaactacca ccacaccttc       900
cccttcgact actctgccag tgagtaccgc tggcacatca acttccacca gttcttcatc       960
gactgcatgg ctgccctggg cctggcttac gaccggaaga agtttctaa ggctactgtc       1020 ttagccagga ttaagagaac tggagacggg agtcacaaga gtagctga                 1068

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tatgctagcg gtaccatggt gagcaagggc gagga                                35

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tatggtacca tggacgagct                    20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
atagggccct tagctggaa                     19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tatgcggccg catggacgag                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
atactcgagc ggctactctt                    20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tatggtacca tgccggcc                      18

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atactcgagt cagctactct tgt                23

<210> SEQ ID NO 12

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tatggtacca tgccggcc                                                    18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atactcgagc ggctactctt                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tatgcggccg catggacgag                                                  20

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atatctagac tagctggaag tgacggtggt tcc                                   33

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tatgcggccg catggacgag                                                  20

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atatctagac tgctggaagt gacggtggtt c                                     31

<210> SEQ ID NO 18
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tatgcggccg catggacgag                                                    20

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atatctagat cacatgccct ccatagacac atctgtg                                 37

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tatgcggccg catggacgag                                                    20

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atatctagac tcatgccctc catagacaca tctgtg                                  36

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tatggtacca tgccggcc                                                      18

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atactcgagt cagctactct tgt                                                23

<210> SEQ ID NO 24
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 24
tatggtacca tgccggcc                                                    18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atactcgagc ggctactctt                                                  20

<210> SEQ ID NO 26
<211> LENGTH: 410
<212> TYPE: PRT
<213> ORGANISM: Mus musculus

<400> SEQUENCE: 26
```

Met Asp Glu Leu Ala Phe Gly Glu Ala Ala Leu Glu Gln Thr Leu Ala
1               5                   10                  15

Glu Met Cys Glu Leu Asp Thr Ala Val Leu Asn Asp Ile Glu Asp Met
            20                  25                  30

Leu Gln Leu Ile Asn Asn Gln Asp Ser Asp Phe Pro Gly Leu Phe Asp
        35                  40                  45

Ala Pro Tyr Ala Gly Gly Glu Thr Gly Asp Thr Gly Pro Ser Ser Pro
    50                  55                  60

Gly Ala Asn Ser Pro Glu Ser Phe Ser Ala Ser Leu Ala Ser Ser
65                  70                  75                  80

Leu Glu Ala Phe Leu Gly Gly Pro Lys Val Thr Pro Ala Pro Leu Ser
                85                  90                  95

Pro Pro Pro Ser Ala Pro Ala Ala Leu Lys Met Tyr Pro Ser Val Ser
            100                 105                 110

Pro Phe Ser Pro Gly Pro Gly Ile Lys Glu Glu Pro Val Pro Leu Thr
        115                 120                 125

Ile Leu Gln Pro Ala Ala Pro Gln Pro Ser Pro Gly Thr Leu Leu Pro
    130                 135                 140

Pro Ser Phe Pro Ala Pro Val Gln Leu Ser Pro Ala Pro Val Leu
145                 150                 155                 160

Gly Tyr Ser Ser Leu Pro Ser Gly Phe Ser Gly Thr Leu Pro Gly Asn
                165                 170                 175

Thr Gln Gln Pro Pro Ser Ser Leu Pro Leu Ala Pro Ala Pro Gly Val
            180                 185                 190

Leu Pro Thr Pro Ala Leu His Thr Gln Val Gln Ser Leu Ala Ser Gln
        195                 200                 205

Gln Pro Leu Pro Ala Ser Ala Ala Pro Arg Thr Asn Thr Val Thr Ser
    210                 215                 220

Gln Val Gln Gln Val Pro Val Val Leu Gln Pro His Phe Ile Lys Ala
225                 230                 235                 240

Asp Ser Leu Leu Leu Thr Ala Val Lys Thr Asp Ala Gly Ala Thr Val
                245                 250                 255

Lys Thr Ala Gly Ile Ser Thr Leu Ala Pro Gly Thr Ala Val Gln Ala

```
                    260                 265                 270
Gly Pro Leu Gln Thr Leu Val Ser Gly Gly Thr Ile Leu Ala Thr Val
                275                 280                 285

Pro Leu Val Val Asp Thr Asp Lys Leu Pro Ile His Arg Leu Ala Ala
            290                 295                 300

Gly Ser Lys Ala Leu Gly Ser Ala Gln Ser Arg Gly Glu Lys Arg Thr
305                 310                 315                 320

Ala His Asn Ala Ile Glu Lys Arg Tyr Arg Ser Ser Ile Asn Asp Lys
                325                 330                 335

Ile Val Glu Leu Lys Asp Leu Val Gly Thr Glu Ala Lys Leu Asn
            340                 345                 350

Lys Ser Ala Val Leu Arg Lys Ala Ile Asp Tyr Ile Arg Phe Leu Gln
                355                 360                 365

His Ser Asn Gln Lys Leu Lys Gln Glu Asn Leu Thr Leu Arg Ser Ala
            370                 375                 380

His Lys Ser Lys Ser Leu Lys Asp Leu Val Ser Ala Cys Gly Ser Gly
385                 390                 395                 400

Gly Gly Thr Asp Val Ser Met Glu Gly Met
                405                 410

<210> SEQ ID NO 27
<211> LENGTH: 320
<212> TYPE: PRT
<213> ORGANISM: Mus musculus

<400> SEQUENCE: 27

Met Pro Ala Pro Leu Ser Pro Pro Ser Ala Pro Ala Leu Lys
1               5                   10                  15

Met Tyr Pro Ser Val Ser Pro Phe Ser Pro Gly Pro Gly Ile Lys Glu
                20                  25                  30

Glu Pro Val Pro Leu Thr Ile Leu Gln Pro Ala Ala Pro Gln Pro Ser
            35                  40                  45

Pro Gly Thr Leu Leu Pro Pro Ser Phe Pro Ala Pro Pro Val Gln Leu
50                  55                  60

Ser Pro Ala Pro Val Leu Gly Tyr Ser Ser Leu Pro Ser Gly Phe Ser
65                  70                  75                  80

Gly Thr Leu Pro Gly Asn Thr Gln Gln Pro Ser Ser Leu Pro Leu
                85                  90                  95

Ala Pro Ala Pro Gly Val Leu Pro Thr Pro Ala Leu His Thr Gln Val
            100                 105                 110

Gln Ser Leu Ala Ser Gln Gln Pro Leu Pro Ala Ser Ala Ala Pro Arg
        115                 120                 125

Thr Asn Thr Val Thr Ser Gln Val Gln Gln Val Pro Val Val Leu Gln
130                 135                 140

Pro His Phe Ile Lys Ala Asp Ser Leu Leu Thr Ala Val Lys Thr
145                 150                 155                 160

Asp Ala Gly Ala Thr Val Lys Thr Ala Gly Ile Ser Thr Leu Ala Pro
                165                 170                 175

Gly Thr Ala Val Gln Ala Gly Pro Leu Gln Thr Leu Val Ser Gly Gly
            180                 185                 190

Thr Ile Leu Ala Thr Val Pro Leu Val Val Asp Thr Asp Lys Leu Pro
        195                 200                 205

Ile His Arg Leu Ala Ala Gly Ser Lys Ala Leu Gly Ser Ala Gln Ser
210                 215                 220
```

```
Arg Gly Glu Lys Arg Thr Ala His Asn Ala Ile Glu Lys Arg Tyr Arg
225                 230                 235                 240

Ser Ser Ile Asn Asp Lys Ile Val Glu Leu Lys Asp Leu Val Val Gly
            245                 250                 255

Thr Glu Ala Lys Leu Asn Lys Ser Ala Val Leu Arg Lys Ala Ile Asp
        260                 265                 270

Tyr Ile Arg Phe Leu Gln His Ser Asn Gln Lys Leu Lys Gln Glu Asn
            275                 280                 285

Leu Thr Leu Arg Ser Ala His Lys Ser Lys Ser Leu Lys Asp Leu Val
        290                 295                 300

Ser Ala Cys Gly Ser Gly Gly Thr Asp Val Ser Met Glu Gly Met
305                 310                 315                 320

<210> SEQ ID NO 28
<211> LENGTH: 1177
<212> TYPE: PRT
<213> ORGANISM: Homo sapiens

<400> SEQUENCE: 28

Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Gly Glu
            20                  25                  30

Val Gly Ala Gly Arg Gly Arg Ala Asn Gly Leu Asp Ala Pro Arg Ala
        35                  40                  45

Gly Ala Asp Arg Gly Ala Met Asp Cys Thr Phe Glu Asp Met Leu Gln
    50                  55                  60

Leu Ile Asn Asn Gln Asp Ser Asp Phe Pro Gly Leu Phe Asp Pro Pro
65                  70                  75                  80

Tyr Ala Gly Ser Gly Ala Gly Gly Thr Asp Pro Ala Ser Pro Asp Thr
                85                  90                  95

Ser Ser Pro Gly Ser Leu Ser Pro Pro Pro Ala Thr Leu Ser Ser Ser
            100                 105                 110

Leu Glu Ala Phe Leu Ser Gly Pro Gln Ala Ala Pro Ser Pro Leu Ser
        115                 120                 125

Pro Pro Gln Pro Ala Pro Thr Pro Leu Lys Met Tyr Pro Ser Met Pro
    130                 135                 140

Ala Phe Ser Pro Gly Pro Gly Ile Lys Glu Glu Ser Val Pro Leu Ser
145                 150                 155                 160

Ile Leu Gln Thr Pro Thr Pro Gln Pro Leu Pro Gly Ala Leu Leu Pro
                165                 170                 175

Gln Ser Phe Pro Ala Pro Ala Pro Pro Gln Phe Ser Ser Thr Pro Val
            180                 185                 190

Leu Gly Tyr Pro Ser Pro Pro Gly Gly Phe Ser Thr Gly Ser Pro Pro
        195                 200                 205

Gly Asn Thr Gln Gln Pro Leu Pro Gly Leu Pro Leu Ala Ser Pro Pro
    210                 215                 220

Gly Val Pro Pro Val Ser Leu His Thr Gln Val Gln Ser Val Val Pro
225                 230                 235                 240

Gln Gln Leu Leu Thr Val Thr Ala Ala Pro Thr Ala Ala Pro Val Thr
                245                 250                 255

Thr Thr Val Thr Ser Gln Ile Gln Gln Val Pro Val Leu Leu Gln Pro
            260                 265                 270

His Phe Ile Lys Ala Asp Ser Leu Leu Leu Thr Ala Met Lys Thr Asp
        275                 280                 285
```

```
Gly Ala Thr Val Lys Ala Ala Gly Leu Ser Pro Leu Val Ser Gly Thr
        290                 295                 300

Thr Val Gln Thr Gly Pro Leu Pro Thr Leu Val Ser Gly Gly Thr Ile
305                 310                 315                 320

Leu Ala Thr Val Pro Leu Val Val Asp Ala Glu Lys Leu Pro Ile Asn
                325                 330                 335

Arg Leu Ala Ala Gly Ser Lys Ala Pro Ala Ser Ala Gln Ser Arg Gly
                340                 345                 350

Glu Lys Arg Thr Ala His Asn Ala Ile Glu Lys Arg Tyr Arg Ser Ser
        355                 360                 365

Ile Asn Asp Lys Ile Ile Glu Leu Lys Asp Leu Val Val Gly Thr Glu
370                 375                 380

Ala Lys Leu Asn Lys Ser Ala Val Leu Arg Lys Ala Ile Asp Tyr Ile
385                 390                 395                 400

Arg Phe Leu Gln His Ser Asn Gln Lys Leu Lys Gln Glu Asn Leu Ser
                405                 410                 415

Leu Arg Thr Ala Val His Lys Ser Lys Ser Leu Lys Asp Leu Val Ser
                420                 425                 430

Ala Cys Gly Ser Gly Asn Thr Asp Val Leu Met Glu Gly Val Lys
                435                 440                 445

Thr Glu Val Glu Asp Thr Leu Thr Pro Pro Ser Asp Ala Gly Ser
450                 455                 460

Pro Phe Gln Ser Ser Pro Leu Ser Leu Gly Ser Arg Gly Ser Gly Ser
465                 470                 475                 480

Gly Gly Ser Gly Ser Asp Ser Glu Pro Asp Ser Pro Val Phe Glu Asp
                485                 490                 495

Ser Lys Ala Lys Pro Glu Gln Arg Pro Ser Leu His Ser Arg Gly Met
                500                 505                 510

Leu Asp Arg Ser Arg Leu Ala Leu Cys Thr Leu Val Phe Leu Cys Leu
        515                 520                 525

Ser Cys Asn Pro Leu Ala Ser Leu Leu Gly Ala Arg Gly Leu Pro Ser
530                 535                 540

Pro Ser Asp Thr Thr Ser Val Tyr His Ser Pro Gly Arg Asn Val Leu
545                 550                 555                 560

Gly Thr Glu Ser Arg Asp Gly Pro Gly Trp Ala Gln Trp Leu Leu Pro
                565                 570                 575

Pro Val Val Trp Leu Leu Asn Gly Leu Leu Val Leu Val Ser Leu Val
                580                 585                 590

Leu Leu Phe Val Tyr Gly Glu Pro Val Thr Arg Pro His Ser Gly Pro
        595                 600                 605

Ala Val Tyr Phe Trp Arg His Arg Lys Gln Ala Asp Leu Asp Leu Ala
610                 615                 620

Arg Gly Asp Phe Ala Gln Ala Ala Gln Gln Leu Trp Leu Ala Leu Arg
625                 630                 635                 640

Ala Leu Gly Arg Pro Leu Pro Thr Ser His Leu Asp Leu Ala Cys Ser
                645                 650                 655

Leu Leu Trp Asn Leu Ile Arg His Leu Leu Gln Arg Leu Trp Val Gly
                660                 665                 670

Arg Trp Leu Ala Gly Arg Ala Gly Gly Leu Gln Gln Asp Cys Ala Leu
        675                 680                 685

Arg Val Asp Ala Ser Ala Ser Ala Arg Asp Ala Ala Leu Val Tyr His
690                 695                 700
```

```
Lys Leu His Gln Leu His Thr Met Gly Lys His Thr Gly Gly His Leu
705                 710                 715                 720

Thr Ala Thr Asn Leu Ala Leu Ser Ala Leu Asn Leu Ala Glu Cys Ala
            725                 730                 735

Gly Asp Ala Val Ser Val Ala Thr Leu Ala Glu Ile Tyr Val Ala Ala
            740                 745                 750

Ala Leu Arg Val Lys Thr Ser Leu Pro Arg Ala Leu His Phe Leu Thr
            755                 760                 765

Arg Phe Phe Leu Ser Ser Ala Arg Gln Ala Cys Leu Ala Gln Ser Gly
            770                 775                 780

Ser Val Pro Pro Ala Met Gln Trp Leu Cys His Pro Val Gly His Arg
785                 790                 795                 800

Phe Phe Val Asp Gly Asp Trp Ser Val Leu Ser Thr Pro Trp Glu Ser
            805                 810                 815

Leu Tyr Ser Leu Ala Gly Asn Pro Val Asp Pro Leu Ala Gln Val Thr
            820                 825                 830

Gln Leu Phe Arg Glu His Leu Leu Glu Arg Ala Leu Asn Cys Val Thr
            835                 840                 845

Gln Pro Asn Pro Ser Pro Gly Ser Ala Asp Gly Asp Lys Glu Phe Ser
850                 855                 860

Asp Ala Leu Gly Tyr Leu Gln Leu Leu Asn Ser Cys Ser Asp Ala Ala
865                 870                 875                 880

Gly Ala Pro Ala Tyr Ser Phe Ser Ile Ser Ser Met Ala Thr Thr
            885                 890                 895

Thr Gly Val Asp Pro Val Ala Lys Trp Trp Ala Ser Leu Thr Ala Val
            900                 905                 910

Val Ile His Trp Leu Arg Arg Asp Glu Glu Ala Ala Glu Arg Leu Cys
            915                 920                 925

Pro Leu Val Glu His Leu Pro Arg Val Leu Gln Glu Ser Glu Arg Pro
            930                 935                 940

Leu Pro Arg Ala Ala Leu His Ser Phe Lys Ala Ala Arg Ala Leu Leu
945                 950                 955                 960

Gly Cys Ala Lys Ala Glu Ser Gly Pro Ala Ser Leu Thr Ile Cys Glu
            965                 970                 975

Lys Ala Ser Gly Tyr Leu Gln Asp Ser Leu Ala Thr Thr Pro Ala Ser
            980                 985                 990

Ser Ser Ile Asp Lys Ala Val Gln Leu Phe Leu Cys Asp Leu Leu Leu
            995                 1000                1005

Val Val Arg Thr Ser Leu Trp Arg Gln Gln Gln Pro Pro Ala Pro
    1010                1015                1020

Ala Pro Ala Ala Gln Gly Thr Ser Ser Arg Pro Gln Ala Ser Ala
    1025                1030                1035

Leu Glu Leu Arg Gly Phe Gln Arg Asp Leu Ser Ser Leu Arg Arg
    1040                1045                1050

Leu Ala Gln Ser Phe Arg Pro Ala Met Arg Arg Val Phe Leu His
    1055                1060                1065

Glu Ala Thr Ala Arg Leu Met Ala Gly Ala Ser Pro Thr Arg Thr
    1070                1075                1080

His Gln Leu Leu Asp Arg Ser Leu Arg Arg Arg Ala Gly Pro Gly
    1085                1090                1095

Gly Lys Gly Gly Ala Val Ala Glu Leu Glu Pro Arg Pro Thr Arg
    1100                1105                1110

Arg Glu His Ala Glu Ala Leu Leu Leu Ala Ser Cys Tyr Leu Pro
```

```
                    1115                1120                1125
Pro Gly Phe Leu Ser Ala Pro Gly Gln Arg Val Gly Met Leu Ala
        1130                1135                1140

Glu Ala Ala Arg Thr Leu Glu Lys Leu Gly Asp Arg Arg Leu Leu
    1145                1150                1155

His Asp Cys Gln Gln Met Leu Met Arg Leu Gly Gly Gly Thr Thr
1160                1165                1170

Val Thr Ser Ser
    1175

<210> SEQ ID NO 29
<211> LENGTH: 5012
<212> TYPE: DNA
<213> ORGANISM: Homo sapiens

<400> SEQUENCE: 29
```

| | | | | | |
|---|---|---|---|---|---|
| agcagagctg | cggccggggg | aacccagttt | ccgaggaact | tttcgccggc | gccgggccgc | 60 |
| ctctgaggcc | agggcaggac | acgaacgcgc | ggagcggcgg | cggcgactga | gagccggggc | 120 |
| cgcggcggcg | ctccctagga | agggccgtac | gaggcggcgg | gcccggcggg | cctcccggag | 180 |
| gaggcggctg | cgccatggac | gagccaccct | tcagcgaggg | ggctttggag | caggcgctgg | 240 |
| gcgagccgtg | cgatctggac | gcggcgctgc | tgaccgacat | cgaaggtgaa | gtcggcgcgg | 300 |
| ggaggggtag | ggccaacggc | ctggacgccc | aagggcgggc | gcagatcgc | ggagccatgg | 360 |
| attgcacttt | cgaagacatg | cttcagctta | tcaacaacca | agacagtgac | ttccctggcc | 420 |
| tatttgaccc | accctatgct | gggagtgggg | caggggcac | agaccctgcc | agccccgata | 480 |
| ccagctcccc | aggcagcttg | tctccacctc | ctgccacatt | gagctcctct | cttgaagcct | 540 |
| tcctgagcgg | gccgcaggca | gcgccctcac | ccctgtcccc | tccccagcct | gcacccactc | 600 |
| cattgaagat | gtaccgtcc | atgcccgctt | tctcccctgg | gcctggtatc | aaggaagagt | 660 |
| cagtgccact | gagcatcctg | cagacccca | ccccacagcc | cctgccaggg | gccctcctgc | 720 |
| cacagagctt | cccagcccca | gccccaccgc | agttcagctc | caccctgtg | ttaggctacc | 780 |
| ccagccctcc | gggaggcttc | tctacaggaa | gccctcccgg | gaacacccag | cagccgctgc | 840 |
| ctggcctgcc | actggcttcc | ccgccagggg | tcccgcccgt | ctccttgcac | acccaggtcc | 900 |
| agagtgtggt | cccccagcag | ctactgacag | tcacagctgc | ccccacggca | gcccctgtaa | 960 |
| cgaccactgt | gacctcgcag | atccagcagg | tcccggtcct | gctgcagccc | cacttcatca | 1020 |
| aggcagactc | gctgcttctg | acagccatga | agacagacgg | agccactgtg | aaggcggcag | 1080 |
| gtctcagtcc | cctggtctct | ggcaccactg | tgcagacagg | gcctttgccg | accctggtga | 1140 |
| gtggcggaac | catcttggca | acagtccac | tggtcgtaga | gcggagaag | ctgcctatca | 1200 |
| accggctcgc | agctggcagc | aaggcccggg | cctctgccca | gagccgtgga | gagaagcgca | 1260 |
| cagcccacaa | cgccattgag | aagcgctacc | gctcctccat | caatgacaaa | atcattgagc | 1320 |
| tcaaggatct | ggtggtgggc | actgaggcaa | agctgaataa | atctgctgtc | ttgcgcaagg | 1380 |
| ccatcgacta | cattcgctt | ctgcaacaca | gcaaccagaa | actcaagcag | gagaacctaa | 1440 |
| gtctgcgcac | tgctgtccac | aaaagcaaat | ctctgaagga | tctggtgtcg | gcctgtggca | 1500 |
| gtggagggaa | cacagacgtg | ctcatggagg | gcgtgaagac | tgaggtggag | gacacactga | 1560 |
| ccccacccc | ctcggatgct | ggctcaccttt | tccagagcag | ccccttgtcc | cttggcagca | 1620 |
| ggggcagtgg | cagcggtggc | agtggcagtg | actcggagcc | tgacagccca | gtctttgagg | 1680 |
| acagcaaggc | aaagccagag | cagcggccgt | ctctgcacag | ccggggcatg | ctggaccgct | 1740 |

```
cccgcctggc cctgtgcacg ctcgtcttcc tctgcctgtc ctgcaacccc ttggcctcct   1800
tgctgggggc ccgggggctt cccagcccct cagataccac cagcgtctac catagccctg   1860
ggcgcaacgt gctgggcacc gagagcagag atggccctgg ctgggcccag tggctgctgc   1920
ccccagtggt ctggctgctc aatgggctgt tggtgctcgt ctccttggtg cttctctttg   1980
tctacggtga gccagtcaca cggccccact caggccccgc cgtgtacttc tggaggcatc   2040
gcaagcaggc tgacctggac ctggcccggg agactttgcc caggctgcc cagcagctgt    2100 ggctggccct gcgggcactg gccggcccc tgcccacctc ccacctggac ctggcttgta    2160
gcctcctctg gaacctcatc cgtcacctgc tgcagcgtct ctgggtgggc cgctggctgg   2220
caggccgggc aggggggcctg cagcaggact gtgctctgcg agtggatgct agcgccagcg  2280
cccgagacgc agccctggtc taccataagc tgcaccagct gcacaccatg gggaagcaca   2340
caggcgggca cctcactgcc accaacctgg cgctgagtgc cctgaacctg gcagagtgtg   2400
caggggatgc cgtgtctgtg gcgacgctgg ccgagatcta tgtggcggct gcattgagag   2460
tgaagaccag tctcccacgg gccttgcatt ttctgacacg cttcttcctg agcagtgccc   2520
gccaggcctg cctggcacag agtggctcag tgcctcctgc catgcagtgg ctctgccacc   2580
ccgtgggcca ccgtttcttc gtggatgggg actggtccgt gctcagtacc ccatgggaga   2640
gcctgtacag cttggccggg aacccagtgg acccccctggc ccaggtgact cagctattcc   2700
gggaacatct cttagagcga gcactgaact gtgtgaccca gcccaacccc agccctgggt   2760
cagctgatgg ggacaaggaa ttctcggatg ccctcgggta cctgcagctg ctgaacagct   2820
gttctgatgc tgcgggggct cctgcctaca gcttctccat cagttccagc atggccacca   2880 ccaccgcgt agaccggtg gccaagtggt gggcctctct gacagctgtg gtgatccact    2940
ggctgcggcg ggatgaggag gcggctgagc ggctgtgccc gctggtggag cacctgcccc   3000
gggtgctgca ggagtctgag agaccccctgc ccagggcagc tctgcactcc ttcaaggctg   3060
cccgggccct gctgggctgt gccaaggcag agtctggtcc agccagcctg accatctgtg   3120
agaaggccag tgggtacctg caggacagcc tggctaccac accagccagc agctccattg   3180
acaaggccgt gcagctgttc ctgtgtgacc tgcttcttgt ggtgcgcacc agcctgtggc   3240
ggcagcagca gccccggcc ccggcccag cagcccaggg caccagcagc aggccccagg     3300
cttccgccct tgagctgcgt ggcttccaac gggacctgag cagcctgagg cggctggcac   3360
agagcttccg gccgcccatg cggagggtgt tcctacatga ggccacggcc cggctgatgg   3420 cggggggccag ccccacacgg acacaccagc tcctcgaccg cagtctgagg cggcgggcag   3480
gccccggtgg caaaggaggc gcggtggcgg agctggagcc gcggcccacg cggcgggagc   3540
acgcggagcc cttgctgctg gcctcctgct acctgccccc cggcttcctg tcggcgcccg   3600
ggcagcgcgt gggcatgctg gctgaggcgg cgcgcacact cgagaagctt ggcgatcgcc   3660
ggctgctgca cgactgtcag cagatgctca tgcgcctggg cggtgggacc actgtcactt   3720
ccagctagac cccgtgtccc cggcctcagc acccctgtct ctagccactt tggtcccgtg   3780
cagcttctgt cctgcgtcga agctttgaag gccgaaggca gtgcaagaga ctctggcctc   3840
cacagttcga cctgcggctg ctgtgtgcct tcgcggtgga aggcccgagg ggcgcgatct   3900
tgaccctaag accggcggcc atgatggtgc tgacctctgg tggccgatcg gggcactgca   3960
ggggccgagc catttggggg ggccccctc cttgctctgc aggcacctta gtggcttttt    4020
tcctcctgtg tacagggaag agagggggtac atttccctgt gctgacggaa gccaacttgg   4080
```

-continued

```
ctttcccgga ctgcaagcag ggctctgccc cagaggcctc tctctccgtc gtgggagaga   4140
gacgtgtaca tagtgtaggt cagcgtgctt agcctcctga cctgaggctc ctgtgctact   4200
ttgccttttg caaactttat tttcatagat tgagaagttt tgtacagaga attaaaaatg   4260
aaattattta taatctgggt tttgtgtctt cagctgatgg atgtgctgac tagtgagagt   4320
gcttgggccc tcccccagca cctagggaaa ggcttcccct cccccctccgg ccacaaggta   4380
cacaactttt aacttagctc ttcccgatgt ttgtttgtta gtgggaggag tggggagggc   4440
tggctgtatg gcctccagcc tacctgttcc ccctgctccc agggcacatg gttgggctgt   4500
gtcaacccctt agggcctcca tggggtcagt tgtcccttct cacctcccag ctctgtcccc   4560
atcaggtccc tgggtggcac gggaggatgg actgacttcc aggacctgtt gtgtgacagg   4620
agctacagct tgggtctccc tgcaagaagt ctggcacgtc tcacctcccc catcccggcc   4680
cctggtcatc tcacagcaaa gaagcctcct ccctcccgac ctgccgccac actggagagg   4740
gggcacaggg gcgggggagg tttcctgttc tgtgaaaggc cgactccctg actccattca   4800
tgcccccccc cccagcccct ccttcattc ccattcccca acctaaagcc tggcccggct   4860
cccagctgaa tctggtcgga atccacgggc tgcagatttt ccaaaacaat cgttgtatct   4920
ttattgactt tttttttttt tttttctga atgcaatgac tgttttttac tcttaaggaa   4980
aataaacatc ttttagaaac aaaaaaaaaa aa                                 5012
```

<210> SEQ ID NO 30
<211> LENGTH: 1147
<212> TYPE: PRT
<213> ORGANISM: Homo sapiens

<400> SEQUENCE: 30

```
Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Asp Met
                20                  25                  30

Leu Gln Leu Ile Asn Asn Gln Asp Ser Asp Phe Pro Gly Leu Phe Asp
            35                  40                  45

Pro Pro Tyr Ala Gly Ser Ala Gly Gly Thr Asp Pro Ala Ser Pro
        50                  55                  60

Asp Thr Ser Ser Pro Gly Ser Leu Ser Pro Pro Ala Thr Leu Ser
65                  70                  75                  80

Ser Ser Leu Glu Ala Phe Leu Ser Gly Pro Gln Ala Ala Pro Ser Pro
                85                  90                  95

Leu Ser Pro Pro Gln Pro Ala Pro Thr Pro Leu Lys Met Tyr Pro Ser
            100                 105                 110

Met Pro Ala Phe Ser Pro Gly Pro Gly Ile Lys Glu Glu Ser Val Pro
        115                 120                 125

Leu Ser Ile Leu Gln Thr Pro Thr Pro Gln Pro Leu Pro Gly Ala Leu
    130                 135                 140

Leu Pro Gln Ser Phe Pro Ala Pro Ala Pro Pro Gln Phe Ser Ser Thr
145                 150                 155                 160

Pro Val Leu Gly Tyr Pro Ser Pro Pro Gly Gly Phe Ser Thr Gly Ser
                165                 170                 175

Pro Pro Gly Asn Thr Gln Gln Pro Leu Pro Gly Leu Pro Leu Ala Ser
            180                 185                 190

Pro Pro Gly Val Pro Pro Val Ser Leu His Thr Gln Val Gln Ser Val
        195                 200                 205
```

-continued

```
Val Pro Gln Gln Leu Leu Thr Val Thr Ala Ala Pro Thr Ala Ala Pro
210                 215                 220
Val Thr Thr Thr Val Thr Ser Gln Ile Gln Gln Val Pro Val Leu Leu
225                 230                 235                 240
Gln Pro His Phe Ile Lys Ala Asp Ser Leu Leu Leu Thr Ala Met Lys
                245                 250                 255
Thr Asp Gly Ala Thr Val Lys Ala Ala Gly Leu Ser Pro Leu Val Ser
            260                 265                 270
Gly Thr Thr Val Gln Thr Gly Pro Leu Pro Thr Leu Val Ser Gly Gly
        275                 280                 285
Thr Ile Leu Ala Thr Val Pro Leu Val Val Asp Ala Glu Lys Leu Pro
290                 295                 300
Ile Asn Arg Leu Ala Ala Gly Ser Lys Ala Pro Ala Ser Ala Gln Ser
305                 310                 315                 320
Arg Gly Glu Lys Arg Thr Ala His Asn Ala Ile Glu Lys Arg Tyr Arg
                325                 330                 335
Ser Ser Ile Asn Asp Lys Ile Ile Glu Leu Lys Asp Leu Val Val Gly
            340                 345                 350
Thr Glu Ala Lys Leu Asn Lys Ser Ala Val Leu Arg Lys Ala Ile Asp
        355                 360                 365
Tyr Ile Arg Phe Leu Gln His Ser Asn Gln Lys Leu Lys Gln Glu Asn
370                 375                 380
Leu Ser Leu Arg Thr Ala Val His Lys Ser Lys Ser Leu Lys Asp Leu
385                 390                 395                 400
Val Ser Ala Cys Gly Ser Gly Asn Thr Asp Val Leu Met Glu Gly
                405                 410                 415
Val Lys Thr Glu Val Glu Asp Thr Leu Thr Pro Pro Ser Asp Ala
            420                 425                 430
Gly Ser Pro Phe Gln Ser Ser Pro Leu Ser Leu Gly Ser Arg Gly Ser
        435                 440                 445
Gly Ser Gly Gly Ser Gly Ser Asp Ser Glu Pro Asp Ser Pro Val Phe
450                 455                 460
Glu Asp Ser Lys Ala Lys Pro Glu Gln Arg Pro Ser Leu His Ser Arg
465                 470                 475                 480
Gly Met Leu Asp Arg Ser Arg Leu Ala Leu Cys Thr Leu Val Phe Leu
                485                 490                 495
Cys Leu Ser Cys Asn Pro Leu Ala Ser Leu Leu Gly Ala Arg Gly Leu
            500                 505                 510
Pro Ser Pro Ser Asp Thr Thr Ser Val Tyr His Ser Pro Gly Arg Asn
        515                 520                 525
Val Leu Gly Thr Glu Ser Arg Asp Gly Pro Gly Trp Ala Gln Trp Leu
530                 535                 540
Leu Pro Pro Val Val Trp Leu Leu Asn Gly Leu Leu Val Leu Val Ser
545                 550                 555                 560
Leu Val Leu Leu Phe Val Tyr Gly Glu Pro Val Thr Arg Pro His Ser
                565                 570                 575
Gly Pro Ala Val Tyr Phe Trp Arg His Arg Lys Gln Ala Asp Leu Asp
            580                 585                 590
Leu Ala Arg Gly Asp Phe Ala Gln Ala Gln Gln Leu Trp Leu Ala
        595                 600                 605
Leu Arg Ala Leu Gly Arg Pro Leu Pro Thr Ser His Leu Asp Leu Ala
610                 615                 620
Cys Ser Leu Leu Trp Asn Leu Ile Arg His Leu Leu Gln Arg Leu Trp
```

```
             625                 630                 635                 640
Val Gly Arg Trp Leu Ala Gly Arg Ala Gly Leu Gln Gln Asp Cys
                    645                 650                 655

Ala Leu Arg Val Asp Ala Ser Ala Ser Ala Arg Asp Ala Ala Leu Val
                    660                 665                 670

Tyr His Lys Leu His Gln Leu His Thr Met Gly Lys His Thr Gly Gly
                675                 680                 685

His Leu Thr Ala Thr Asn Leu Ala Leu Ser Ala Leu Asn Leu Ala Glu
    690                 695                 700

Cys Ala Gly Asp Ala Val Ser Val Ala Thr Leu Ala Glu Ile Tyr Val
705                 710                 715                 720

Ala Ala Ala Leu Arg Val Lys Thr Ser Leu Pro Arg Ala Leu His Phe
                725                 730                 735

Leu Thr Arg Phe Phe Leu Ser Ser Ala Arg Gln Ala Cys Leu Ala Gln
                740                 745                 750

Ser Gly Ser Val Pro Pro Ala Met Gln Trp Leu Cys His Pro Val Gly
            755                 760                 765

His Arg Phe Phe Val Asp Gly Asp Trp Ser Val Leu Ser Thr Pro Trp
    770                 775                 780

Glu Ser Leu Tyr Ser Leu Ala Gly Asn Pro Val Asp Pro Leu Ala Gln
785                 790                 795                 800

Val Thr Gln Leu Phe Arg Glu His Leu Leu Glu Arg Ala Leu Asn Cys
                805                 810                 815

Val Thr Gln Pro Asn Pro Ser Pro Gly Ser Ala Asp Gly Asp Lys Glu
                820                 825                 830

Phe Ser Asp Ala Leu Gly Tyr Leu Gln Leu Leu Asn Ser Cys Ser Asp
            835                 840                 845

Ala Ala Gly Ala Pro Ala Tyr Ser Phe Ser Ile Ser Ser Met Ala
        850                 855                 860

Thr Thr Thr Gly Val Asp Pro Val Ala Lys Trp Trp Ala Ser Leu Thr
865                 870                 875                 880

Ala Val Val Ile His Trp Leu Arg Arg Asp Glu Ala Ala Glu Arg
            885                 890                 895

Leu Cys Pro Leu Val Glu His Leu Pro Arg Val Leu Gln Glu Ser Glu
                900                 905                 910

Arg Pro Leu Pro Arg Ala Ala Leu His Ser Phe Lys Ala Ala Arg Ala
            915                 920                 925

Leu Leu Gly Cys Ala Lys Ala Glu Ser Gly Pro Ala Ser Leu Thr Ile
        930                 935                 940

Cys Glu Lys Ala Ser Gly Tyr Leu Gln Asp Ser Leu Ala Thr Thr Pro
945                 950                 955                 960

Ala Ser Ser Ser Ile Asp Lys Ala Val Gln Leu Phe Leu Cys Asp Leu
                965                 970                 975

Leu Leu Val Val Arg Thr Ser Leu Trp Arg Gln Gln Pro Pro Ala
            980                 985                 990

Pro Ala Pro Ala Ala Gln Gly Thr Ser Ser Arg Pro Gln Ala Ser Ala
        995                 1000                1005

Leu Glu Leu Arg Gly Phe Gln Arg Asp Leu Ser Ser Leu Arg Arg
    1010                1015                1020

Leu Ala Gln Ser Phe Arg Pro Ala Met Arg Arg Val Phe Leu His
    1025                1030                1035

Glu Ala Thr Ala Arg Leu Met Ala Gly Ala Ser Pro Thr Arg Thr
    1040                1045                1050
```

```
His Gln Leu Leu Asp Arg Ser Leu Arg Arg Ala Gly Pro Gly
    1055                1060                1065

Gly Lys Gly Gly Ala Val Ala Glu Leu Glu Pro Arg Pro Thr Arg
    1070                1075                1080

Arg Glu His Ala Glu Ala Leu Leu Leu Ala Ser Cys Tyr Leu Pro
    1085                1090                1095

Pro Gly Phe Leu Ser Ala Pro Gly Gln Arg Val Gly Met Leu Ala
    1100                1105                1110

Glu Ala Ala Arg Thr Leu Glu Lys Leu Gly Asp Arg Arg Leu Leu
    1115                1120                1125

His Asp Cys Gln Gln Met Leu Met Arg Leu Gly Gly Gly Thr Thr
    1130                1135                1140

Val Thr Ser Ser
    1145

<210> SEQ ID NO 31
<211> LENGTH: 4922
<212> TYPE: DNA
<213> ORGANISM: Homo sapiens

<400> SEQUENCE: 31
agcagagctg cggccggggg aacccagttt ccgaggaact tttcgccggc gccgggccgc     60
ctctgaggcc agggcaggac acgaacgcgc ggagcggcgg cggcgactga gagccggggc    120
cgcggcggcg ctccctagga agggccgtac gaggcggcgg gcccggcggg cctcccggag    180
gaggcggctc cgccatggac gagccaccct tcagcgaggc ggctttggag caggcgctgg    240
gcgagccgtg cgatctggac gcggcgctgc tgaccgacat cgaagacatg cttcagctta    300
tcaacaacca agacagtgac ttccctggcc tatttgaccc accctatgct gggagtgggg    360
caggggggcac agaccctgcc agccccgata ccagctcccc aggcagcttg tctccacctc    420
ctgccacatt gagctcctct cttgaagcct tcctgagcgg gccgcaggca gcgccctcac    480
ccctgtcccc tccccagcct gcacccactc cattgaagat gtaccgtcc atgcccgctt    540
tctcccctgg gcctggtatc aaggaagagt cagtgccact gagcatcctg cagaccccca    600
ccccacagcc cctgccaggg gcctcctgc acagagctt cccagcccca gccccaccgc    660
agttcagctc caccctgtg ttaggctacc ccagccctcc gggaggcttc tctacaggaa    720
gccctcccgg gaacacccag cagccgctgc ctggcctgcc actggcttcc ccgccagggg    780
tcccgcccgt ctccttgcac acccaggtcc agagtgtggt ccccccagcag ctactgacag    840
tcacagctgc ccccacggca gcccctgtaa cgaccactgt gacctcgcag atccagcagg    900
tcccggtcct gctgcagccc cacttcatca aggcagactc gctgcttctg acagccatga    960
agacagacgg agccactgtg aaggcggcag gtctcagtcc cctggtctct ggcaccactg   1020
tgcagacagg gcctttgccg accctggtga gtggcgaaac catcttggca acagtcccac   1080
tggtcgtaga tgcggagaag ctgcctatca accggctcgc agctggcagc aaggccccgg   1140
cctctgccca gagccgtgga gagaagcgca cagcccacaa cgccattgag aagcgctacc   1200
gctcctccat caatgacaaa atcattgagc tcaaggatct ggtggtgggc actgaggcaa   1260
agctgaataa atctgctgtc ttgcgcaagg ccatcgacta cattcgcttt ctgcaacaca   1320
gcaaccagaa actcaagcag gagaacctaa gtctgcgcac tgctgtccac aaaaagcaaat   1380
ctctgaagga tctggtgtcg gcctgtggca gtggagggaa cacagacgtg ctcatggagg   1440
gcgtgaagac tgaggtggag gacacactga ccccaccccc ctcggatgct ggctcacctt   1500
```

-continued

```
tccagagcag ccccttgtcc cttggcagca ggggcagtgg cagcggtggc agtggcagtg      1560
actcggagcc tgacagccca gtctttgagg acagcaaggc aaagccagag cagcggccgt      1620
ctctgcacag ccggggcatg ctggaccgct cccgcctggc cctgtgcacg ctcgtcttcc      1680
tctgcctgtc ctgcaacccc ttggcctcct tgctgggggc ccgggggctt ccagccccct      1740
cagataccac cagcgtctac catagccctg ggcgcaacgt gctgggcacc gagagcagag      1800
atggccctgg ctgggcccag tggctgctgc ccccagtggc tggctgctc aatgggctgt       1860 tggtgctcgt ctccttggtg cttctctttg tctacggtga gccagtcaca cggccccact      1920
caggccccgc cgtgtacttc tggaggcatc gcaagcaggc tgacctggac ctggcccggg      1980
gagactttgc ccaggctgcc cagcagctgt ggctggccct gcgggcactg gccggcccc       2040 tgcccacctc ccacctggac ctggcttgta gcctcctctg gaacctcatc cgtcacctgc      2100
tgcagcgtct ctgggtgggc cgctggctgg caggccgggc aggggggcctg cagcaggact     2160 gtgctctgcg agtggatgct agcgccagcc ccgagacgc agcccctggtc taccataagc     2220 tgcaccagct gcacaccatg gggaagcaca caggcgggca cctcactgcc accaacctgg      2280
cgctgagtgc cctgaacctg gcagagtgtg caggggatgc cgtgtctgtg gcgacgctgg     2340
ccgagatcta tgtggcggct gcattgagag tgaagaccag tctcccacgg gccttgcatt      2400
ttctgacacg cttcttcctg agcagtgccc gccaggcctg cctggcacag agtggctcag      2460
tgcctcctgc catgcagtgg ctctgccacc ccgtgggcca ccgtttcttc gtggatgggg     2520
actggtccgt gctcagtacc ccatgggaga gcctgtacag cttggcgg aacccagtgg       2580 accccctggc ccaggtgact cagctattcc gggaacatct cttagagcga gcactgaact      2640
gtgtgaccca gcccaacccc agccctgggt cagctgatgg ggacaaggaa ttctcggatg      2700
ccctcgggta cctgcagctg ctgaacagct gttctgatgc tgcgggggct cctgcctaca     2760
gcttctccat cagttccagc atggccacca ccaccggcgt agaccccgtg ccaagtggt       2820 gggcctctct gacagctgtg gtgatccact ggctgcggcg ggatgaggag gcggctgagc     2880
ggctgtgccc gctggtggag cacctgcccc gggtgctgca ggagtctgag agacccctgc     2940
ccagggcagc tctgcactcc ttcaaggctg cccgggccct gctgggctgt gccaaggcag      3000
agtctggtcc agccagcctg accatctgtg agaaggccag tgggtacctg caggacagcc      3060
tggctaccac accagccagc agctccattg acaaggccgt gcagctgttc ctgtgtgacc     3120
tgcttcttgt ggtgcgcacc agcctgtggc ggcagcagca gccccggcc ccggccccag      3180 cagcccaggg caccagcagc aggccccagg cttccgccct tgagctgcgt ggcttccaac      3240
gggacctgag cagcctgagg cggctggcac agagcttccg gcccgccatg cggagggtgt      3300
tcctacatga ggccacggcc cggctgatgg cggggccag cccacacgg acacaccagc        3360 tcctcgaccg cagtctgagg cggcgggcag gccccggtgg caaaggaggc gcggtggcgg      3420
agctggagcc gcgccacg cggcgggagc acgcggaggc cttgctgctg gcctcctgct       3480
acctgccccc cggcttcctg tcggcgcccg ggcagcgcgt gggcatgctg gctgaggcgg      3540
cgcgcacact cgagaagctt ggcgatcgcc ggctgctgca cgactgtcag cagatgctca     3600
tgcgcctggg cggtgggacc actgtcactt ccagctagac cccgtgtccc cggcctcagc      3660
acccctgtct ctagccactt tggtcccgtg cagcttctgt cctgcgtcga agctttgaag      3720
gccgaaggca gtgcaagaga ctctggcctc cacagttcga cctgcggctg ctgtgtgcct      3780
tcgcggtgga aggcccgagg ggcgcgatct tgaccctaag accggcggcc atgatggtgc      3840
```

-continued

| | |
|---|---|
| tgacctctgg tggccgatcg gggcactgca ggggccgagc catttttgggg ggccccctc | 3900 |
| cttgctctgc aggcacctta gtggctttttt tcctcctgtg tacagggaag agagggtac | 3960 |
| atttccctgt gctgacggaa gccaacttgg cttttcccgga ctgcaagcag ggctctgccc | 4020 |
| cagaggcctc tctctccgtc gtgggagaga gacgtgtaca tagtgtaggt cagcgtgctt | 4080 |
| agcctcctga cctgaggctc ctgtgctact ttgccttttg caaactttat tttcatagat | 4140 |
| tgagaagttt tgtacagaga attaaaaatg aaattattta taatctgggt tttgtgtctt | 4200 |
| cagctgatgg atgtgctgac tagtgagagt gcttgggccc tcccccagca cctagggaaa | 4260 |
| ggcttcccct cccctccgg ccacaaggta cacaactttt aacttagctc ttcccgatgt | 4320 |
| ttgtttgtta gtgggaggag tggggagggc tggctgtatg gcctccagcc tacctgttcc | 4380 |
| ccctgctccc agggcacatg gttgggctgt gtcaacccct agggcctcca tgggggtcagt | 4440 |
| tgtcccttct cacctcccag ctctgtcccc atcaggtccc tgggtggcac gggaggatgg | 4500 |
| actgacttcc aggacctgtt gtgtgacagg agctacagct tgggtctccc tgcaagaagt | 4560 |
| ctggcacgtc tcacctcccc catcccggcc cctggtcatc tcacagcaaa gaagcctcct | 4620 |
| ccctcccgac ctgccgccac actggagagg gggcacaggg gcgggggagg tttcctgttc | 4680 |
| tgtgaaaggc cgactccctg actccattca tgccccccc cccagcccct cccttcattc | 4740 |
| ccattcccca acctaaagcc tggcccggct cccagctgaa tctggtcgga tccacgggc | 4800 |
| tgcagatttt ccaaaacaat cgttgtatct ttattgactt tttttttttt tttttctga | 4860 |
| atgcaatgac tgtttttac tcttaaggaa aataaacatc ttttagaaac aaaaaaaaa | 4920 |
| aa | 4922 |

<210> SEQ ID NO 32
<211> LENGTH: 3402
<212> TYPE: DNA
<213> ORGANISM: Cricetulus griseus

<400> SEQUENCE: 32

| | |
|---|---|
| atggacgagc tgcctttcgg tgaggcggct gtggaacagg cgctggacga gctgggcgaa | 60 |
| ctggacgccg cactgctgac cgacatccaa gacatgcttc agctcatcaa caaccaagac | 120 |
| agtgacttcc ctggcctgtt tgattccccc tatgcagggg gcggggcagg agacacagag | 180 |
| cccaccagcc ctggtgccaa ctctcctgag agcttgtctt ctcctgcttc cctgggttcc | 240 |
| tctctggaag ccttcctggg ggaacccaag gcaacacctg catccttgtc ccctgtgccg | 300 |
| tctgcatcca ctgctttaaa gatgtacccg tctgtgcccc ccttctcccc tgggcctgga | 360 |
| atcaaagaag agccagtgcc actcaccatc ctgcagcccc cagcagcaca gccatcacca | 420 |
| gggacccctcc tgcctccgag tttccctcca ccacccctgc agctcagccc ggctcctgtg | 480 |
| ctggggtatt ctagccttcc ttcaggcttc tcagggaccc ttcctggaaa tacccaacag | 540 |
| ccaccatcta gcctgtcact ggcctctgca ccaggagtct cgcccatctc tttacacacc | 600 |
| caggtccaga gctcagcctc ccagcagcca ctgccagcct aacagccccc tagaacaacc | 660 |
| actgtgacct cacagatcca gcgggtccca gtcgtactgc agccacattt catcaaggca | 720 |
| gattcactgc tactgacaac tgtaaaaaca gatacaggag ccacgatgaa gacggctggc | 780 |
| atcagtacct tagcccctgg cacagccgtg caggcaggcc cttgcagac cctggtgagt | 840 |
| ggtgggacca tcctggccac agtaccattg gttgtggata cagacaaact gcccatccat | 900 |
| cgactggcag ctggcagcaa ggccctgggc tcagctcaga gccgtggtga aagcgcaca | 960 |
| gcccacaatg ccattgagaa gcgctaccgt tcctctatca atgacaagat tgtggagctc | 1020 |

```
aaagacctgg tggtgggcac tgaggcaaag ctgaataaat ctgccgtctt gcgcaaggcc      1080
atcgactata tccgcttctt acagcacagc aaccagaagc tcaagcagga gaacctggcc      1140
ctgcgaaatg ccgctcacaa aagcaaatcc ctgaaggacc tggtgtcggc ctgtggcagt      1200
gcaggaggca cagatgtggc tatggagggt gtgaagcctg aggtggtgga tacgctgacc      1260
cctccaccct cagacgctgg ctcgccctcc cagagtagcc ccttgtccct cggcagcaga      1320
ggtagcagca gtggtggcag tgactcggag cctgacagcc cagtctttga ggatagccag      1380
gtgaaagccc aacggctgca cagtcatggc atgctggacc gctcccgcct agccctgtgt      1440
gcgctggtct tcctgtgtct gacctgcaac cccttggcat cactgtttgg ctggggcatc      1500
cccggtccct ccagtgcctc tggtgcacac acagctctg ggcgtagcat gctggaggcc      1560
gagagcagag atggctctaa ttggacccag tggttgctgc caccctagt ctggctggcc      1620 aatggactac tagtgttggc ctgcctggct cttctctttg tctatgggga acctgtgacc      1680
cggccacaca ctagcccagc tgtacacttc tggagacatc gcaaacaggc tgacctggac      1740
ttggctcggg gagattttgc ccaggctgct cagcagctgt ggctggccct gcaggcattg      1800
ggacggcccc tgcccacctc gaacctagac ttggcctgca gcctgctttg gaacctcatc      1860
cgccacctgc tgcagcgtct ctgggttggc cgctggctgg caggccgggc tggggggcttg     1920 cggagagact gtggactgag aatggatgca cgtgccagtg ctcgagatgc ggctctcgtc      1980
taccataagc tgcaccagct gcatgccatg gcaaataca caggagggca cctcattgct      2040
tctaacctgg cactgagtgc cctgaacctg gccgagtgcg caggagatgc tgtatccatg      2100
gcaacgctgg cagagatcta tgtggctgct gccctgaggg tcaagaccag tctcccaaga      2160
gccttgcact ttttgacacg tttcttcctg agtagtgccc gccaggcctg cctggcacag      2220
agtggctcag tgcctcttgc catgcagtgg ctctgccacc ctgtaggcca ccgtttcttc      2280
gtggatgggg actgggctgt gcatggtgcc ccacaggaga gcctgtacag cgtggctggg      2340
aacccagtgg atccctcgc ccaggtgact cgactattct gcgaacatct cttggagaga      2400
gcactgaact gtattgctca acccagcccg gggacagctg atggagacag ggagttctct      2460
gacgcacttg gatacctgca gttgctaaat cgctgctctg atgctgtcgg gactcctgcc      2520
tgcagcttct ctgtcagctc cagcatggct tccaccaccg gcacagaccc agtggccaag      2580
tggtgggcct cactgacggc tgtggtgatc cactggctgc ggcgggatga agaggcagct      2640
gagcgcctat acccgctggt agagcgtatg ccccacgtgc tgcaggagac tgagagaccc      2700
ctgcccaagg cagctctgta ctccttcaag gctgcccggg ctctgctgga ccacagaaaa      2760
gtggagtctg gcccagccag cctggccatc tgtgagaagg ccagcgggta cttgcgggac      2820
agcttagccg ctccaccaac tggcagctcc attgacaagg ccatgcagct gctcctgtgt      2880
gatctacttc ttgtggcccg cactagtatg tggcagcgcc agcagtcacc agcctcagcc      2940
caggtagctc acagtgccag caatggatct caggcctccg ctttggagct tcgaggtttc      3000
caacaggacc tgagcagcct gaggcgcttg gcacagaact tccggcctgc tatgaggaga      3060
gtgttcctac acgaggccac agctcggctg atggcagggg caagtcctgc ccggacacac      3120
cagctcctgg accgaagtct gcggaggcgg gccggctcca gtggcaaagg aggcactgta      3180
gctgagctgg agcctcgacc cacatggcgg gagcacacag aggccttgct gctggcctcc      3240
tgctatctgc cacctgcctt cctgtcgcc cctggacagc aaatgagcat gttggctgag      3300
gcagcacgca ctgtagagaa gcttggtgat catcggctac tgcttgactg ccagcagatg      3360
```
cttctgcgcc tgggcggtgg gaccactgtc acttccagct aa            3402

<210> SEQ ID NO 33
<211> LENGTH: 3816
<212> TYPE: DNA
<213> ORGANISM: Cricetulus griseus

<400> SEQUENCE: 33
ctcctgcgaa gcctggcggg cgccgccgcc atggacgagc tgcctttcgg tgaggcggct      60
gtggaacagg cgctggacga gctgggcgaa ctggacgccg cactgctgac cgacatccaa     120
gacatgcttc agctcatcaa caaccaagac agtgacttcc ctggcctgtt tgattccccc     180
tatgcagggg gcggggcagg agacacagag cccaccagcc ctggtgccaa ctctcctgag     240
agcttgtctt ctcctgcttc cctgggttcc tctctggaag ccttcctggg ggaacccaag     300
gcaacacctg catccttgtc ccctgtgccg tctgcatcca ctgctttaaa gatgtacccg     360
tctgtgcccc ccttctcccc tgggcctgga atcaaagaag agccagtgcc actcaccatc     420
ctgcagcccc cagcagcaca gccatcacca gggaccctcc tgcctccgag tttccctcca     480
ccacccctgc agctcagccc ggctcctgtg ctggggtatt ctagccttcc ttcaggcttc     540
tcagggaccc ttcctggaaa tacccaacag ccaccatcta gcctgtcact ggcctctgca     600
ccaggagtct cgcccatctc tttacacacc caggtccaga gctcagcctc ccagcagcca     660
ctgccagcct caacagcccc tagaacaacc actgtgacct cacagatcca gcgggtccca     720
gtcgtactgc agccacattt catcaaggca gattcactgc tactgacaac tgtaaaaaca     780
gatacaggag ccacgatgaa gacggctggc atcagtacct tagcccctgg cacagccgtg     840
caggcaggcc ccttgcagac cctggtgagt ggtgggacca tcctggccac agtaccattg     900
gttgtggata cagacaaact gcccatccat cgactggcag ctggcagcaa ggccctgggc     960
tcagctcaga gccgtggtga agcgcacaca gcccacaatg ccattgagaa gcgctaccgt    1020
tcctctatca atgacaagat tgtggagctc aaagacctgg tggtgggcac tgaggcaaag    1080
ctgaataaat ctgccgtctt gcgcaaggcc atcgactata tccgcttctt acagcacagc    1140
aaccagaagc tcaagcagga gaacctggcc tgcgaaatgc cgctcacaa aagcaaatcc    1200
ctgaaggacc tggtgtcggc ctgtggcagt gcaggaggca cagatgtggc tatggagggt    1260
gtgaagcctg aggtggtgga tacgctgacc cctccaccct cagacgctgg ctcgccctcc    1320
cagagtagcc ccttgtccct cggcagcaga ggtagcagca gtggtggcag tgactcggag    1380
cctgacagcc cagtctttga ggatagccag gtgaaagccc aacggctgca cagtcatggc    1440
atgctggacc gctcccgcct agccctgtgt gcgctggtct tcctgtgtct gacctgcaac    1500
cccttggcat cactgtttgg ctggggcatc cccggtccct ccagtgcctc tggtgcacac    1560
cacagctctg ggcgtagcat gctggaggcc gagagcagag atggctctaa ttggacccag    1620
tggttgctgc caccctagt ctggctggcc aatggactac tagtgttggc ctgcctggct    1680
cttctctttg tctatgggga acctgtgacc cggccacaca ctagcccagc tgtacacttc    1740
tggagacatc gcaaacaggc tgacctggac ttggctcggg gagattttgc ccaggctgct    1800
cagcagctgt ggctggccct gcaggcattg gacggccccc tgcccacctc gaacctagac    1860
ttggcctgca gcctgctttg gaacctcatc cgccacctgc tgcagcgtct ctgggttggc    1920
cgctggctgg caggccgggc tgggggcttg cggagagact gtggactgag aatggatgca    1980
cgtgccagtg ctcgagatgc ggctctcgtc taccataagc tgcaccagct gcatgccatg    2040
ggcaaataca caggagggca cctcattgct tctaacctgg cactgagtgc cctgaacctg    2100

```
gccgagtgcg caggagatgc tgtatccatg gcaacgctgg cagagatcta tgtggctgct    2160
gccctgaggg tcaagaccag tctcccaaga gccttgcact ttttgacacg tttcttcctg    2220
agtagtgccc gccaggcctg cctggcacag agtggctcag tgcctcttgc catgcagtgg    2280
ctctgccacc ctgtaggcca ccgtttcttc gtggatgggg actgggctgt gcatggtgcc    2340
ccacaggaga gcctgtacag cgtggctggg aacccagtgg atcccctcgc ccaggtgact    2400
cgactattct gcgaacatct cttggagaga gcactgaact gtattgctca acccagcccg    2460
gggacagctg atggagacag ggagttctct gacgcacttg gatacctgca gttgctaaat    2520
cgctgctctg atgctgtcgg gactcctgcc tgcagcttct ctgtcagctc agcatggct    2580 tccaccaccg gcacagaccc agtggccaag tggtgggcct cactgacggc tgtggtgatc    2640
cactggctgc ggcgggatga agaggcagct gagcgcctat accgctggt agagcgtatg    2700 ccccacgtgc tgcaggagac tgagagaccc ctgcccaagg cagctctgta ctccttcaag    2760
gctgcccggg ctctgctgga ccacagaaaa gtggagtctg gcccagccag cctggccatc    2820
tgtgagaagg ccagcgggta cttgcgggac agcttagccg ctccaccaac tggcagctcc    2880
attgacaagg ccatgcagct gctcctgtgt gatctacttc ttgtggcccg cactagtatg    2940
tggcagcgcc agcagtcacc agcctcagcc caggtagctc acagtgccag caatggatct    3000
caggcctccg ctttggagct tcgaggtttc aacaggacc tgagcagcct gaggcgcttg    3060
gcacagaact tccggcctgc tatgaggaga gtgttcctac acgaggccac agctcggctg    3120
atggcagggg caagtcctgc ccggacacac cagctcctgg accgaagtct gcggaggcgg    3180
gccggctcca gtggcaaagg aggcactgta gctgagctgg agcctcgacc cacatggcgg    3240
gagcacacag aggccttgct gctggcctcc tgctatctgc cacctgcctt cctgtcggcc    3300
cctggacagc aaatgagcat gttggctgag gcagcacgca ctgtagagaa gcttggtgat    3360
catcggctac tgcttgactg ccagcagatg cttctgcgcc tgggcggtgg gaccactgtc    3420
acttccagct aaaccttgga tggtctcccc agtattagag gcccttaagg acctttgtca    3480
ctggctgtgg tcgtccagag agggtgagcc tgacaagcaa tcaggatcat gccgacctct    3540
agtgacaaat ctagaaattg cagaggctgc actggcccaa tgccaccctc ttgctctgta    3600 ggcaccttt tcctgtccta tggaaaggaa ccttccccct agctgagggc caccctgtcc    3660
tgaggctctc acccactcct ggaagacttg tatatagtgt agatccagct gagccagttt    3720
cctgtgcagg ctcatgtact actttaactt ttgcaaactt tattttcata ggttgagaaa    3780
ttttgtacag aaaattaaaa agtgaaatta tttata                              3816
```

<210> SEQ ID NO 34
<211> LENGTH: 1133
<212> TYPE: PRT
<213> ORGANISM: Cricetulus griseus

<400> SEQUENCE: 34

```
Met Asp Glu Leu Pro Phe Gly Glu Ala Ala Val Glu Gln Ala Leu Asp
1               5                   10                  15

Glu Leu Gly Glu Leu Asp Ala Ala Leu Leu Thr Asp Ile Gln Asp Met
            20                  25                  30

Leu Gln Leu Ile Asn Asn Gln Asp Ser Asp Phe Pro Gly Leu Phe Asp
        35                  40                  45

Ser Pro Tyr Ala Gly Gly Gly Ala Gly Asp Thr Glu Pro Thr Ser Pro
    50                  55                  60
```

-continued

Gly Ala Asn Ser Pro Glu Ser Leu Ser Ser Pro Ala Ser Leu Gly Ser
 65                  70                  75                  80

Ser Leu Glu Ala Phe Leu Gly Glu Pro Lys Ala Thr Pro Ala Ser Leu
                 85                  90                  95

Ser Pro Val Pro Ser Ala Ser Thr Ala Leu Lys Met Tyr Pro Ser Val
            100                 105                 110

Pro Pro Phe Ser Pro Gly Pro Gly Ile Lys Glu Pro Val Pro Leu
        115                 120                 125

Thr Ile Leu Gln Pro Pro Ala Ala Gln Pro Ser Pro Gly Thr Leu Leu
    130                 135                 140

Pro Pro Ser Phe Pro Pro Pro Leu Gln Leu Ser Pro Ala Pro Val
145                 150                 155                 160

Leu Gly Tyr Ser Ser Leu Pro Ser Gly Phe Ser Gly Thr Leu Pro Gly
                165                 170                 175

Asn Thr Gln Gln Pro Pro Ser Ser Leu Ser Leu Ala Ser Ala Pro Gly
            180                 185                 190

Val Ser Pro Ile Ser Leu His Thr Gln Val Gln Ser Ser Ala Ser Gln
            195                 200                 205

Gln Pro Leu Pro Ala Ser Thr Ala Pro Arg Thr Thr Thr Val Thr Ser
210                 215                 220

Gln Ile Gln Arg Val Pro Val Val Leu Gln Pro His Phe Ile Lys Ala
225                 230                 235                 240

Asp Ser Leu Leu Leu Thr Thr Val Lys Thr Asp Thr Gly Ala Thr Met
                245                 250                 255

Lys Thr Ala Gly Ile Ser Thr Leu Ala Pro Gly Thr Ala Val Gln Ala
                260                 265                 270

Gly Pro Leu Gln Thr Leu Val Ser Gly Gly Thr Ile Leu Ala Thr Val
            275                 280                 285

Pro Leu Val Val Asp Thr Asp Lys Leu Pro Ile His Arg Leu Ala Ala
        290                 295                 300

Gly Ser Lys Ala Leu Gly Ser Ala Gln Ser Arg Gly Glu Lys Arg Thr
305                 310                 315                 320

Ala His Asn Ala Ile Glu Lys Arg Tyr Arg Ser Ser Ile Asn Asp Lys
                325                 330                 335

Ile Val Glu Leu Lys Asp Leu Val Val Gly Thr Glu Ala Lys Leu Asn
                340                 345                 350

Lys Ser Ala Val Leu Arg Lys Ala Ile Asp Tyr Ile Arg Phe Leu Gln
            355                 360                 365

His Ser Asn Gln Lys Leu Lys Gln Glu Asn Leu Ala Leu Arg Asn Ala
    370                 375                 380

Ala His Lys Ser Lys Ser Leu Lys Asp Leu Val Ser Ala Cys Gly Ser
385                 390                 395                 400

Ala Gly Gly Thr Asp Val Ala Met Glu Gly Val Lys Pro Glu Val Val
                405                 410                 415

Asp Thr Leu Thr Pro Pro Ser Asp Ala Gly Ser Pro Ser Gln Ser
            420                 425                 430

Ser Pro Leu Ser Leu Gly Ser Arg Gly Ser Ser Ser Gly Gly Ser Asp
            435                 440                 445

Ser Glu Pro Asp Ser Pro Val Phe Glu Asp Ser Gln Val Lys Ala Gln
        450                 455                 460

Arg Leu His Ser His Gly Met Leu Asp Arg Ser Arg Leu Ala Leu Cys
465                 470                 475                 480

Ala Leu Val Phe Leu Cys Leu Thr Cys Asn Pro Leu Ala Ser Leu Phe

-continued

```
                485                 490                 495
Gly Trp Gly Ile Pro Gly Pro Ser Ser Ala Gly Ala His His Ser
            500                 505                 510

Ser Gly Arg Ser Met Leu Glu Ala Glu Ser Arg Asp Gly Ser Asn Trp
            515                 520                 525

Thr Gln Trp Leu Leu Pro Pro Leu Val Trp Leu Ala Asn Gly Leu Leu
        530                 535                 540

Val Leu Ala Cys Leu Ala Leu Leu Phe Val Tyr Gly Glu Pro Val Thr
545                 550                 555                 560

Arg Pro His Thr Ser Pro Ala Val His Phe Trp Arg His Arg Lys Gln
                565                 570                 575

Ala Asp Leu Asp Leu Ala Arg Gly Asp Phe Ala Gln Ala Ala Gln Gln
            580                 585                 590

Leu Trp Leu Ala Leu Gln Ala Leu Gly Arg Pro Leu Pro Thr Ser Asn
        595                 600                 605

Leu Asp Leu Ala Cys Ser Leu Leu Trp Asn Leu Ile Arg His Leu Leu
    610                 615                 620

Gln Arg Leu Trp Val Gly Arg Trp Leu Ala Gly Arg Ala Gly Gly Leu
625                 630                 635                 640

Arg Arg Asp Cys Gly Leu Arg Met Asp Ala Arg Ala Ser Ala Arg Asp
                645                 650                 655

Ala Ala Leu Val Tyr His Lys Leu His Gln Leu His Ala Met Gly Lys
            660                 665                 670

Tyr Thr Gly Gly His Leu Ile Ala Ser Asn Leu Ala Leu Ser Ala Leu
        675                 680                 685

Asn Leu Ala Glu Cys Ala Gly Asp Ala Val Ser Met Ala Thr Leu Ala
    690                 695                 700

Glu Ile Tyr Val Ala Ala Ala Leu Arg Val Lys Thr Ser Leu Pro Arg
705                 710                 715                 720

Ala Leu His Phe Leu Thr Arg Phe Phe Leu Ser Ser Ala Arg Gln Ala
                725                 730                 735

Cys Leu Ala Gln Ser Gly Ser Val Pro Leu Ala Met Gln Trp Leu Cys
            740                 745                 750

His Pro Val Gly His Arg Phe Phe Val Asp Gly Asp Trp Ala Val His
        755                 760                 765

Gly Ala Pro Gln Glu Ser Leu Tyr Ser Val Ala Gly Asn Pro Val Asp
    770                 775                 780

Pro Leu Ala Gln Val Thr Arg Leu Phe Cys Glu His Leu Leu Glu Arg
785                 790                 795                 800

Ala Leu Asn Cys Ile Ala Gln Pro Ser Pro Gly Thr Ala Asp Gly Asp
                805                 810                 815

Arg Glu Phe Ser Asp Ala Leu Gly Tyr Leu Gln Leu Leu Asn Arg Cys
            820                 825                 830

Ser Asp Ala Val Gly Thr Pro Ala Cys Ser Phe Ser Val Ser Ser Ser
        835                 840                 845

Met Ala Ser Thr Thr Gly Thr Asp Pro Val Ala Lys Trp Trp Ala Ser
    850                 855                 860

Leu Thr Ala Val Val Ile His Trp Leu Arg Arg Asp Glu Glu Ala Ala
865                 870                 875                 880

Glu Arg Leu Tyr Pro Leu Val Glu Arg Met Pro His Val Leu Gln Glu
                885                 890                 895

Thr Glu Arg Pro Leu Pro Lys Ala Ala Leu Tyr Ser Phe Lys Ala Ala
            900                 905                 910
```

```
Arg Ala Leu Leu Asp His Arg Lys Val Glu Ser Gly Pro Ala Ser Leu
        915                 920                 925

Ala Ile Cys Glu Lys Ala Ser Gly Tyr Leu Arg Asp Ser Leu Ala Ala
        930                 935                 940

Pro Pro Thr Gly Ser Ser Ile Asp Lys Ala Met Gln Leu Leu Leu Cys
945                 950                 955                 960

Asp Leu Leu Val Ala Arg Thr Ser Met Trp Gln Arg Gln Ser
        965                 970                 975

Pro Ala Ser Ala Gln Val Ala His Ser Ala Ser Asn Gly Ser Gln Ala
        980                 985                 990

Ser Ala Leu Glu Leu Arg Gly Phe Gln Gln Asp Leu Ser Ser Leu Arg
        995                 1000                1005

Arg Leu Ala Gln Asn Phe Arg Pro Ala Met Arg Arg Val Phe Leu
    1010                1015                1020

His Glu Ala Thr Ala Arg Leu Met Ala Gly Ala Ser Pro Ala Arg
    1025                1030                1035

Thr His Gln Leu Leu Asp Arg Ser Leu Arg Arg Ala Gly Ser
    1040                1045                1050

Ser Gly Lys Gly Gly Thr Val Ala Glu Leu Glu Pro Arg Pro Thr
    1055                1060                1065

Trp Arg Glu His Thr Glu Ala Leu Leu Leu Ala Ser Cys Tyr Leu
    1070                1075                1080

Pro Pro Ala Phe Leu Ser Ala Pro Gly Gln Gln Met Ser Met Leu
    1085                1090                1095

Ala Glu Ala Ala Arg Thr Val Glu Lys Leu Gly Asp His Arg Leu
    1100                1105                1110

Leu Leu Asp Cys Gln Gln Met Leu Leu Arg Leu Gly Gly Gly Thr
    1115                1120                1125

Thr Val Thr Ser Ser
    1130

<210> SEQ ID NO 35
<211> LENGTH: 1233
<212> TYPE: DNA
<213> ORGANISM: Cricetulus griseus

<400> SEQUENCE: 35
atggacgagc tgcctttcgg tgaggcggct gtggaacagg cgctggacga gctgggcgaa      60
ctggacgccg cactgctgac cgacatccaa gacatgcttc agctcatcaa caaccaagac     120
agtgacttcc ctggcctgtt tgattccccc tatgcagggg gcggggcagg agacacagag     180
cccaccagcc ctggtgccaa ctctcctgag agcttgtctt ctcctgcttc cctgggttcc     240
tctctggaag ccttcctggg ggaacccaag gcaacacctg catccttgtc ccctgtgccg     300
tctgcatcca ctgctttaaa gatgtacccg tctgtgcccc ccttctcccc tgggcctgga     360
atcaaagaag agccagtgcc actcaccatc ctgcagcccc agcagcaca gccatcacca     420 gggaccctcc tgcctccgag tttccctcca ccacccctgc agctcagccc ggctcctgtg     480
ctggggtatt ctagccttcc ttcaggcttc tcagggaccc ttcctggaaa tacccaacag     540
ccaccatcta gcctgtcact ggcctctgca ccaggagtct cgcccatctc tttacacacc     600
caggtccaga gctcagcctc ccagcagcca ctgccagcct caacagcccc tagaacaacc     660
actgtgacct cacagatcca gcgggtccca gtcgtactgc agcccacattt catcaaggca     720 gattcactgc tactgacaac tgtaaaaaca gatacaggag ccacgatgaa gacggctggc     780
```

```
atcagtacct tagcccctgg cacagccgtg caggcaggcc ccttgcagac cctggtgagt    840
ggtgggacca tcctggccac agtaccattg gttgtggata cagacaaact gcccatccat    900
cgactggcag ctggcagcaa ggccctgggc tcagctcaga gccgtggtga gaagcgcaca    960
gcccacaatg ccattgagaa cgctaccgt tcctctatca atgacaagat tgtggagctc    1020
aaagacctgg tggtgggcac tgaggcaaag ctgaataaat ctgccgtctt gcgcaaggcc    1080
atcgactata tccgcttctt acagcacagc aaccagaagc tcaagcagga gaacctggcc    1140
ctgcgaaatg ccgctcacaa aagcaaatcc ctgaaggacc tggtgtcggc ctgtggcagt    1200
gcaggaggca cagatgtggc tatggagggt gtg                                 1233
```

```
<210> SEQ ID NO 36
<211> LENGTH: 411
<212> TYPE: PRT
<213> ORGANISM: Cricetulus griseus

<400> SEQUENCE: 36

Met Asp Glu Leu Pro Phe Gly Glu Ala Ala Val Glu Gln Ala Leu Asp
1               5                   10                  15

Glu Leu Gly Glu Leu Asp Ala Ala Leu Leu Thr Asp Ile Gln Asp Met
            20                  25                  30

Leu Gln Leu Ile Asn Asn Gln Asp Ser Asp Phe Pro Gly Leu Phe Asp
        35                  40                  45

Ser Pro Tyr Ala Gly Gly Ala Gly Asp Thr Glu Pro Thr Ser Pro
    50                  55                  60

Gly Ala Asn Ser Pro Glu Ser Leu Ser Ser Pro Ala Ser Leu Gly Ser
65                  70                  75                  80

Ser Leu Glu Ala Phe Leu Gly Glu Pro Lys Ala Thr Pro Ala Ser Leu
                85                  90                  95

Ser Pro Val Pro Ser Ala Ser Thr Ala Leu Lys Met Tyr Pro Ser Val
            100                 105                 110

Pro Pro Phe Ser Pro Gly Pro Gly Ile Lys Glu Glu Pro Val Pro Leu
        115                 120                 125

Thr Ile Leu Gln Pro Pro Ala Ala Gln Pro Ser Pro Gly Thr Leu Leu
    130                 135                 140

Pro Pro Ser Phe Pro Pro Pro Leu Gln Leu Ser Pro Ala Pro Val
145                 150                 155                 160

Leu Gly Tyr Ser Ser Leu Pro Ser Gly Phe Ser Gly Thr Leu Pro Gly
                165                 170                 175

Asn Thr Gln Gln Pro Pro Ser Ser Leu Ser Leu Ala Ser Ala Pro Gly
            180                 185                 190

Val Ser Pro Ile Ser Leu His Thr Gln Val Gln Ser Ser Ala Ser Gln
        195                 200                 205

Gln Pro Leu Pro Ala Ser Thr Ala Pro Arg Thr Thr Val Thr Ser
    210                 215                 220

Gln Ile Gln Arg Val Pro Val Val Leu Gln Pro His Phe Ile Lys Ala
225                 230                 235                 240

Asp Ser Leu Leu Leu Thr Thr Val Lys Thr Asp Thr Gly Ala Thr Met
                245                 250                 255

Lys Thr Ala Gly Ile Ser Thr Leu Ala Pro Gly Thr Ala Val Gln Ala
            260                 265                 270

Gly Pro Leu Gln Thr Leu Val Ser Gly Gly Thr Ile Leu Ala Thr Val
        275                 280                 285
```

-continued

| | | | | | | | | | | | | | | |
|---|---|---|---|---|---|---|---|---|---|---|---|---|---|---|
| Pro | Leu | Val | Val | Asp | Thr | Asp | Lys | Leu | Pro | Ile | His | Arg | Leu | Ala | Ala |
| | 290 | | | | 295 | | | | | 300 | | | | | |
| Gly | Ser | Lys | Ala | Leu | Gly | Ser | Ala | Gln | Ser | Arg | Gly | Glu | Lys | Arg | Thr |
| 305 | | | | | 310 | | | | | 315 | | | | | 320 |
| Ala | His | Asn | Ala | Ile | Glu | Lys | Arg | Tyr | Arg | Ser | Ser | Ile | Asn | Asp | Lys |
| | | | | 325 | | | | | 330 | | | | | 335 | |
| Ile | Val | Glu | Leu | Lys | Asp | Leu | Val | Val | Gly | Thr | Glu | Ala | Lys | Leu | Asn |
| | | | 340 | | | | | 345 | | | | | 350 | | |
| Lys | Ser | Ala | Val | Leu | Arg | Lys | Ala | Ile | Asp | Tyr | Ile | Arg | Phe | Leu | Gln |
| | | 355 | | | | | 360 | | | | | 365 | | | |
| His | Ser | Asn | Gln | Lys | Leu | Lys | Gln | Glu | Asn | Leu | Ala | Leu | Arg | Asn | Ala |
| | 370 | | | | | 375 | | | | | 380 | | | | |
| Ala | His | Lys | Ser | Lys | Ser | Leu | Lys | Asp | Leu | Val | Ser | Ala | Cys | Gly | Ser |
| 385 | | | | | 390 | | | | | 395 | | | | | 400 |
| Ala | Gly | Gly | Thr | Asp | Val | Ala | Met | Glu | Gly | Val | | | | | |
| | | | | 405 | | | | | 410 | | | | | | |

MODULATION OF LIPID METABOLISM FOR PROTEIN PRODUCTION

RELATED APPLICATIONS

This application claims priority to U.S. Ser. No. 62/330,973, filed May 3, 2016, the entire contents of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 14, 2017, is named L2082-700310_SL.TXT and is 88,005 bytes in size.

FIELD OF THE INVENTION

The present disclosure relates to methods and compositions for modulating the lipid metabolism pathways of a cell and engineering cells and cell lines for production of a product, e.g., a recombinant protein.

BACKGROUND

Recombinant therapeutic proteins are commonly expressed in cell expression systems, e.g., mammalian cell expression systems. In 2014, the total number of market approved biopharmaceuticals was 212, and 56% of the therapeutic products approved for market by the FDA are produced in mammalian cell lines. However, the high cost associated with production contributes to increasing global health costs.

Moreover, next generation protein biologics (NGBs) such as next generation fusion proteins, multimeric glycoproteins, or next generation antibodies often have a complex and/or non-natural structure and are proving more difficult to express than molecules such as monoclonal antibodies. Current host cell lines have not evolved pathways for the efficient synthesis and secretion of NGBs, resulting in significantly reduced growth, low productivity and often resulting in products with poor product quality attributes. Thus, these NGBs are considered difficult to express, in which the productivity and product quality do not meet clinical and market needs.

Accordingly, there is an increasing need to develop and produce recombinant biotherapeutics rapidly, efficiently, and cost-effectively while maintaining final product quality.

SUMMARY

The present disclosure is based, in part, on the discovery that modulation of lipid metabolism pathways by overexpression of a component of one or more lipid metabolism pathways increases the productivity and product quality of a cell that produces a recombinant polypeptide product. Here, it is demonstrated that modulation of the lipid metabolism, e.g., by modulating one or more lipid metabolism pathways, can be used to engineer cells and cell-free systems that produce higher yields of products and products with improved quality. Importantly, the present disclosure features global regulation of lipid metabolism by using global regulators that modulate more than one process or pathway associated with lipid metabolism, thereby causing multiple downstream effects to achieve improved product production and quality. The methods and compositions described herein are particularly useful for improved production of recombinant products or next generation biologics (e.g., fusion proteins, bispecific or multi-format antibody molecules, multimeric proteins, and glycosylated proteins), and for development of more efficient systems for production of such products (e.g., cell lines or cell-free systems).

In one aspect, the present disclosure features a method for producing a product described herein in a cell. In an embodiment, the product is a polypeptide, e.g., a recombinant polypeptide. In one embodiment, the method comprises providing a cell comprising a modification that modulates lipid metabolism, and culturing the cell, e.g., under conditions suitable for modulation of lipid metabolism by the modification, thereby producing the product.

In another aspect, the present disclosure features a method for producing product, e.g., a polypeptide, e.g., a recombinant polypeptide, in a cell-free system comprising: providing a cell-free system comprising a modification that modulates lipid metabolism, e.g., a cell-free system derived from a cell or cell line comprising a modification that modulates lipid metabolism, and placing the cell-free system under conditions suitable for production of the product; thereby producing the product, e.g., polypeptide, e.g., recombinant polypeptide. In one embodiment, the cell-free system is derived from a cell or cell line comprising a modification that modulates lipid metabolism. In one embodiment, the cell-free system comprises one or more components, e.g., an organelle or portion of an organelle, from a cell or cell line comprising a modification that modulates lipid metabolism. In some embodiments, the modification comprises an exogenous nucleic acid encoding a lipid metabolism modulator (LMM) and wherein the cell or cell line expresses a LMM, e.g., an LMM selected from the group consisting of SREBF1, SREBF2, SCD1, SCD2, SCD3, SCD4, SCD5, or a functional fragment thereof. In some embodiments, the LMM alters one or more characteristics of a cell-free system selected from the group consisting of: increases the production, e.g., yield and rate of production, of the product, e.g., polypeptide, e.g., recombinant polypeptide (NGB) produced; and increases the quality, e.g., decreases aggregation, decreases glycosylation heterogeneity, decreases fragmentation, and increases ratio of properly folded to misfolded or unfolded product, of the product.

Examples of products that can be produced using any of the methods or compositions described herein include recombinant products, or products in which at least one portion or moiety is a result of genetic engineering. Recombinant products described herein can be useful for diagnostic or therapeutic purposes. In one embodiment, a product comprises a polypeptide, such as an antibody molecule (e.g., a bispecific or multi-format antibody molecule), a fusion protein, or a protein-conjugate; a nucleic acid molecule (e.g., a DNA or RNA molecule); or a lipid-encapsulated particle (e.g., an exosome or virus-like particle). The methods and compositions described herein may be particularly useful for products that are difficult to produce, e.g., in high quantities or with sufficient quality for commercial or therapeutic use, such as next generation biologics (e.g., fusion proteins, bispecific or multi-format antibody molecules, multimeric proteins, and glycosylated proteins). In one embodiment, a cell as described herein, e.g., for producing the product, expresses the product. In one embodiment, the cell comprises an exogenous nucleic acid that encodes a product described herein, e.g., a polypeptide selected from Table 2 or 3. Additional examples of products are described in the section titled "Products".

The modifications disclosed herein that modulate lipid metabolism include agents or molecules that increase or decrease the expression of a lipid metabolism modulator (LMM) or increase or decrease the expression or activity of a component of a lipid metabolism pathway. In one embodiment, the modification is a nucleic acid, e.g., a nucleic acid encoding a LMM or an inhibitory nucleic acid that inhibits or decreases the expression of a LMM.

In one embodiment, the modification increases expression of a LMM, and comprises an exogenous nucleic acid encoding the LMM. In one embodiment, the method comprises forming, in the cell, an exogenous nucleic acid encoding a LMM or an exogenous LMM. In one embodiment, the forming comprises introducing an exogenous nucleic acid encoding a lipid metabolism modulator. In one embodiment, the forming comprises introducing an exogenous nucleic acid which increases the expression of an endogenous nucleic acid encoding a LMM. Examples of LMMs suitable for use in any of the methods and compositions described herein are further described in the sections titled "Modulation of Lipid Metabolism" and "Lipid Metabolism Modulators".

In one embodiment, the cell comprises one or more modifications. In one embodiment, the cell comprises one, two, three, four, five, six, seven, eight, nine or ten modifications. In some embodiments, the cell comprises more than one modification. In some embodiments, the cell comprises at least two, three, four, five, six, seven, eight, nine, or ten modifications. In one embodiment, the cell comprises a one or more second modification that modulates lipid metabolism. In one embodiment, the second modification comprises a second exogenous nucleic acid encoding a second LMM, e.g., a LMM different from the LMM of the first modification. In one embodiment, the second exogenous nucleic acid and the first exogenous nucleic acid are disposed on the same nucleic acid molecule. In one embodiment, the second exogenous nucleic acid and the first exogenous nucleic acid are disposed on different nucleic acid molecules. In one embodiment, the second modification provides increased the production or improved quality of the product, as compared to a cell not having the second modification. In one embodiment, the method comprises forming, in the cell, a second exogenous nucleic acid encoding a second LMM or a second exogenous LMM. In one embodiment, the forming comprises introducing the second exogenous nucleic acid encoding a second LMM. In one embodiment, the forming comprises introducing the second exogenous nucleic acid which increases the expression of an endogenous nucleic acid encoding a LMM.

Modulating lipid metabolism by any of the methods or compositions described herein can comprise or result in altering, e.g., increasing or decreasing, any one or more of the following:

i) the expression (e.g., transcription and/or translation) of a component involved in a lipid metabolism pathway;
ii) the activity (e.g., enzymatic activity) of a component involved in a lipid metabolism pathway;
iii) the amount of lipids (e.g., phospholipids, or cholesterol) present in a cell;
iv) the amount of lipid rafts or rate of lipid raft formation;
v) the fluidity, permeability, and/or thickness of a cell membrane (e.g., a plasma membrane, a vesicle membrane, or an organelle membrane);
vi) the conversion of saturated lipids to unsaturated lipids or conversion of unsaturated lipids to saturated lipids;
vii) the amount of saturated lipids or unsaturated lipids, e.g., monounsaturated lipids;
viii) the composition of lipids in the cell to attain a favorable composition that increases ER activity;
ix) the expansion of the ER (e.g., size of the ER, the ER membrane surface, or the amounts of the proteins and lipids that constitute and/or reside within the ER);
x) the expansion of the Golgi (e.g., the number and size of the Golgi, the Golgi surface, or the number or amounts of proteins and molecules that reside within the Golgi);
xi) the amount of secretory vesicles or the formation of secretory vesicles;
xii) the amount or rate of secretion of the product;
xiii) the proliferation capacity, e.g., the proliferation rate;
xiv) culture viability or cell survival;
xv) activation of membrane receptors;
xvi) the unfolded protein response (UPR);
xvii) the yield or rate of production of the product;
xviii) the product quality (e.g., aggregation, glycosylation heterogeneity, fragmentation, proper folding or assembly, post-translational modification, or disulfide bond scrambling); and/or
xix) cell growth/proliferation or cell specific growth rate.

In such embodiments, the increase or decrease of any of the aforementioned characteristics of the cell can be determined by comparison with a cell not having a modification.

The methods and compositions described herein result in increased production of the product as compared to a cell not having the modification. An increase in production can be characterized by increased amounts, yields, or quantities of product produced by the cell and/or increased rate of production, where the rate of production is equivalent to the amount of product over time. In one embodiment, production of the product, e.g., a recombinant polypeptide, is increased by 1%, 5%, 10%, 15%, 20%, 25%, 30%, 35%, 40%, 45%, 50%, 55%, 60%, 70%, 75%, 80%, 85%, 90%, 85%, or 100%, or more e.g., as compared to the production of by a cell without modulation of the lipid metabolism; or 1-fold, 2-fold, 5-fold, 10-fold, 20-fold, 50-fold, 100-fold, e.g., as compared to the production of by a cell without modulation of the lipid metabolism.

The methods and compositions described herein can also result in improved quality of the product (i.e. product quality) as compared to a cell not having the modification. Improvements in the quality of the product (i.e. product quality) can be characterized by one or more of: aggregation (e.g., a decrease in aggregates or aggregation); proper folding or assembly (e.g., a decrease in misfolded or unfolded products; or partially assembled or disassembled products); post-translation modification (e.g., increase or decrease in glycosylation heterogeneity, higher percentage of desired or predetermined post-translational modifications); fragmentation (e.g., a decrease in fragmentation); disulfide bond scrambling (e.g., a decrease in undesired isoforms or structures due to disulfide bond scrambling). In one embodiment, the quality of the product, e.g., recombinant polypeptide, is increased, e.g., 1%, 5%, 10%, 15%, 20%, 25%, 30%, 35%, 40%, 45%, 50%, 55%, 60%, 70%, 75%, 80%, 85%, 90%, 85%, or 100%, e.g., as compared to the production of by a cell without modulation of the lipid metabolism; or by 1-fold, 2-fold, 5-fold, 10-fold, 20-fold, 50-fold, 100-fold, e.g., as compared to the quality of product produced by a cell without modulation of the lipid metabolism.

In embodiments, the method for producing a product as described herein can comprise one or more additional steps, which include, but are not limited to: introducing a modification to the cell that improves ER processing capacity (ER expansion) or secretion; obtaining the product from the cell, or a descendent of the cell, or from the medium conditioned by the cell, or a descendent of the cell; separating the product from at least one cellular or medium component; and/or analyzing the product, e.g., for activity or for the presence of a structural moiety. In one embodiment, the method further comprises a step for improving ER processing capacity (or ER expansion) by introducing a nucleic acid encoding PDI, BiP, ERO, or XBP1. In one embodiment, the method further comprises an additional step for improving secretory capacity or rate of secretion by modulating SNARE machinery or other machinery involved in the secretory pathway, e.g., by introducing a nucleic acid encoding a SNARE component.

Modulation of Lipid Metabolism

The present disclosure features methods and compositions for modulating lipid metabolism. In one embodiment, the modification results in modulating, e.g., increasing, one or more lipid metabolism pathways, which include, but are not limited to: de novo lipogenesis, fatty acid re-esterification, fatty acid saturation or desaturation, fatty acid elongation, and phospholipid biosynthesis.

The modifications described herein suitable for modulating lipid metabolism include introduction of an exogenous nucleic acid that increase or decreases the expression or activity of a component of a lipid metabolism pathway or a LMM, a LMM polypeptide, or other molecule that increases or decreases the expression or activity of a component of the lipid metabolism pathway. The present disclosure features the use of lipid metabolism modulators to modulate lipid metabolism, e.g., by increasing or decreasing expression or activity of a component associated with lipid metabolism. In an embodiment, the LMM is a global regulator described herein In one embodiment, the modification that modulates lipid metabolism results in the global regulation of lipid metabolism, e.g., by increasing or decreasing the expression or activity of a global regulator. Such global regulators are molecules that are sufficiently upstream in one or more pathways, such that it can influence multiple downstream effects, for example, increasing the expression or activity of more than one, e.g., two, three, four, five, or more, components of different lipid metabolism processes or pathways. A component of a lipid metabolism process or pathway can include, but is not limited to, an enzyme, a cofactor, or other molecule that is involved in the synthesis, degradation, elongation, or structural conformation of lipid molecules.

In one embodiment, the global regulator described herein is a transcription factor that upregulates, e.g., increases the expression, of a component of the lipid metabolism, e.g., a lipid metabolism gene product selected from Table 1. By way of example, a global regulator increases the expression of two or more lipid-associated gene products, e.g., an enzyme involved in lipid biosynthesis and an enzyme involved in the saturation level of a lipid molecule.

In any of the methods or compositions described herein, the LMM comprises any of the following: a global regulator of lipid metabolism, e.g., a transcription factor that upregulates lipid metabolism genes, or a component (e.g., an enzyme, a cofactor, or a molecule) that plays a role in the de novo lipogenesis, fatty acid re-esterification, fatty acid saturation or desaturation, fatty acid elongation, or phospholipid biosynthesis pathways.

In one embodiment, the lipid metabolism modulator comprises a transcription regulator, e.g., a transcription factor, that mediates, e.g., upregulates, the expression of a lipid metabolism gene product. Examples of lipid metabolism gene products include, but are not limited to, those provided in Table 1. a global regulator of lipid metabolism, e.g., a transcription factor that upregulates lipid metabolism genes.

In one embodiment, the LMM comprises SREBF1, or SREBF2, or a functional fragment or analog thereof. In one embodiment, the lipid metabolism modulator comprises at least 60, 70, 80, 90, 95, 98, 99 or 100% identity with the amino acid sequence of SREBF1; e.g., SEQ ID NOs:1 or 34, or a functional fragment thereof, e.g., SEQ ID NO: 26, SEQ ID NO: 27, or SEQ ID NO: 36; or differs by 1, 2, or 3 or more amino acid residues but no more than 50, 40, 30, 20, 15, or 10 amino acid residues from the amino acid sequence of SREBF1, e.g., SEQ ID NOs: 1 or 34, or a functional fragment thereof, e.g., SEQ ID NO: 26, SEQ ID NO: 27, or SEQ ID NO: 36. In one embodiment, the nucleic acid encoding the lipid metabolism modulator comprises at least 60, 70, 80, 90, 95, 98, 99 or 100% identity with any of the nucleic acid sequences selected from SEQ ID NOs: 2 or 32, or the nucleic acids encoding SEQ ID NO: 26, SEQ ID NO: 27, or SEQ ID NO: 36.

In one embodiment, the LMM comprises SCD1, SCD2, SCD3, SCD4, or SCD5, or a functional fragment or analog thereof. In one embodiment, the lipid metabolism modulator comprises at least 60, 70, 80, 90, 95, 98, 99 or 100% identity with the amino acid sequence of SCD1; e.g., SEQ ID NO:3, or a functional fragment thereof; or differs by 1, 2, or 3 or more amino acid residues but no more than 50, 40, 30, 20, 15, or 10 amino acid residues from the amino acid sequence of SCD1, e.g., SEQ ID NO: 3, or a functional fragment thereof. In one embodiment, the nucleic acid encoding the lipid metabolism modulator comprises at least 60, 70, 80, 90, 95, 98, 99 or 100% identity with any of the nucleic acid sequences selected from SEQ ID NOs: 4.

In one embodiment, the LMM comprises any of the components provided in Table 1 or a functional fragment thereof. In one embodiment, the LMM comprises at least 60, 70, 80, 90, 95, 98, 99 or 100% identity with the amino acid sequence of any of the components provided in Table 1 or a functional fragment thereof; or differs by 1, 2, or 3 or more amino acid residues but no more than 50, 40, 30, 20, 15, or 10 amino acid residues from the amino acid sequence of any of the components provided in Table 1 or a functional fragment thereof. In one embodiment, the nucleic acid encoding the lipid metabolism modulator comprises at least 60, 70, 80, 90, 95, 98, 99 or 100% identity with a nucleic acid sequence encoding any of the components provided in Table 1 or a functional fragment thereof.

In one embodiment, the modification comprises a cis or trans regulatory element that increases the expression of a nucleic acid that encodes a lipid metabolism gene product, e.g., a lipid metabolism gene product selected from Table 1.

In one embodiment, the nucleic acid encoding the lipid metabolism modulator comprises a plasmid or a vector.

In one embodiment, the nucleic acid encoding the lipid metabolism modulator is introduced into the cell by transfection (e.g., electroporation), transduction, or any other delivery method described herein.

In one embodiment, the nucleic acid encoding the lipid metabolism modulator is integrated into the chromosomal genome of the cell. In one embodiment, the LMM is stably expressed.

In one embodiment, the nucleic acid encoding the lipid metabolism modulator is not integrated into the chromosomal genome of the cell. In one embodiment, the LMM is transiently expressed.

Products

Products described herein include polypeptides, e.g., recombinant proteins; nucleic acid molecules, e.g., DNA or RNA molecules; multimeric proteins or complexes; lipid-encapsulated particles, e.g., virus-like particles, vesicles, or exosomes; or other molecules, e.g., lipids. In an embodiment, the product is a polypeptide, e.g., a recombinant polypeptide. For example, the recombinant polypeptide can be a difficult to express protein or a protein having complex and/or non-natural structures, such as a next generation biologic, e.g., a bispecific antibody molecule, a fusion protein, or a glycosylated protein.

In any of the methods described herein, the method for producing a product further comprises introducing to the cell an exogenous nucleic acid encoding the product, e.g., polypeptide, e.g., recombinant polypeptide.

In one embodiment, the exogenous nucleic acid encoding the recombinant polypeptide is introduced after providing a cell comprising a modification that modulates lipid metabolism. In another embodiment, the exogenous nucleic acid encoding the recombinant polypeptide is introduced after culturing the cell, e.g., under conditions suitable for modulation of lipid metabolism by the modification.

In one embodiment, the exogenous nucleic acid encoding the product, e.g., recombinant polypeptide, is introduced prior to providing a cell comprising a modification that modulates lipid metabolism. In another embodiment, the exogenous nucleic acid encoding the recombinant polypeptide is introduced prior to culturing the cell, e.g., under conditions suitable for modulation of lipid metabolism by the modification.

In any of the compositions, preparations, or methods described herein, the product, e.g., recombinant polypeptide, is a therapeutic polypeptide or an antibody molecule, e.g., an antibody or an antibody fragment thereof. In one embodiment, the antibody molecule is a monoclonal antibody. In one embodiment, the antibody molecule is a bispecific antibody molecule, e.g., a BiTE (Bispecific T cell Engager), a DART (Dual Affinity Re-Targeting or Redirected T cell). In one embodiment, the product, e.g., recombinant polypeptide, is selected from Table 2 or 3.

In embodiments, the product is stably expressed by the cell. In one embodiment, the exogenous nucleic acid encoding the product, e.g., recombinant polypeptide, is integrated into the chromosomal genome of the cell. Alternatively, the product is transiently expressed by the cell. In one embodiment, the exogenous nucleic acid encoding the product, e.g., the recombinant polypeptide, is not integrated into the chromosomal genome of the cell.

Host Cells

Provided herein are cells for producing the products described herein and methods of engineering such cells.

In any of the compositions, preparations, or methods described herein, the cell is a eukaryotic cell. In one embodiment, the cell is a mammalian cell, a yeast cell, an insect cell, an algae cell, or a plant cell. In one embodiment, the cell is a rodent cell. In one embodiment, the cell is a Chinese hamster ovary (CHO) cell. Examples of CHO cells include, but are not limited to, CHO-K1, CHOK1SV, Potelligent CHOK1SV (FUT8-KO), CHO GS-KO, Exceed (CHOK1SV GS-KO), CHO-S, CHO DG44, CHO DXB11, CHOZN, or a CHO-derived cell.

In any of the compositions, preparations, or methods described herein, the cell is selected from the group consisting of HeLa, HEK293, H9, HepG2, MCF7, Jurkat, NIH3T3, PC12, PER.C6, BHK, VERO, SP2/0, NSO, YB2/0, EB66, C127, L cell, COS, e.g., COS1 and COS7, QC1-3, CHO-K1, CHOK1SV, Potelligent CHOK1SV (FUT8-KO), CHO GS-KO, Exceed (CHOK1SV GS-KO), CHO-S, CHO DG44, CHO DXB11, and CHOZN.

In one embodiment, the cell is a eukaryotic cell other than a mammalian cell, e.g., an insect, a plant, a yeast, or an algae cell. In one embodiment, the cell is a prokaryotic cell.

In one aspect, the present disclosure features a method of engineering a cell having increased production capacity and/or improved quality of production comprising introducing to the cell or forming in the cell an exogenous nucleic acid encoding a lipid metabolism modulator, thereby engineering a cell having increased production capacity and/or improved quality of production. In an embodiment, the exogenous nucleic acid encoding a lipid metabolism modulator is introduced to the cell by transfection, transduction, e.g., viral transduction, electroporation, nucleofection, or lipofection. In an embodiment, the exogenous nucleic acid encoding a lipid metabolism modulator is integrated into the chromosomal genome of the cell. In an embodiment, the method further comprises introducing to the cell an exogenous nucleic acid encoding a recombinant polypeptide. In an embodiment, the exogenous nucleic acid encoding a recombinant polypeptide is introduced prior to introducing the exogenous nucleic acid encoding the LMM. In an embodiment, the exogenous nucleic acid encoding a recombinant polypeptide is introduced after introducing the exogenous nucleic acid encoding the LMM.

In one aspect, the present disclosure features a cell produced by providing a cell and introducing to the cell a LMM described herein, e.g., introducing an exogenous nucleic acid encoding a LMM.

In one aspect, the present disclosure features a cell comprising an exogenous nucleic acid encoding a LMM described herein In one aspect, the present disclosure features a cell engineered to produce a LMM, wherein the LMM modulates the expression of a product, e.g., a next generation biologic (NGB) described herein. In one embodiment, the cell is a CHO cell.

In one aspect, the present disclosure features a CHO cell engineered to produce a LMM, wherein the LMM modulates the expression of a product, e.g., a Next generation biologic (NGB) described herein.

In one aspect, the present disclosure features a CHO cell engineered to express an LMM and a NGB, wherein the population has been selected for high level expression of the NGB.

In one aspect, the present disclosure features a CHO cell engineered to express an LMM, wherein the LMM modulates one or more characteristics of the CHO cell, wherein the engineered CHO cell is selected based on modulation of one or more characteristics selected from the group consisting of i) the expression (e.g., transcription and/or translation) of a component involved in a lipid metabolism pathway;
ii) the activity (e.g., enzymatic activity) of a component involved in a lipid metabolism pathway;
iii) the amount of lipids (e.g., phospholipids, or cholesterol) present in a cell;
iv) the amount of lipid rafts or rate of lipid raft formation;
v) the fluidity, permeability, and/or thickness of a cell membrane (e.g., a plasma membrane, a vesicle membrane, or an organelle membrane);
vi) the conversion of saturated lipids to unsaturated lipids or conversion of unsaturated lipids to saturated lipids;
vii) the amount of saturated lipids or unsaturated lipids, e.g., monounsaturated lipids;
viii) the composition of lipids in the cell to attain a favorable composition that increases ER activity;

ix) the expansion of the ER (e.g., size of the ER, the ER membrane surface, or the amounts of the proteins and lipids that constitute and/or reside within the ER);

x) the expansion of the Golgi (e.g., the number and size of the Golgi, the Golgi surface, or the number or amounts of proteins and molecules that reside within the Golgi);

xi) the amount of secretory vesicles or the formation of secretory vesicles;

xii) the amount or rate of secretion of the product;

xiii) the proliferation capacity, e.g., the proliferation rate;

xiv) culture viability or cell survival;

xv) activation of membrane receptors;

xvi) the unfolded protein response (UPR);

xvii) the yield or rate of production of the product;

xviii) the product quality (e.g., aggregation, glycosylation heterogeneity, fragmentation, proper folding or assembly, post-translational modification, or disulfide bond scrambling); and/or xix) cell growth/proliferation or cell specific growth rate.

In any of the methods or cells, e.g., engineered cells, described herein, the cell expresses or comprises the LMM is selected from a group consisting of SREBF1, SREBF2, SCD1, SCD2, SCD3, SCD4, and SCD5, or a functional fragment thereof.

In any of the methods or cells, e.g., engineered cells, described herein, the cell expresses or comprises a product, e.g., a recombinant product, e.g., a next generation biologic selected from a group consisting of a bispecific antibody, a fusion protein, or a glycosylated protein.

In any of the methods or cells, e.g., engineered cells described herein, the cell is a CHO cell selected from the group consisting of CHO-K1, CHOK1SV, Potelligent CHOK1SV (FUT8-KO), CHO GS-KO, Exceed (CHOK1SV GS-KO), CHO-S, CHO DG44, CHO DXB11, CHOZN, or a CHO-derived cell.

Compositions and Preparations

In one aspect, the present disclosure also features a preparation of a product described herein made by a method described herein. In one embodiment, at least 70, 80, 90, 95, 98 or 99%, by weight or number, of the products in the preparation are properly folded or assembled. In one embodiment, less than 50%, 40%, 30%, 25%, 20%, 15%, 10%, or 5%, by weight or number, of the products in the preparation are aggregated. In one embodiment, less than 50%, 40%, 30%, 25%, 20%, 15%, 10%, or 5%, by weight or number, of the products in the preparation are fragments of the product.

In some embodiments, the present disclosure features a preparation of a polypeptide, e.g., a polypeptide of Table 2 or Table 3, made by a method described herein. In some embodiments, the cell used in the method is a CHO cell selected from the group consisting of CHOK1, CHOK1SV, Potelligent CHOK1SV, CHO GS knockout, CHOK1SV GS-KO, CHOS, CHO DG44, CHO DXB11, CHOZN, or a CHO-derived cell.

In one aspect, the present disclosure features a mixture comprising a cell described herein, e.g., a cell comprising a modification that modulates lipid metabolism, and a product produced by the cell. In one embodiment, the mixture comprises the product at a higher concentration, e.g., at least, 1%, 2%, 3%, 4%, 5%, 6%, 7%, 8%, 9%, 10%, 20%, or 30% higher concentration, by weight or number, of product than would be seen without the modification. In one embodiment, at least 70%, 80%, 90%, 95%, 98% or 99%, by weight or number, of the products in the mixture are properly folded or assembled. In one embodiment, less than 50%, 40%, 30%, 25%, 20%, 15%, 10%, or 5%, by weight or number, of the products in the mixture are aggregated. In one embodiment, less than 50%, 40%, 30%, 25%, 20%, 15%, 10%, or 5%, by weight or number, of the products in the mixture are fragments of the product. In some embodiments, the product is a recombinant polypeptide, e.g., a recombinant polypeptide of Table 2 or Table 3.

In one aspect, the present disclosure features a preparation of medium conditioned by culture of a cell described herein, wherein the cell comprises a modification that modulates lipid metabolism. In one embodiment, the product is present in the preparation at a higher concentration, e.g., at least, 1%, 2%, 3%, 4%, 5%, 6%, 7%, 8%, 9%, 10%, 20%, or 30% higher concentration, by weight or number, than would be seen without the modification. In one embodiment, at least 70%, 80%, 90%, 95%, 98% or 99%, by weight or number, of the product in the preparation are properly folded or assembled. In one embodiment, less than 50%, 40%, 30%, 25%, 20%, 15%, 10%, or 5%, by weight or number, of the products in the preparation are aggregated. In one embodiment, less than 50%, 40%, 30%, 25%, 20%, 15%, 10%, or 5%, by weight or number, of the products in the preparation are fragments of the product. In some embodiments, the product is a recombinant polypeptide, e.g., a recombinant polypeptide of Table 2 or Table 3.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and are not intended to be limiting. Headings, sub-headings or numbered or lettered elements, e.g., (a), (b), (i) etc., are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

FIGS. 3A, 3B, and 3C show the determination of exogenous SCD1-V5 and SREBF1-V5 expressed in CHO Flp-In™ cell pools following transient transfection with a plasmid encoding a difficult to express recombinant Fc fusion protein (also referred to as Fc fusion protein or FP) (FIG. 3A) or eGFP (FIG. 3B). FIG. 3C shows determination of exogenous V5-tagged SCD1 and SREBF1 expressed in untransfected stably expressing CHO Flp-In™ cell pools. Western blot analysis was performed on cell lysates obtained 96 hours following electroporation with the Fc fusion protein, as well as the cell pool solely expressing the indicated V5-tagged lipid metabolism modulator (LMM), SCD1 or SREBF1. Anti-V5 primary antibody and anti-mouse HRP conjugated secondary antibody was used to detect expression of the V5-tagged LMM and anti-β-actin or anti L7a (as indicated) followed by exposure with anti-mouse and anti-rabbit HRP conjugated secondary antibodies respectively were used as loading controls for LMM detection.

FIG. 5A shows cell concentration. The lower columns represent viable cell concentration whilst the whole column represents the total concentration of cells; lower error bars represent the standard deviation of viable cells whilst upper error bars represent that of the total cell concentration.

FIG. 5B shows culture viability based on the data outlined in FIG. 5A. Error bars represent standard deviation. Statistical significance was calculated using two-tailed T-test compared to the control values of the particular time points: *Viable cell concentration significance using two-tailed T-test [p<0.05]. Total cell concentration significance using two-tailed T-tests [p<0.05] (n=3).

FIG. 7C shows the total fluorescence per ml of culture as calculated by multiplying the measured arithmetic mean fluorescence by total cell concentration ($\times 10^6$/ml). Error bars indicate standard deviation. Statistical significance was calculated using a two-tailed T-test compared to the control values of the particular time points (n=3). *Indicates statistically significant values [p<0.05]. Data was generated using FACSCalibur (BD Biosciences).

FIG. 8A is a western blot showing bands corresponding to antibody A, as detected by using an anti-heavy chain primary antibody and an anti-rabbit HRP conjugated secondary antibody. FIG. 8B shows the average fold change in antibody production in the LMM engineered cell pools compared to values generated from the control cell pool as determined by Protein A HPLC.

FIG. 9A is a western blot showing the bands representative of the Fc fusion protein as detected by using an anti-heavy chain primary antibody and an anti-rabbit HRP conjugated secondary antibody. FIG. 9B shows the average fold change in the Fc fusion protein production in the LMM engineered cell pools compared to values generated from the control cell pool as determined by Protein A HPLC.

FIG. 10A is a western blot showing the bands representative of antibody A as detected by using an anti-heavy chain primary antibody and an anti-rabbit HRP conjugated secondary antibody. FIG. 10B shows the average fold change in antibody production in the LMM engineered cell pools compared to values generated in the control cell pool as determined by Protein A HPLC.

FIG. 11A shows a western blot of the transiently produced fusion protein, as detected by using an anti-heavy chain primary antibody followed by exposure with an anti-rabbit HRP conjugated secondary antibody. FIG. 11B shows the average fold change in the Fc fusion protein production in the LMM engineered cell pool compared to the control cell pools as determined by Protein A HPLC.

FIG. 12A shows a western blot of the supernatants from the cells; antibody A was detected by using an anti-heavy chain primary antibody followed by exposure with an anti-rabbit HRP conjugated secondary antibody. FIG. 12B shows Coomassie analysis in which the bands show the relative levels of antibody A present in the supernatant at 168 hours post transfection.

Figure 15A:
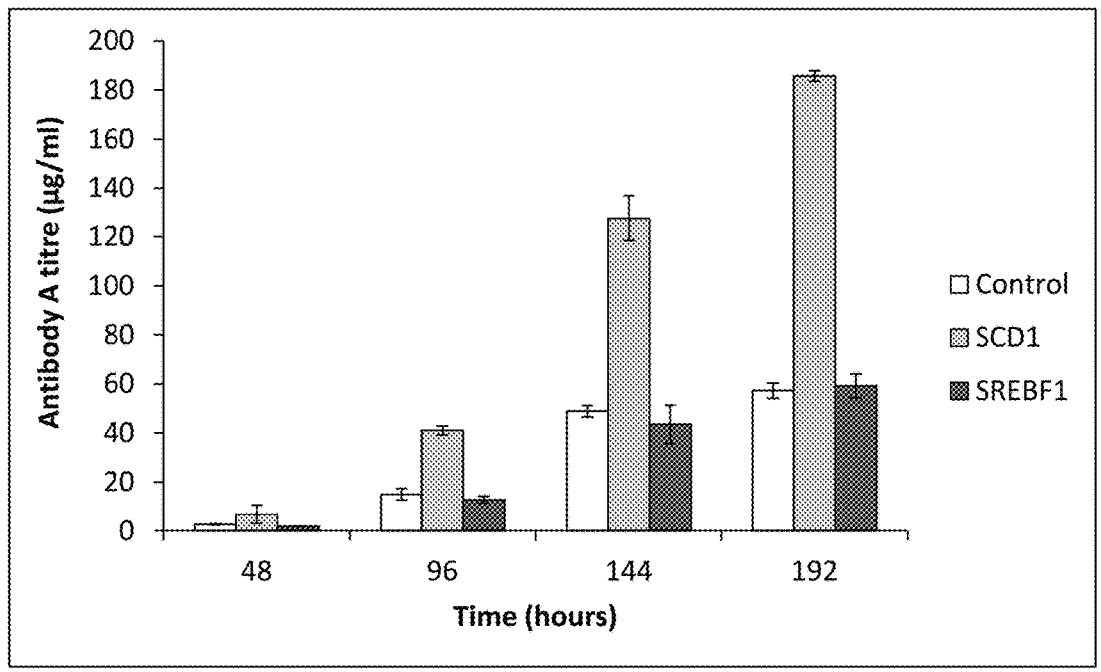
Figure 15B:
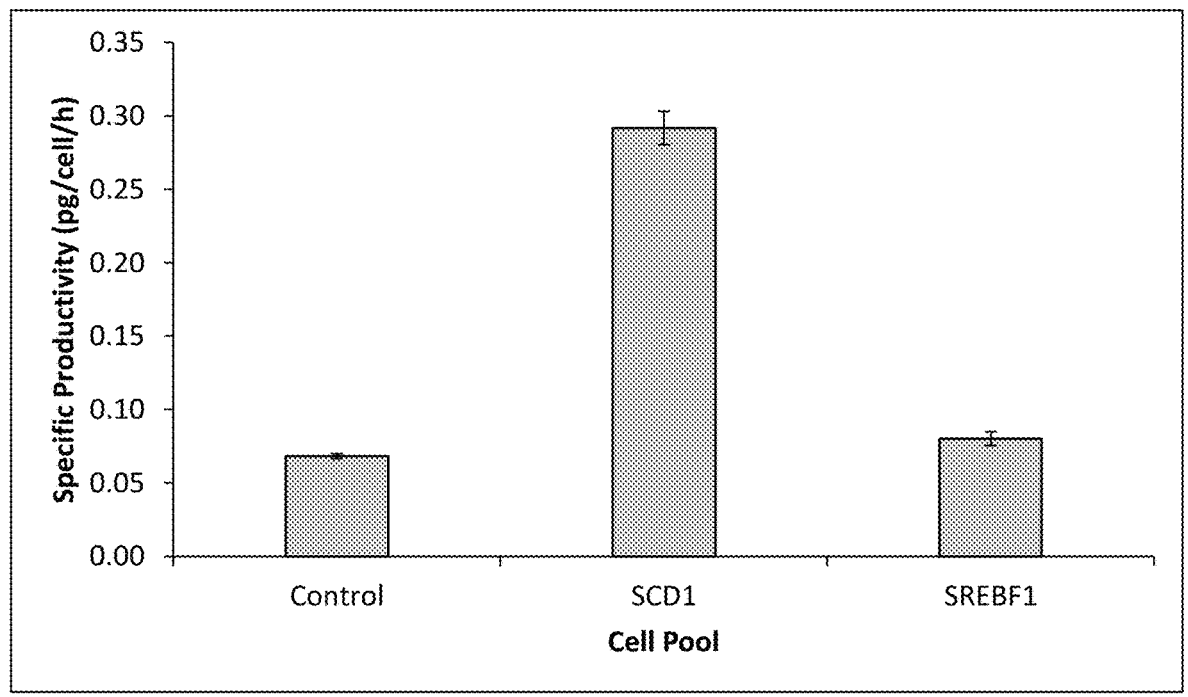

FIGS. 15A and 15B shows analysis of antibody A production from supernatant samples harvested after 48, 72, 96 and 144 hours from CHO cell pools stably integrated with control, SCD1-V5 or SREBF1-V5 containing vectors and subsequently stably integrated with an antibody A construct. FIG. 15A shows volumetric antibody concentration whilst FIG. 15B shows specific productivity of antibody A. Error bars show standard deviation (n=3).

Figure 16A:
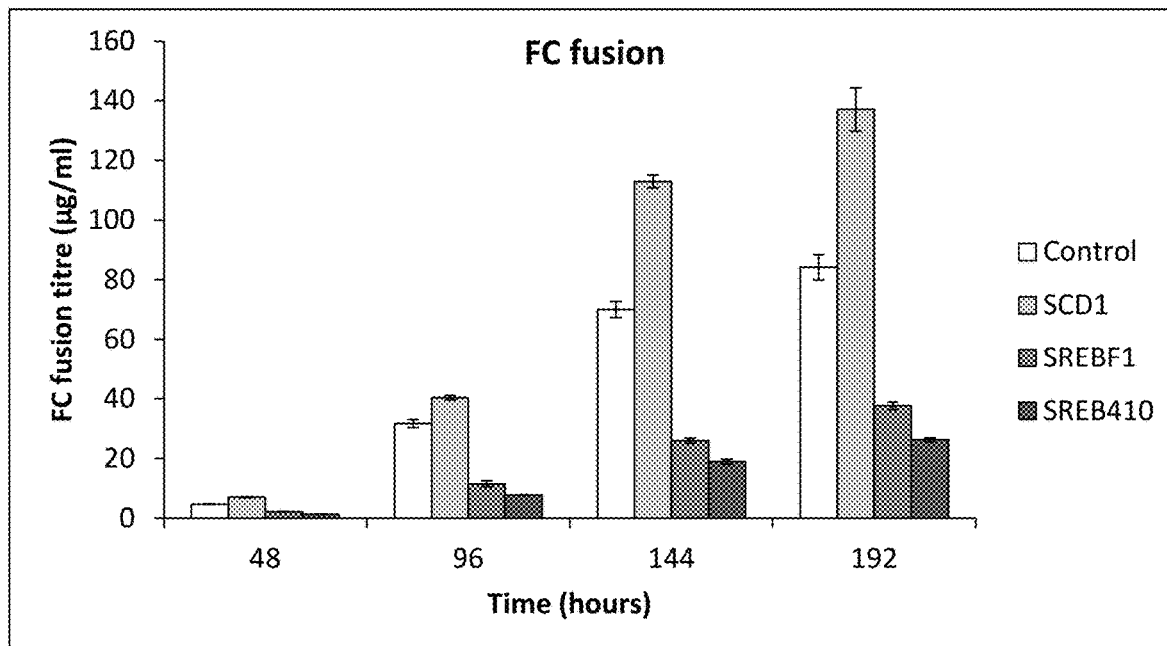
Figure 16B:
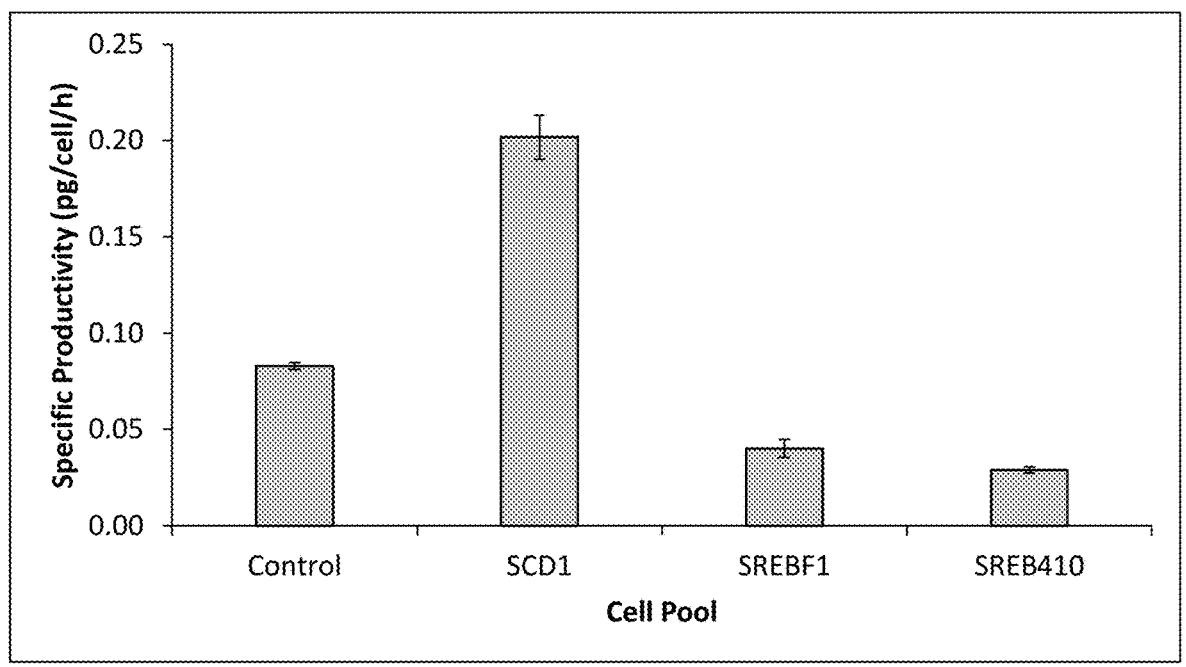

FIGS. 16A and 16B shows analysis of FC fusion protein production from supernatant samples harvested after 48, 72, 96 and 144 hours from a CHO cell pools stably integrated with control, SCD1-V5, SREBF1-V5 or SREBF410-V5 containing vectors and subsequently stably integrated with an FC fusion protein construct. FIG. 16A shows volumetric FC fusion protein concentration whilst FIG. 16B shows specific productivity of the FC fusion protein. Error bars show standard deviation (n=3).

Figure 17A:
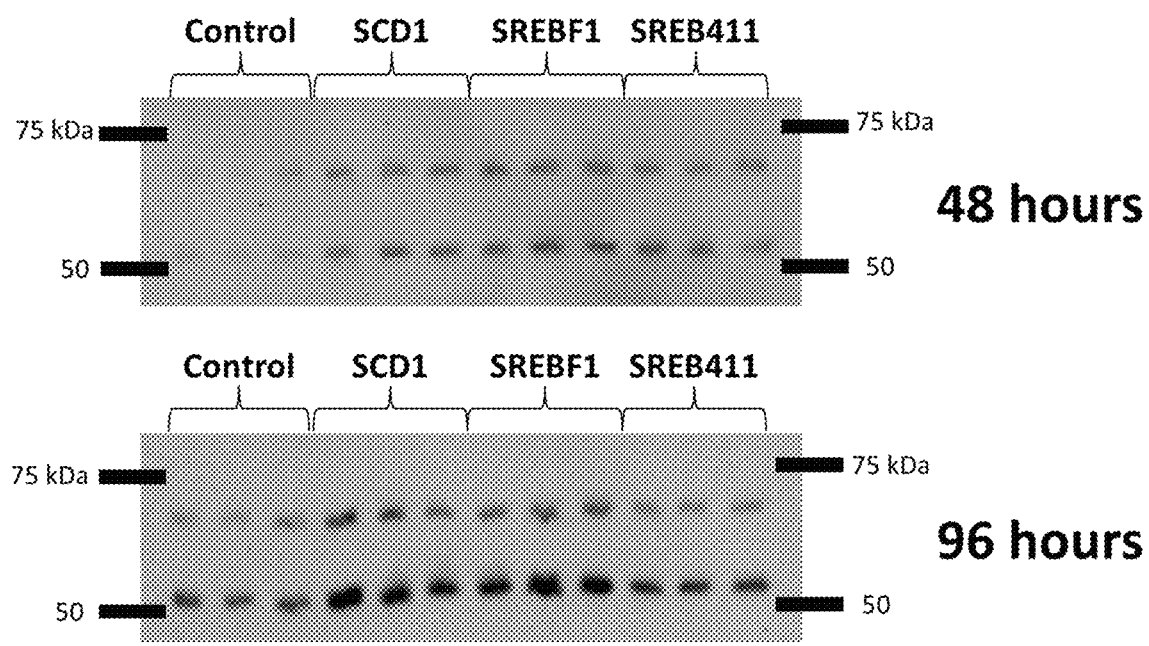
Figure 17B:
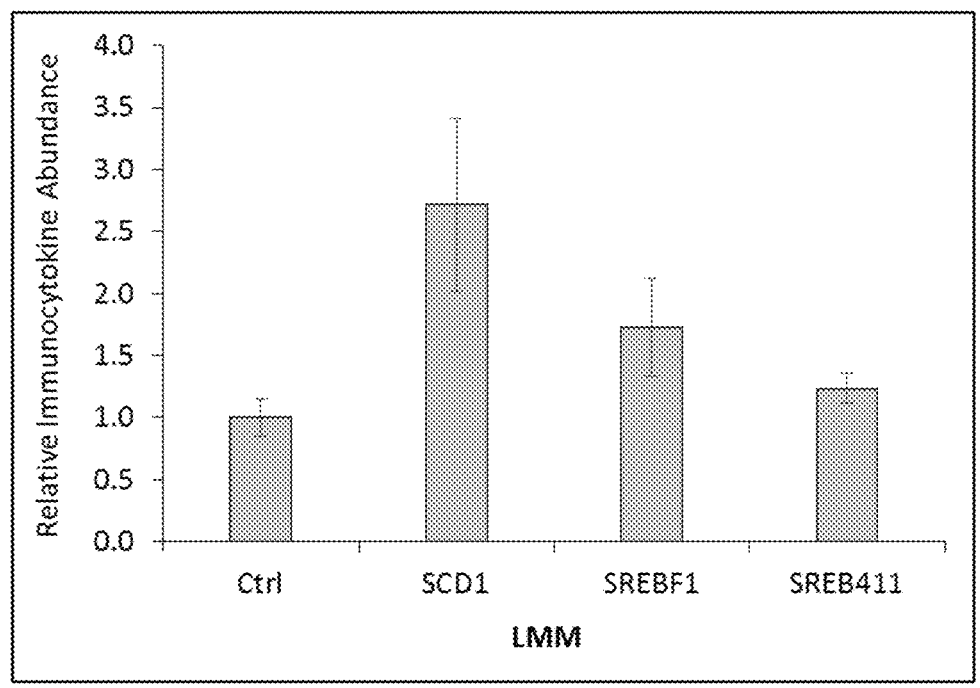

FIG. 17A shows western analysis of immunocytokine expression from CHO GSKO cells following transient transfection of a nucleic acid construct encoding genes appropriate for expression of the immunocytokine and either no LMM (control), SCD1, SREBF1 or SREB411 genes at 48 and 96 h post transfection. Supernatant samples were reduced and bands present detected using an anti heavy chain primary antibody followed by exposure to an anti-rabbit HRP conjugated secondary antibody. The lower band represents a native heavy chain antibody whilst the upper band is indicative of a heavy chain molecule fused to a cytokine. FIG. 17B shows relative immunocytokine abundance of samples obtained at 96 hours post transfection.

DETAILED DESCRIPTION

As both current and next generation biologics continue to gain therapeutic utility in patients, the demand for large quantities of next generation biologic products having a high grade of quality for therapeutic use, as well as efficient means for production and efficient development of production cell line will escalate. Furthermore, many next generation biologics are difficult to express and produce in conventional cell lines using conventional expression techniques known in the art. The current methods are not sufficient to produce these products in the large quantities and at the high grade of quality required for clinical use. As such, the present disclosure features methods and compositions for obtaining higher yields of a product, e.g., a next generation biologics, with improved quality as compared to the yield and quality obtained from current production methods. The methods and compositions described herein are also useful for engineering cells or cell lines with improved productivity, product quality, robustness, and/or culture viability, as compared to the cell expression systems currently used to produce recombinant products.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "a cell" can mean one cell or more than one cell.

"Component of a lipid metabolism pathway", as used herein, refers to a molecule, polypeptide, or enzyme that, directly or indirectly, synthesizes a lipid, degrades a lipid, converts a lipid from one lipid species to another lipid species, or modifies a lipid. In one embodiment, the component can be an enzyme substrate, an enzyme reaction product, or an enzyme cofactor. In one embodiment, the component of a lipid metabolism pathway is a LMM. In one embodiment, the component of a lipid metabolism pathway is provided in Table 1.

"Endogenous", as used herein, refers to any material from or naturally produced inside an organism, cell, tissue or system.

"Exogenous", as used herein, refers to any material introduced to or produced outside of an organism, cell, tissue or system. Accordingly, "exogenous nucleic acid" refers to a nucleic acid that is introduced to or produced outside of an organism, cell, tissue or system. In an embodiment, sequences of the exogenous nucleic acid are not naturally produced, or cannot be naturally found, inside the organism, cell, tissue, or system that the exogenous nucleic acid is introduced into. In embodiments, non-naturally occurring products, or products containing portions that are non-naturally occurring are exogenous materials with respect to the host cells described herein.

"Forming", as used herein, refers to introducing into the cell, synthesizing within the cell, or any other process that results in the nucleic acid encoding a LMM or an exogenous LMM being located within the cell.

"Heterologous", as used herein, refers to any material from one species, when introduced to an organism, cell, tissue or system from a different species. In embodiments, a heterologous material also encompasses a material that includes portions from one or multiple species or portions that are non-naturally occurring. By way of example, in an embodiment, a nucleic acid encoding a fusion protein wherein a portion of the fusion protein is human, a portion of the fusion protein is bacteria, and a portion of the fusion protein is non-naturally occurring, and the nucleic acid is introduced to a human cell, the nucleic acid is a heterologous nucleic acid.

"Lipid metabolism pathway", as used herein, refers to a process associated with the synthesis of a lipid or lipid-associated molecule, the elongation of a lipid or lipid-associated molecule, the degradation of a lipid or lipid-associated molecule, the incorporation of a lipid or lipid-associated molecule into a membrane, the state of saturation of a lipid or lipid-associated molecule (e.g., saturated or unsaturated), or conversion or modification of the chemical structure (e.g., re-esterification) of a lipid or lipid-associated molecule. In one embodiment, the lipid metabolism pathway results in lipid synthesis, lipid elongation, lipid degradation, changes in membrane composition or fluidity, formation or modulation of lipid rafts, or modification or conversion of a lipid (e.g., saturation or de-saturation of a lipid, or re-esterification of a lipid). Examples of lipid metabolism pathways include, but are not limited to: de novo lipogenesis, fatty acid re-esterification, fatty acid saturation, fatty acid de-saturation, fatty acid elongation, and phospholipid biosynthesis, and unfolded protein response.

"Lipid metabolism modulator" or "LMM", as used herein, refers to a molecule, gene product, polypeptide, or enzyme that modulates, e.g., increases or decreases, one or more of the following: the expression (e.g., transcription or translation) of a component involved in a lipid metabolism pathway; the activity (e.g., enzymatic activity) of a component, e.g., gene product, involved in a lipid metabolism pathway; the level or amount of lipids present in a cell; the level or amount of lipid rafts or rate of lipid raft formation; the fluidity, permeability, or thickness of a cell membrane, e.g., plasma membrane or an organelle membrane; the conversion of saturated lipids to unsaturated lipids or vice versa; the level or amount of saturated lipids or unsaturated lipids in a cell, e.g., monounsaturated lipids; lipid composition to achieve a favorable lipid composition that has a favorable impact on the activity of the ER; the expansion of the ER; the expansion of the Golgi; the level or amount of secretory vesicles or secretory vesicle formation; the level or rate of secretion; activation or inactivation of membrane receptors (e.g., ATR (see e.g., The increase of cell-membranous phosphatidylcholines containing polyunsaturated fatty acid residues induces phosphorylation of p53 through activation of ATR. Zhang X H, Zhao C, Ma Z A. J Cell Sci. 2007 Dec. 1; 120(Pt 23):4134-43 PMID: 18032786; ATR (ataxia telangiectasia mutated- and Rad3-related kinase) is activated by mild hypothermia in mammalian cells and subsequently activates p53. Roobol A, Roobol J, Carden M J, Bastide A, Willis A E, Dunn W B, Goodacre R, Smales C M. Biochem J. 2011 Apr. 15; 435(2):499-508. doi: 10.1042/BJ20101303. PMID: 21284603) and SREPB (see e.g., Int J Biol Sci. 2016 Mar. 21; 12(5):569-79. doi: 10.7150/ijbs.14027. eCollection 2016. Dysregulation of the Low-Density Lipoprotein Receptor Pathway Is Involved in Lipid Disorder-Mediated Organ Injury. Zhang Y, Ma K L, Ruan X Z, Liu B C); and additional receptors, see e.g., Biochim Biophys Acta. 2016 Mar. 17. pii: S1388-1981(16)30071-3. doi: 10.1016/j.bbalip.2016.03.019; and/or the unfolded protein response (UPR). In one embodiment, the LMM comprises a polypeptide. In one embodiment, the LMM comprises a transcriptional regulator, e.g., a transcription factor. In one embodiment, the LMM comprises SREBF1 or a functional fragment thereof (e.g., SREBF-410). In one embodiment, the LMM comprises an enzyme. In one embodiment, the LMM comprises SCD1 or a functional fragment thereof.

"Modification" as used herein in the expression "modification that modulates lipid metabolism" refers to an agent that is capable of effecting an increase or decrease in the expression or activity of a component, e.g., gene product, of a lipid metabolism pathway described herein. In embodiments, the modification results in increasing the expression or activity of a component of a lipid metabolism pathway, e.g., a 1%, 2%, 5%, 10%, 15%, 20%, 25%, 30%, 35%, 40%, 45%, 50%, 55%, 60%, 65%, 70%, 75%, 80%, 85%, 90% 95%, 99%, 1-fold, 2-fold, 5-fold, 10-fold, 20-fold, 50-fold, or 100-fold or more increase in expression or activity of a component of a lipid metabolism pathway, e.g., as compared to the expression or activity of the component in the absence of the modification. In embodiments, the modification results in decreasing the expression or activity of a component of a lipid metabolism pathway, e.g., a 1%, 2%, 5%, 10%, 15%, 20%, 25%, 30%, 35%, 40%, 45%, 50%, 55%, 60%, 65%, 70%, 75%, 80%, 85%, 90% 95%, 99%%, 1-fold, 2-fold, 5-fold, 10-fold, 20-fold, 50-fold, or 100-fold or more decrease in expression or activity of a component of a lipid metabolism pathway, e.g., as compared to the expression or activity of the component in the absence of the modification. In some embodiments where the expression or activity of a component of the lipid metabolism pathway is decreased, the component is a negative regulator of a lipid metabolism pathway. In one embodiment, the modification comprises a heterologous or exogenous nucleic acid sequence encoding a lipid metabolism modulator. In one embodiment, the modification is an exogenous lipid metabolism modulator, e.g., small molecule or polypeptide, that can be introduced to a cell, e.g., by culturing the cell in the presence of the molecule or polypeptide, to modulate the lipid metabolism of the cell.

The terms "nucleic acid", "polynucleotide", and "nucleic acid molecule", as used interchangeably herein, refer to deoxyribonucleic acid (DNA) or ribonucleic acid (RNA), or a combination of a DNA or RNA thereof, and polymers thereof in either single-, double-, or triple-stranded form. The term "nucleic acid" includes, but is not limited to, a gene, cDNA, or an mRNA. In one embodiment, the nucleic acid molecule is synthetic (e.g., chemically synthesized or artificial) or recombinant. Unless specifically limited, the term encompasses molecules containing analogues or derivatives of natural nucleotides that have similar binding properties as the reference nucleic acid and are metabolized in a manner similar to naturally or non-naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

"Peptide," "polypeptide," and "protein", as used interchangeably herein, refer to a compound comprised of amino acid residues covalently linked by peptide bonds, or by means other than peptide bonds. A protein or peptide must contain at least two amino acids, and no limitation is placed on the maximum number of amino acids that can comprise a protein's or peptide's sequence. In one embodiment, a protein may comprise of more than one, e.g., two, three, four, five, or more, polypeptides, in which each polypeptide is associated to another by either covalent or non-covalent bonds/interactions. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others.

"Recombinant product" refers to a product that can be produced by a cell or a cell-free system. The product can be a molecule, a nucleic acid, a polypeptide, or any hybrid thereof. A recombinant product is one for at which at least one component of the product or at least one nucleotide of a sequence which controls the production or expression of the product, was formed by genetic engineering. Genetic engineering as used herein to generate a recombinant product or a construct that encodes a recombinant product encompasses recombinant DNA expression techniques known in the art (e.g., as described in Current Protocols in Molecular Biology); site-directed, scanning, or random mutagenesis; genome modification strategies employing CRISPR-based strategies; and zinc finger nuclease (ZFN)-based strategies. By way of example, in embodiments where the recombinant product is a nucleic acid, at least one nucleotide of the recombinant nucleic acid, or at least one nucleotide of a sequence that controls the production, e.g., transcription, of the recombinant nucleic acid was formed by genetic engineering. In one embodiment, the recombinant product is a recombinant polypeptide. In one embodiment, the recombinant product is a naturally occurring product. In one embodiment, the recombinant product is a non-naturally occurring product, e.g., a synthetic product. In one embodiment, a portion of the recombinant product is naturally occurring, while another portion of the recombinant product is non-naturally occurring. In another embodiment, a first portion of the recombinant product is one naturally occurring molecule, while another portion of the recombinant product is another naturally occurring molecule that is different from the first portion.

"Recombinant polypeptide" refers to a polypeptide that can be produced by a cell described herein. A recombinant polypeptide is one for which at least one nucleotide of the sequence encoding the polypeptide, or at least one nucleotide of a sequence which controls the expression of the polypeptide, was formed by genetic engineering or manipulation (of the cell or of a precursor cell). E.g., at least one nucleotide was altered, e.g., it was introduced into the cell or it is the product of a genetically engineered rearrangement. In an embodiment, the sequence of a recombinant polypeptide does not differ from a naturally or non-naturally occurring isoform of the polypeptide or protein. In an embodiment, the amino acid sequence of the recombinant polypeptide differs from the sequence of a naturally occurring or a non-naturally isoform of the polypeptide or protein. In an embodiment, the recombinant polypeptide and the cell are from the same species. In an embodiment, the amino acid sequence of the recombinant polypeptide is the same as or is substantially the same as, or differs by no more than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% from, a polypeptide encoded by the endogenous genome of the cell. In an embodiment, the recombinant polypeptide and the cell are from the same species, e.g., the recombinant polypeptide is a human polypeptide and the cell is a human cell. In an embodiment, the recombinant polypeptide and the cell are from different species, e.g., the recombinant polypeptide is a human polypeptide and the cell is a non-human, e.g., a rodent, e.g., a CHO, other mammalian cell, an insect cell, a plant cell, a fungal cell, a viral cell, or a bacterial cell. In an embodiment, the recombinant polypeptide is exogenous to the cell, in other words, the cell is from a first species and the recombinant polypeptide is from a second species. In one embodiment, the polypeptide is a synthetic polypeptide. In one embodiment, the polypeptide is derived from a non-naturally occurring source. In an embodiment, the recombinant polypeptide is a human polypeptide or protein which does not differ in amino acid sequence from a naturally or non-naturally occurring isoform of the human polypeptide or protein. In an embodiment, the recombinant polypeptide differs from a naturally or non-naturally occurring isoform of the human polypeptide or protein at no more than 1, 2, 3, 4, 5, 10, 15 or 20 amino acid residues. In an embodiment, the recombinant polypeptide differs from a naturally occurring isoform of the human polypeptide at no more than 1%, 2%, 3%, 4%, 5%, 6%, 7%, 8%, 9%, 10%, or 15% of its amino acid residues. In embodiments where a portion of the recombinant polypeptide comprises a sequence derived from a portion of a naturally or non-naturally occurring isoform of a human polypeptide, the portion of the recombinant polypeptide differs from the corresponding portion of the naturally or non-naturally occurring isoform by no more than 1, 2, 3, 4, 5, 10, 15, or 20 amino acid residues, or 1%, 2%, 3%, 4%, 5%, 6%, 7%, 8%, 9%, 10%, or 15% of its amino acid residues.

"Homologous", "identity", or "similarity" as used herein refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

The term "next generation biologic" or "NGB" as used herein refers to a biological composition comprising a cell or a composition produced by a cell. The biological composition is selected from the group consisting of a composition with at least one natural component, a composition with at least one natural component and at least one non-natural component, a composition with at least one natural component and at least one natural structure, and a composition with at least one natural component and at least one non-natural structure, or any combinations thereof. Next generation biologics often comprise complex and/or non-natural structures. Examples of next generation biologics include, but are not limited to, fusion proteins, enzymes or recombinant enzymes, proteins or recombinant proteins, recombinant factors with extended half-lives, growth hormones with long acting therapies, multimeric glycoproteins, next generation antibodies, antibody fragments, or antibody-like proteins (ALPs), vesicles, exosomes, liposomes, viruses, and virus-like particles, mucins, nanoparticles, extracts of a cell, and a cell being used as a reagent.

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

Modulation of Lipid Metabolism

The present disclosure features methods and compositions for modulating lipid metabolism in a cell or a cell-free system, for example, by introducing a modification to the cell or cell-free system that results in the modulation of lipid metabolism. In embodiments, the present disclosure features the use of global regulators that impact multiple aspects of pathways or processes involved in lipid metabolism, e.g., the de novo lipogenesis, fatty acid re-esterification, fatty acid saturation or desaturation, fatty acid elongation, and phospholipid biosynthesis pathways. By way of example, the global regulator is upstream in one or more lipid metabolism pathways or processes such that the global regulator impacts several, e.g., two or more, downstream processes or downstream components of lipid metabolism. In one embodiment, the global regulator is a transcription factor that can activate the expression of more than one, e.g., two or more, target genes involved in different lipid metabolism processes or pathways. Accordingly, without wishing to be bound by any theory, the use of a global regulator as described herein can result in a greater increase in production capacity, robustness, and survival of the cell than compared to the use of a downstream effector that modulates only a single target or other component of lipid metabolism. While not wishing to be bound by any theory, it is believed that a global or more widespread modulation of multiple lipid metabolism pathways increases the production capacity of a cell by affecting more processes involved in improving production capacity, product quality, and robustness of the cell.

Lipid metabolism pathways as described herein refer to processes that relate to the synthesis, degradation, conversion, or modification of lipids or lipid-associated molecules. Lipid molecules include, but are not limited to, fatty acids, glycerolipids, glycerophospholipids, phospholipids, saccharolipids, sphingolipids, and sterol lipids, e.g., cholesterol, and polyketides. Examples of lipid metabolism pathways include, but are not limited to: de novo lipogenesis, fatty acid re-esterification, fatty acid saturation, fatty acid de-saturation, fatty acid elongation, and phospholipid biosynthesis. In one embodiment, the methods described herein provide a cell comprising a modification that modulates lipid metabolism. The modification that modulates lipid metabolism can be an agent that increases or decreases the expression of a component involved in lipid metabolism. In one embodiment, the modification that modulates lipid metabolism comprises an exogenous nucleic acid encoding a lipid metabolism modulator (LMM). In such embodiments, the exogenous nucleic acid encoding a LMM is introduced to the cell by any of the nucleic acid delivery methods or techniques described herein, e.g., transduction or transfection In one embodiment, the methods described herein provide a cell comprising one or more, e.g., one, two, three, four, five, six, seven, eight, nine or ten, modifications that modulate lipid metabolism. In embodiments where the cell comprises two or more modifications that modulate lipid metabolism, each modification that modulates lipid metabolism comprises an exogenous nucleic acid that encodes a LMM. In one embodiment, each of the two or more exogenous nucleic acids that encode a LMM can be located within the same nucleic acid molecule, or are placed on two or more different nucleic acid molecules. In such embodiments where the cell comprises two or more nucleic acid sequences encoding LMMs, the LMMs are different from each other, e.g., encode a different polypeptide sequence or have a different function.

In embodiments, modulation of lipid metabolism in a cell, e.g., by introducing and expressing an exogenous nucleic acid encoding an LMM described herein, alters, e.g., increases or decreases, one or more of the following:
  i) the expression (e.g., transcription and/or translation) of a component involved in a lipid metabolism pathway;
  ii) the activity (e.g., enzymatic activity) of a component involved in a lipid metabolism pathway;
  iii) the amount of lipids (e.g., phospholipids, or cholesterol) present in a cell;
  iv) the amount of lipid rafts or rate of lipid raft formation;
  v) the fluidity, permeability, and/or thickness of a cell membrane (e.g., a plasma membrane, a vesicle membrane, or an organelle membrane);
  vi) the conversion of saturated lipids to unsaturated lipids or conversion of unsaturated lipids to saturated lipids;
  vii) the amount of saturated lipids or unsaturated lipids, e.g., monounsaturated lipids;
  viii) the composition of lipids in the cell to attain a favorable composition that increases ER activity;
  ix) the expansion of the ER (e.g., size of the ER, the ER membrane surface, or the amounts of the proteins and lipids that constitute and/or reside within the ER);
  x) the expansion of the Golgi (e.g., the number and size of the Golgi, the Golgi surface, or the number or amounts of proteins and molecules that reside within the Golgi);
  xi) the amount of secretory vesicles or the formation of secretory vesicles;
  xii) the amount or rate of secretion of the product;
  xiii) the proliferation capacity, e.g., the proliferation rate;
  xiv) culture viability or cell survival;
  xv) activation of membrane receptors;
  xvi) the unfolded protein response (UPR);
  xvii) the yield or rate of production of the product;
  xviii) the product quality (e.g., aggregation, glycosylation heterogeneity, fragmentation, proper folding or assembly, post-translational modification, or disulfide bond scrambling); and/or
  xix) cell growth/proliferation or cell specific growth rate.

In an embodiment, modulation of lipid metabolism results in an increase in any of the properties listed above, e.g., a 1%, 2%, 5%, 10%, 20%, 30%, 40%, 50%, 60%, 70%, 80%, 90%, 95%, or 99%, or more, or at least 1-fold, 2-fold, 3-fold, 4-fold, 5-fold, 10-fold, 20-fold, 50-fold, or 100-fold or more, increase in any of the properties listed above as compared to a cell without modulation of lipid metabolism. In an embodiment, modulation of lipid metabolism results in a decrease in any of the properties listed above, e.g., a 1%, 2%, 5%, 10%, 20%, 30%, 40%, 50%, 60%, 70%, 80%, 90%, 95%, or 99%, or more, or at least 1-fold, 2-fold, 3-fold, 4-fold, 5-fold, 10-fold, 20-fold, 50-fold, or 100-fold or more, decrease in any of the properties listed above as compared to a cell without modulation of lipid metabolism.

In an embodiment, a modification that modulates lipid metabolism increases or decreases the expression or activity of a component involved in one or more lipid metabolism pathways. In embodiments where the modification that modulates lipid metabolism results in an increase in the expression, e.g., transcription or translation, or an increase in the activity of a component of a lipid metabolism pathway, the component is a positive regulator of the lipid metabolism pathway. In embodiments where the modification that modulates lipid metabolism results in a decrease in the expression, e.g., transcription or translation, or a decrease in the activity of a component of a lipid metabolism pathway, the component is a negative regulator of the lipid metabolism pathway. Assays for quantifying the expression, e.g., transcription and/or translation, of a gene of the lipid metabolism pathway, are known in the art, and include quantifying the amount of mRNA encoding the gene; or quantifying the amount of the gene product, or polypeptide; PCR-based assays, e.g., quantitative real-time PCR; Northern blot; or microarray. Assays for quantifying the activity of a component of the lipid metabolism pathway, e.g., an enzyme of the lipid metabolism pathway, will be specific to the particular component of the lipid metabolism pathway.

In embodiments where the modulation of the lipid metabolism of a cell results in an increase in the level or amount of lipids in the cell, the total level or total amount of lipids in the cell can be increased. In another embodiment, the level or amount of one or more species of lipids, e.g., a phospholipid or cholesterol, in the cell can be increased. An increase in the level or amount of lipids in the cell (e.g., total or a select lipid species) comprises a 1%, 2%, 5%, 10%, 15%, 20%, 25%, 30%, 35%, 40%, 45%, 50%, 55%, 60%, 65%, 70%, 75%, 80%, 85%, 90%, 95%, or more, or a one-fold, two-fold, three-fold, four-fold, or five-fold, 10-fold, 20-fold, 50-fold, or 100-fold, increase in the level or amount of lipids in the cell after modulation of lipid metabolism, e.g., live cells, as compared to cells that do not comprise a modification that modulates lipid metabolism. Assays for quantifying the level or amount of lipids in a cell are known in the art, and include enzymatic assays and oxidation assays and measurement by mass spectrometry of lipid components in a particular compartment (e.g., organelle) or from the total cell.

In one embodiment, a modification that modulates lipid metabolism results in increased cell survival. For example, cell survival can be measured by determining or quantifying cell apoptosis, e.g., the number or amount of cells that have been killed or died. An increase in cell survival comprises a 1%, 2%, 5%, 10%, 15%, 20%, 25%, 30%, 35%, 40%, 45%, 50%, 55%, 60%, 65%, 70%, 75%, 80%, 85%, 90%, 95%, or more, or a one-fold, two-fold, three-fold, four-fold, or five-fold, 10-fold, 20-fold, 50-fold, or 100-fold, increase in the number of cells after modulation of lipid metabolism, e.g., live cells, as compared to cells that do not comprise a modification that modulates lipid metabolism. Alternatively, an increase in cell survival comprises a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more decrease in the number of apoptotic cells after modulation of lipid metabolism, e.g., as compared to cells without modulation of lipid metabolism. Methods for detecting cell survival or apoptosis are known in the art, e.g., Annexin V assays, and are described herein in the Examples.

In one embodiment, a modification that modulates lipid metabolism results in increased culture viability. For example, culture viability can be measured by determining or quantifying the number or amount of live cells, e.g., live cells in a culture or population of cells, or cells that have a characteristic related to being viable, e.g., proliferation markers, intact DNA, or do not display apoptotic markers. An increase in culture viability comprises a 1%, 2%, 5%, 10%, 15%, 20%, 25%, 30%, 35%, 40%, 45%, 50%, 55%, 60%, 65%, 70%, 75%, 80%, 85%, 90%, 95%, or more, or a one-fold, two-fold, three-fold, four-fold, or five-fold, 10-fold, 20-fold, 50-fold, or 100-fold, or more increase in the number of cells, e.g., live cells, after modulation of lipid metabolism, e.g., as compared to cells without modulation of lipid metabolism. Methods for determining culture viability are known in the art, and are described herein in Example 3. Other methods for assessing culture viability include, but are not limited to, trypan blue exclusion methods followed by counting using a hemocytometer or Vi-CELL (Beckman-Coulter). Other methods for determining viable biomass include methods using radiofrequency impedance or capacitance (e.g., Carvell and Dowd, 2006, Cytotechnology, 50:35-48), or using Raman spectroscopy (e.g., Moretto et al., 2011, American Pharmaceutical Review, Vol. 14).

In one embodiment, a modification that modulates lipid metabolism results in increased cell proliferation. For example, the ability of a cell to proliferate can be measured by quantifying or counting the number of cells, cell doublings, or growth rate of the cells. Alternatively, proliferating cells can be identified by analysis of the genomic content of the cells (e.g., replicating DNA), e.g., by flow cytometry analysis, or presence of proliferation markers, e.g., Ki67, phosphorylated cyclin-CDK complexes involved in cell cycle. An increase in the ability to proliferate comprises a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or one-fold, two-fold, three-fold, four-fold, five-fold, 10-fold, 20-fold, 50-fold, or 100-fold, or more increase in the number of cells, or number of cells expressing a proliferation marker, after modulation of lipid metabolism. Alternatively, an increase in the ability to proliferate comprises a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or one-fold, two-fold, three-fold, four-fold, five-fold, 10-fold, 20-fold, 50-fold, or 100-fold, or more increase in the doubling or growth rate of the cells after modulation of lipid metabolism. Cell counting can be performed using a cell counting machine, or by use of a hemacytometer.

In one embodiment, a modification that modulates lipid metabolism results in an increase in production capacity, e.g., the amount, quantity, or yield of product produced, or the rate of production. An increase in the amount, quantity, or yield of the product produced comprises 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or by 1-fold, 2-fold, 5-fold, 10-fold, 20-fold, 50-fold, 100-fold or more increase in the amount, quantity, or yield of the product produced after modulation of lipid metabolism, e.g., as compared to the amount, quantity, or yield of the product produced by a cell without modulation of the lipid metabolism. An increase in the rate of production comprises 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or by 1-fold, 2-fold, 5-fold, 10-fold, 20-fold, 50-fold, 100-fold, or more increase in the amount, quantity, or yield of the product produced after modulation of lipid metabolism, after modulation of lipid metabolism, e.g., as compared to the rate of production of a cell without modulation of the lipid metabolism. In one embodiment, the rate of production is determined by determining the amount, quantity, or yield of the product produced in a specific unit of time.

In one embodiment, a modification that modulates lipid metabolism results in an increase in the quality of the product, e.g., aggregation, glycosylation status or heterogeneity, fragmentation, proper folding or assembly, post-translational modification, or disulfide bond scrambling. An increase quality of the product comprises a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or by 1-fold, 2-fold, 5-fold, 10-fold, 20-fold, 50-fold, 100-fold or more of: an increase in the amount or quantity of non-aggregated product, an increase in the ratio of non-aggregated product to aggregated product, or decrease in the amount or quantity of aggregated product, after modulation of lipid metabolism e.g., as compared to that observed in a cell without modulation of the lipid metabolism. An increase quality of the product comprises a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or by 1-fold, 2-fold, 5-fold, 10-fold, 20-fold, 50-fold, 100-fold or more of: an increase in the amount or quantity of properly folded or assembled product, an increase in the ratio of properly folded or assembled product to misfolded, unfolded, partially assembled, or non-assembled product, or decrease in the amount or quantity of misfolded, unfolded, partially assembled, or non-assembled product, after modulation of lipid metabolism e.g., as compared to that observed in a cell without modulation of the lipid metabolism. An increase quality of the product comprises a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or by 1-fold, 2-fold, 5-fold, 10-fold, 20-fold, 50-fold, 100-fold or more of: an increase in the amount or quantity of non-fragmented or full-length product, or a decrease in the amount or quantity of fragmented product after modulation of lipid metabolism, e.g., as compared to that observed in a cell without modulation of the lipid metabolism. An increase quality of the product comprises a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or by 1-fold, 2-fold, 5-fold, 10-fold, 20-fold, 50-fold, 100-fold or more of: an increase in the amount or quantity of functional product, or a decrease in the amount or quantity of non-functional or dysfunctional product after modulation of lipid metabolism, e.g., as compared to that observed in a cell without modulation of the lipid metabolism. An increase quality of the product comprises a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or by 1-fold, 2-fold, 5-fold, 10-fold, 20-fold, 50-fold, 100-fold or more of: an increase or decrease in the glycan heterogeneity after modulation of lipid metabolism, e.g., as compared to that observed in a cell without modulation of the lipid metabolism. An increase quality of the product comprises a 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more, or by 1-fold, 2-fold, 5-fold, 10-fold, 20-fold, 50-fold, 100-fold or more of: an increase in the amount or quantity of functional product, or a decrease in the amount or quantity of non-functional or dysfunctional product after modulation of lipid metabolism, e.g., as compared to that observed in a cell without modulation of the lipid metabolism.

Lipid Metabolism Modulators

As described herein, modulation of the lipid metabolism can be achieved by expressing or introducing a LMM, or by altering the regulation of a LMM. In one embodiment, an LMM is overexpressed in a cell, e.g., by introducing an exogenous nucleic acid encoding a LMM or by increasing expression by introducing promoter elements or other regulatory transcriptional elements. In another embodiment, the expression or activity of an LMM is inhibited or decreased, e.g., by introducing an inhibitor of the LMM or an exogenous inhibitory nucleic acid, e.g., an RNA interfering agent. Examples of inhibitory nucleic acids include short interfering RNAs (siRNAs) and short hairpin RNAs (shRNAs) that target the LMM, e.g, the mRNA encoding the LMM. In one embodiment, the activity or expression of an LMM is increased or decreased by altering the post-translational modifications or other endogenous regulatory mechanisms that regulate LMM activity or expression. Regulation by post-translational modifications include, but are not limited to, phosphorylation, sumoylation, ubiquitination, acetylation, methylation, or glycosylation can increase or decrease LMM expression or activity. By way of example, regulation of post-translational modifications can be achieved through modulation of the enzyme or molecule that modifies the LMM, or modification of the LMM such that the post-translational modification cannot occur or occurs more frequently or constitutively. Regulation of the LMM can also include modulating endogenous regulatory mechanisms that can increase or decrease LMM expression or activity, e.g., increase or decrease one or more of: miRNA regulation, protein cleavage, expression of specific isoforms, alternative splicing, and degradation.

In one embodiment, the LMM modulates, e.g., increases or decreases, the expression, e.g., transcription, or activity of a component of the lipid metabolism pathway. In another embodiment, the LMM modulates, e.g., increases or decreases, the synthesis, degradation, elongation, or structural conformation (e.g., saturation or desaturation, or esterification) of a lipid or lipid-associated molecule. Exemplary LMMs and/or components of the lipid metabolism pathway are listed, but not limited, to those listed in Table 1.

TABLE 1

Lipid Metabolism Pathways and Components/Gene Products Thereof

| Pathway | Component/Gene Product |
| --- | --- |
| Global Lipid Metabolism Regulators | SREBF1 (sterol regulatory element-binding transcription factor 1) |
| | SREBF2 (sterol regulatory element-binding transcription factor 2) |
| | PRMT5 |
| De Novo Lipogenesis | FAS (fatty acid synthase) |
| | ACC (acetyl-coA carboxylase) |
| | ACL (ATP citrate lyase) |
| Fatty Acid Re-esterification | DGAT (diglyceride acyltransferase) |
| | GPAT (glycerol 3-phosphate acyltransferase) |
| | LPL (lipoprotein lipase) |
| Phospholipid Biosynthesis | AGPAT (1-actyl-sn-glycerol-3-phosphate O-acyltransferase) |
| | AGNPR (acyl/alkylglycerone-phosphate reductase) |
| | CCT (phosphocholine cytidyltransferase) |
| | CDS (phosphatidate cytidylyltransferase) |
| | CEPT (diacylglycerol choline/ehtanolaminephosphotransferase) |
| | CERT (ceramide transfer protein) |
| | CGT (N-acylsphingosine galactosyltransferase) |
| | CPT (diacylglycerol cholinephosphotransferase) |
| | CLS (cardiolipin synthase) |
| | CRD (ceramidase) |
| | GNPAT (glycerone-phosphate O-acyltransferase) |
| | KDSR (3-ketosphinganine reductase) |

TABLE 1-continued

Lipid Metabolism Pathways and Components/Gene Products Thereof

| Pathway | Component/Gene Product |
|---|---|
|  | LCS (polypeptide N-acetylgalactosaminyltransferase) |
|  | PAP (phosphatidic acid phosphatase) |
|  | PEMT (phosphatidylethanolamine N-methyltransferase) |
|  | PGP (phosphatidylglycerophosphatase) |
|  | PGS (CDP-diacylglycerol-glycerol-3-phosphate 3-phosphatidyltransferase) |
|  | PIS (CDP-diacylglycerol-inositol 3-phosphatidyltransferase) |
|  | PSD (phosphatidylserine decarboxylase) |
|  | PSS1 (phosphatidylserine synthase 1) |
|  | PSS2 (phosphatidylserine synthase 2) |
|  | SGMS (ceramide choline phosphotransferase) |
|  | SNAT (sphingosine N-acyltransferase) |
|  | SPK (sphinganine kinase) |
|  | SPP (sphingosine-1-phosphate phosphatase) |
|  | SPT (serine Co-palmitoyltransferase) |
| Fatty Acid Desaturation | SCD1 (stearoyl CoA desaturase-1) |
|  | SCD2 (stearoyl CoA desaturase-2) |
|  | SCD3 (stearoyl CoA desaturase-3) |
|  | SCD4 (stearoyl CoA desaturase-4) |
|  | SCD5 (Steoryl CoA desaturase-5) |
|  | PED (plasmanylethanolamine desaturase) |
| Regulation of SREBF1 and other pathways | S1P (site-1 protease) |
|  | S2P (site-2 protease) |
|  | SCAP (SREBF cleavage-activating protein) |
|  | INSIG1 (insulin induced gene 1) |
|  | INSIG2 (insulin induced gene 2) |
|  | HMG CoA reductase (2-hydroxy-3-methylgulatryl-CoA reductase) |
|  | PPAR receptors, e.g., PPARα, PPARγ |

In one embodiment, the LMM comprises at least 50%, 55%, 60%, 65%, 70%, 75%, 80%, 85%, 90%, 95%, 96%, 97%, 98%, 99%, or 100% amino acid sequence identity or homology with a component, e.g., gene product, involved in a lipid metabolism pathway, e.g., provided in Table 1; or differs by 1, 2, or 3 or more amino acid residues but no more than 50, 40, 30, 20, 15, or 10 amino acid residues from the amino acid sequence of a component, e.g., gene product, involved in the lipid metabolism pathway, e.g., provided in Table 1.

In one embodiment, the LMM comprises a functional fragment of a component involved in the lipid metabolism pathway, e.g., provided in Table 1. A functional fragment of an LMM as described herein may comprise one or more functional domains of the LMM. By way of example, a functional fragment of a LMM that is a transcription factor comprises a DNA binding domain and a transactivation domain. By way of example, a functional fragment of a LMM that is an enzyme comprises a domain with enzymatic activity. A functional fragment of an LMM as described herein retains functional activity, e.g., at least 5%, 10%, 20%, 30%, 40%, 50%, 60%, 70%, 80%, or 90% of the functional activity, of the full-length LMM. Functional fragments of an LMM can be experimentally determined by one skilled in the art, or can be predicted using algorithms based on sequence homology of functional domains. Exemplary LMMs are further described below.

In any of the embodiments of the methods described herein, the LMM is a transcriptional regulator. In one embodiment, the LMM is a transcription factor or transcriptional activator, that binds to the DNA or associates in a complex that binds to DNA, and recruits or associates in a complex that recruits RNA polymerase for transcription of one or more gene products involved in lipid metabolism. In one embodiment, the LMM binds to a sterol binding element and/or E-box promoter sequences. In one embodiment, the LMM comprises sterol regulatory element binding factor 1 (SREBF1) or sterol regulatory element binding factor 2 (SREBF2) or a functional fragment or isoform thereof.

In an embodiment, the LMM comprises a global transcriptional activator or transcription factor. In one embodiment, the LMM is capable of modulating the transcription of two or more, e.g., two, three, four, five, six, or more, components of a lipid metabolism pathway, e.g., as provided in Table 1. In another embodiment, the LMM is capable of modulating the transcription of one or more, e.g., one, two, three, four, or five, or more, components of two or more lipid metabolism pathways, e.g., components and pathways as provided in Table 1.

Sterol regulatory element binding factor 1 (SREBF1) is a global transcriptional activator which upregulates the transcription of genes involved in lipogenesis, fatty acid re-esterification, fatty acid desaturation and elongation, and phospholipid biosynthesis by binding to sterol regulatory element (SRE) and E-box promoter sequences (Hagen, Rodriguez-Cuenca et al. 2010) present in the promoter regions of target genes. Transcription of the SREBF1 gene itself is endogenously regulated by the presence of the sterol regulatory element (SRE) amongst other transcriptional regulating elements in the promoter region of the gene. On top of this, a multitude of posttranslational regulating mechanisms including phosphorylation, ubiquitination, sumoylation, acetylation, fatty acid-mediated modifications and proteolytic processing make for a tightly controlled but adaptable homeostatic system fixed around SREBF1.

Full-length SREBF1 is synthesized and localizes primarily to the endoplasmic reticulum (ER). Membrane integral SREBF1 forms a complex with SREBF cleavage-activating protein (SCAP) which can facilitate migration of SREBF1 to the Golgi. However, when high sterol levels (particularly cholesterol) are present, a conformational change in SCAP is induced which aids binding to the membrane integral protein insig (insulin induced gene), thus inhibiting migration of this complex. In the absence of sterols, insig does not bind to SCAP, therefore allowing COPII mediated vesicle formation, and subsequent migration of the SREBF:SCAP complex to the Golgi. Sequential proteolytic cleavage occurs in the Golgi mediated by site-1 protease (S1P) and site-2 protease (S2P) proteins liberating the N-terminal basic helix loop helix leucine zipper (bHLHlz) of SREBF1 which is immediately present in the cytoplasm, but migrates to the nucleus. Lysine residues present on the cleaved SREBF1 are ubiquitinated and degraded by the 26S proteasome but this ubiquitination can be inhibited through acetylation of the lysine residues which allows migration to the nucleus. Finally, nuclear SREBF1 can bind to sterol regulatory element (SRE) sequences upstream of a number of genes responsible for de novo lipogenesis (fatty acid synthase (FAS) and acetyl coA carboxylase (ACC)), fatty acid re-esterfication (diacylglycerol acyltransferase (DGAT), glycerol-3-phosphate (GPAT) and lipoprotein lipase (LPL)), phospholipid biosynthesis (CTP:phosphocholine cytidylyl-transferase (CCT)), fatty acid desaturation (stearoyl-coA desaturase 1 (SCD1)). Nuclear SREBF1 is also capable of activating transcription of the full length SREBF1 gene itself, but this is also dependent on activation of the liver X receptor (LXR) promoter sequence also located upstream of the gene (Brown, Goldstein 1997-BROWN, M. S. and GOLDSTEIN, J. L., 1997. The SREBP Pathway: Regulation of Cholesterol Metabolism by Proteolysis of a Membrane-Bound Transcription Factor. Cell, 89(3), pp. 331-340) (Hagen, Rodriguez-Cuenca-HAGEN, R. M., RODRIGUEZ-CUENCA, S. and VIDAL-PUIG, A., 2010. An allostatic control of membrane lipid composition by SREBP1. FEBS letters, 584(12), pp. 2689-2698).

In one embodiment, the LMM comprises SREBF1, an isoform, or a functional fragment thereof. The amino acid sequence for SREBF1 is provided below:

(SEQ ID NO: 1)
MDELAFGEAALEQTLAEMCELDTAVLNDIEDMLQLINNQDSDFPGLFDAP

YAGGETGDTGPSSPGANSPESFSSASLASSLEAFLGGPKVTPAPLSPPPS

APAALKMYPSVSPFSPGPGIKEEPVPLTILQPAAPQPSPGTLLPPSFPAP

PVQLSPAPVLGYSSLPSGFSGTLPGNTQQPPSSLPLAPAPGVLPTPALHT

QVQSLASQQPLPASAAPRTNTVTSQVQQVPVVLQPHFIKADSLLLTAVKT

DAGATVKTAGISTLAPGTAVQAGPLQTLVSGGTILATVPLVVDTDKLPIH

RLAAGSKALGSAQSRGEKRTAHNAIEKRYRSSINDKIVELKDLVVGTEAK

LNKSAVLRKAIDYIRFLQHSNQKLKQENLTLRSAHKSKSLKDLVSACGSG

GGTDVSMEGMKPEVVETLTPPPSDAGSPSQSSPLSFGSRASSSGGSDSEP

DSPAFEDSQVKAQRLPSHSRGMLDRSRLALCVLAFLCLTCNPLASLFGWG

ILTPSDATGTHRSSGRSMLEAESRDGSNWTQWLLPPLVWLANGLLVLACL

ALLFVYGEPVTRPHSGPAVHFWRHRKQADLDLARGDFPQAAQQLWLALQA

LGRPLPTSNLDLACSLLWNLIRHLLQRLWVGRWLAGQAGGLLRDRGLRKD

ARASARDAAVVYHKLHQLHAMGKYTGGHLAASNLALSALNLAECAGDAIS

MATLAEIYVAAALRVKTSLPRALHFLTRFFLSSARQACLAQSGSVPLAMQ

WLCHPVGHRFFVDGDWAVHGAPPESLYSVAGNPVDPLAQVTRLFREHLLE

RALNCIAQPSPGAADGDREFSDALGYLQLLNSCSDAAGAPACSFSVSSSM

AATTGPDPVAKWWASLTAVVIHWLRRDEEAAERLYPLVEHIPQVLQDTER

PLPRAALYSFKAARALLDHRKVESSPASLAICEKASGYLRDSLASTPTGS

SIDKAMQLLLCDLLLVARTSLWQRQQSPASVQVAHGTSNGPQASALELRG

FQHDLSSLRRLAQSFRPAMRRVFLHEATARLMAGASPARTHQLLDRSLRR

RAGSSGKGGTTAELEPRPTWREHTEALLLASCYLPPAFLSAPGQRMSMLA

EAARTVEKLGDHRLLLDCQQMLLRLGGGTTVTSS.

The nucleotide sequence for SREBF1 is provided below:

(SEQ ID NO: 2)
atggacgagctggccttcggtgaggcggctctggaacagacactggccga gatgtgcgaactggacacagcggttttgaacgacatcgaagacatgctcc agctcatcaacaaccaagacagtgactttcccgggcctgtttgacgcccc tatgctgggggtgagacaggggacacaggccccagcagcccaggtgccaa ctctcctgagagcttctcttctgcttctctggcctcctctctggaagcct tcctgggaggacccaaggtgacacctgcacccttgtccctccaccatcg gcacccgctgctttaaagatgtacccgtccgtgtccccttttcccctgg gcctgggatcaaagaggagccagtgccactcaccatcctacagcctgcag cgccacagccgtcaccggggaccctcctgcctccgagcttccccgcacca cccgtacagctcagccctgcgcccgtgctgggttactcgagcctgccttc aggcttctcagggaccctccaggaaacactcagcagccaccatctagcc tgccgctggcccctgcaccaggagtcttgcccacccctgccctgcacacc caggtccaaagcttggcctcccagcagccgctgccagcctcagcagcccc tagaacaaacactgtgacctcacaggtccagcaggtcccagttgtactgc agccacacttcatcaaggcagactcactgctgctgacagctgtgaagaca gatgcaggagccaccgtgaagactgcaggcatcagcaccctggctcctgg cacagccgtgcaggcaggtcccctgcagaccctggtgagtggagggacca tcttggccacagtacctttggttgtggacacagacaaactgcccatccac cgactcgcagctggcagcaaggccctaggctcagctcagagccgtggtga gaagcgcacagcccacaatgccattgagaagcgctaccggtcttctatca atgacaagattgtggagctcaaagacctggtggtgggcactgaagcaaag ctgaataaatctgctgtcttgcgcaaggccatcgactacatccgcttctt gcagcacagcaaccagaagctcaagcaggagaacctgaccctacgaagtg cacacaaaagcaaatcactgaaggacctggtgtcagcttgtggcagtgga ggaggcacagatgtgtctatggagggcatgaaacccgaagtggtggagac gcttacccctccaccctcagacgccggctcaccctcccagagtagcccct tgtcttttggcagcagagctagcagcagtggtggtagtgactctgagccc gacagtccagcctttgaggatagccaggtcaaagcccagcggctgccttc acacagccgaggcatgctggaccgctcccgcctggccctgtgtgtactgg cctttctgtgtctgacctgcaatcctttggcctcgcttttcggctgggc attctcactccctctgatgctacgggtacacaccgtagttctgggcgcag catgctggaggcagagagcagagatggctctaattggacccagtggttgc -continued

```
tgccaccoctagtctggctggccaatggactactagtgttggcctgcttg
gctcttctctttgtctatggggaacctgtgactaggccacactctggccc
ggctgtacacttctggagacatcgcaaacaagctgacctggatttggccc
ggggagatttccccaggctgctcaacagctgtggctggccctgcaagcg
ctgggccggccctgcccacctcaaacctggatctggcctgcagtctgct
ttggaacctcatccgccacctgctccagcgtctctgggtgggccgctggc
tggcaggccaggccgggggcctgctgagggaccgtgggctgaggaaggat
gcccgtgccagtgcccgggatgcggctgttgtctaccataagctgcacca
gctgcatgccatgggcaagtacacaggaggacatcttgctgcttctaacc
tggcactaagtgccctcaacctggctgagtgcgcaggagatgctatctcc
atggcaacactggcagagatctatgtggcagcggccctgagggtcaaaac
cagcctcccaagagccctgcacttcttgacacgtttcttcctgagcagcg
cccgccaggcctgcctagcacagagcggctcggtgcctcttgccatgcag
tggctctgccaccctgtaggtcaccgtttctttgtggacggggactgggc
cgtgcacggtgccccccgagagcctgtacagcgtggctgggaacccag
tggatccgctggcccaggtgacccggctattccgtgaacatctcctagag
cgagcgttgaactgtattgctcagcccagcccaggggcagctgacggaga
cagggagttctcagatgcccttggatatctgcagttgctaaatagctgtt
ctgatgctgccggggctcctgcttgcagtttctctgtcagctccagcatg
gctgccaccactggcccagaccagtggccaagtggtgggcctcactgac
agctgtggtgatccactggctgaggcgggatgaagaggcagctgagcgct
tgtacccactggtagagcatatcccccaggtgctgcaggacactgagaga
cccctgccagggcagctctgtactccttcaaggctgcccgggctctgct
ggaccacagaaaggtggaatctagcccagccagcctggccatctgtgaga
aggccagtgggtacctgcgggacagcttagcctctacaccaactggcagt
tccattgacaaggccatgcagctgctcctgtgtgatctacttcttgtggc
ccgtaccagtctgtggcagcggcagcagtcaccagcttcagtccaggtag
ctcacggtaccagcaatggaccccaggcctctgctctggagctgcgtggt
ttccaacatgacctgagcagcctgcggcggttggcacagagcttccggcc
tgctatgaggagggtattcctacatgaggccacagctcggctgatggcag
gagcaagtcctgcccggacacaccagctcctggatcgcagtctgaggagg
agggcaggttccagtggcaaaggaggcactacagctgagctggagccacg
gcccacatggcgggagcacaccgaggccctgctgttggcatcctgctatc
tgcccctgccttcctgtcggctcctgggcagcgaatgagcatgctggcc
gaggcggcacgcaccgtagagaagcttggcgatcaccggctactgctgga
ctgccagcagatgctcctgcgcctgggcggcggaaccaccgtcacttcca
gctag.
```

In one embodiment, the LMM comprises at least 50%, 55%, 60%, 65%, 70%, 75%, 80%, 85%, 90%, 95%, 96%, 97%, 98%, 99%, or 100% identity with the amino acid sequence of SREBF1; e.g., SEQ ID NO: 1; or differs by 1, 2, or 3 or more amino acid residues but no more than 50, 40, 30, 20, 15, or 10 amino acid residues from the amino acid sequence of SREBF1, e.g., SEQ ID NO: 1.

Isoforms of SREBF1 are known in the art, and include isoform a and isoform b, as well as species or cell specific, e.g., CHO cell specific, isoforms, such as isoform c. The amino acid sequence for SREBF1 isoform a (GenBank Accession No. NP_001005291.2) is provided below.

```
                                    (SEQ ID NO: 28)
MDEPPFSEAALEQALGEPCDLDAALLTDIEGEVGAGRGRANGLDAPRAGA

DRGAMDCTFEDMLQLINNQDSDFPGLFDPPYAGSGAGGTDPASPDTSSPG

SLSPPPATLSSSLEAFLSGPQAAPSPLSPPQPAPTPLKMYPSMPAFSPGP

GIKEESVPLSILQTPTPQPLPGALLPQSFPAPAPPQFSSTPVLGYPSPPG

GFSTGSPPGNTQQPLPGLPLASPPGVPPVSLHTQVQSVVPQQLLTVTAAP

TAAPVTTTVTSQIQQVPVLLQPHFIKADSLLLTAMKTDGATVKAAGLSPL

VSGTTVQTGPLPTLVSGGTILATVPLVVDAEKLPINRLAAGSKAPASAQS

RGEKRTAHNAIEKRYRSSINDKIIELKDLVVGTEAKLNKSAVLRKAIDYI

RFLQHSNQKLKQENLSLRTAVHKSKSLKDLVSACGSGGNTDVLMEGVKTE

VEDTLTPPPSDAGSPFQSSPLSLGSRGSGSGGSGSDSEPDSPVFEDSKAK

PEQRPSLHSRGMLDRSRLALCTLVFLCLSCNPLASLLGARGLPSPSDTTS

VYHSPGRNVLGTESRDGPGWAQWLLPPVVWLLNGLLVLVSLVLLFVYGEP

VTRPHSGPAVYFWRHRKQADLDLARGDFAQAAQQLWLALRALGRPLPTSH

LDLACSLLWNLIRHLLQRLWVGRWLAGRAGGLQQDCALRVDASASARDAA

LVYHKLHQLHTMGKHTGGHLTATNLALSALNLAECAGDAVSVATLAEIYV

AAALRVKTSLPRALHFLTRFFLSSARQACLAQSGSVPPAMQWLCHPVGHR

FFVDGDWSVLSTPWESLYSLAGNPVDPLAQVTQLFREHLLERALNCVTQP

NPSPGSADGDKEFSDALGYLQLLNSCSDAAGAPAYSFSISSSMATTTGVD

PVAKWWASLTAVVIHWLRRDEEAAERLCPLVEHLPRVLQESERPLPRAAL

HSFKAARALLGCAKAESGPASLTICEKASGYLQDSLATTPASSSIDKAVQ

LFLCDLLLVVRTSLWRQQQPPAPAPAAQGTSSRPQASALELRGFQRDLSS

LRRLAQSFRPAMRRVFLHEATARLMAGASPTRTHQLLDRSLRRRAGPGGK

GGAVAELEPRPTRREHAEALLLASCYLPPGFLSAPGQRVGMLAEAARTLE

KLGDRRLLHDCQQMLMRLGGGTTVTSS
```

The nucleic acid sequence, or mRNA sequence, for SREBF1 isoform a (GenBank Accession No. NM_001005291.2) is provided below.

```
                                    (SEQ ID NO: 29)
AGCAGAGCTGCGGCCGGGGGAACCCAGTTTCCGAGGAACTTTTCGCCGGC

GCCGGGCCGCCTCTGAGGCCAGGGCAGGACACGAACGCGCGGAGCGGCGG

CGGCGACTGAGAGCCGGGGCCGCGGCGGCGCTCCCTAGGAAGGGCCGTAC

GAGGCGGCGGGCCCGGCGGGCCTCCCGGAGGAGGCGGCTGCGCCATGGAC

GAGCCACCCTTCAGCGAGGCGGCTTTGGAGCAGGCGCTGGGCGAGCCGTG

CGATCTGGACGCGGCGCTGCTGACCGACATCGAAGGTGAAGTCGGCGCGG

GGAGGGGTAGGGCCAACGGCCTGGACGCCCCAAGGGCGGGCGCAGATCGC

GGAGCCATGGATTGCACTTTCGAAGACATGCTTCAGCTTATCAACAACCA

AGACAGTGACTTCCCTGGCCTATTTGACCCACCCTATGCTGGGAGTGGGG
```

-continued

```
CAGGGGGCACAGACCCTGCCAGCCCCGATACCAGCTCCCCAGGCAGCTTG
TCTCCACCTCCTGCCACATTGAGCTCCTCTCTTGAAGCCTTCCTGAGCGG
GCCGCAGGCAGCGCCCTCACCCCTGTCCCCTCCCCAGCCTGCACCCACTC
CATTGAAGATGTACCCGTCCATGCCCGCTTTCTCCCCTGGGCCTGGTATC
AAGGAAGAGTCAGTGCCACTGAGCATCCTGCAGACCCCCACCCCACAGCC
CCTGCCAGGGGCCCTCCTGCCACAGAGCTTCCCAGCCCCAGCCCCACCGC
AGTTCAGCTCCACCCCTGTGTTAGGCTACCCCAGCCCTCCGGGAGGCTTC
TCTACAGGAAGCCCTCCCGGGAACACCCAGCAGCCGCTGCCTGGCCTGCC
ACTGGCTTCCCCGCCAGGGGTCCCGCCCGTCTCCTTGCACACCCAGGTCC
AGAGTGTGGTCCCCAGCAGCTACTGACAGTCACAGCTGCCCCCACGGCA
GCCCCTGTAACGACCACTGTGACCTCGCAGATCCAGCAGGTCCCGGTCCT
GCTGCAGCCCCACTTCATCAAGGCAGACTCGCTGCTTCTGACAGCCATGA
AGACAGACGGAGCCACTGTGAAGGCGGCAGGTCTCAGTCCCCTGGTCTCT
GGCACCACTGTGCAGACAGGGCCTTTGCCGACCCTGGTGAGTGGCGGAAC
CATCTTGGCAACAGTCCCACTGGTCGTAGATGCGGAGAAGCTGCCTATCA
ACCGGCTCGCAGCTGGCAGCAAGGCCCCGGCCTCTGCCCAGAGCCGTGGA
GAGAAGCGCACAGCCCACAACGCCATTGAGAAGCGCTACCGCTCCTCCAT
CAATGACAAAATCATTGAGCTCAAGGATCTGGTGGTGGGCACTGAGGCAA
AGCTGAATAAATCTGCTGTCTTGCGCAAGGCCATCGACTACATTCGCTTT
CTGCAACACAGCAACCAGAAACTCAAGCAGGAGAACCTAAGTCTGCGCAC
TGCTGTCCACAAAAGCAAATCTCTGAAGGATCTGGTGTCGGCCTGTGGCA
GTGGAGGGAACACAGACGTGCTCATGGAGGGCGTGAAGACTGAGGTGGAG
GACACACTGACCCCACCCCCCTCGGATGCTGGCTCACCTTTCCAGAGCAG
CCCCTTGTCCCTTGGCAGCAGGGGCAGTGGCAGCGGTGGCAGTGGCAGTG
ACTCGGAGCCTGACAGCCCAGTCTTTGAGGACAGCAAGGCAAAGCCAGAG
CAGCGGCCGTCTCTGCACAGCCGGGGCATGCTGGACCGCTCCCGCCTGGC
CCTGTGCACGCTCGTCTTCCTCTGCCTGTCCTGCAACCCCTTGGCCTCCT
TGCTGGGGCCCGGGGCTTCCCAGCCCCTCAGATACCACCAGCGTCTAC
CATAGCCCTGGGCGCAACGTGCTGGGCACCGAGAGCAGAGATGGCCCTGG
CTGGGCCCAGTGGCTGCTGCCCCAGTGGTCTGGCTGCTCAATGGGCTGT
TGGTGCTCGTCTCCTTGGTGCTTCTCTTTGTCTACGGTGAGCCAGTCACA
CGGCCCCACTCAGGCCCCGCCGTGTACTTCTGGAGGCATCGCAAGCAGGC
TGACCTGGACCTGGCCCGGGGAGACTTTGCCCAGGCTGCCCAGCAGCTGT
GGCTGGCCCTGCGGGCACTGGGCCGGCCCCTGCCCACCTCCCACCTGGAC
CTGGCTTGTAGCCTCCTCTGGAACCTCATCCGTCACCTGCTGCAGCGTCT
CTGGGTGGGCCGCTGGCTGGCAGGCCGGGCAGGGGGCCTGCAGCAGGACT
GTGCTCTGCGAGTGGATGCTAGCGCCAGCGCCCGAGACGCAGCCCTGGTC
TACCATAAGCTGCACCAGCTGCACACCATGGGGAAGCACACAGGCGGGCA
CCTCACTGCCACCAACCTGGCGCTGAGTGCCCTGAACCTGGCAGAGTGTG
CAGGGGATGCCGTGTCTGTGGCGACGCTGGCCGAGATCTATGTGGCGGCT
GCATTGAGAGTGAAGACCAGTCTCCCACGGGCCTTGCATTTTCTGACACG
```

-continued

```
CTTCTTCCTGAGCAGTGCCCGCCAGGCCTGCCTGGCACAGAGTGGCTCAG
TGCCTCCTGCCATGCAGTGGCTCTGCCACCCCGTGGGCCACCGTTTCTTC
GTGGATGGGGACTGGTCCGTGCTCAGTACCCCATGGGAGAGCCTGTACAG
CTTGGCCGGGAACCCAGTGGACCCCCTGGCCCAGGTGACTCAGCTATTCC
GGGAACATCTCTTAGAGCGAGCACTGAACTGTGTGACCCAGCCCAACCCC
AGCCCTGGGTCAGCTGATGGGGACAAGGAATTCTCGGATGCCCTCGGGTA
CCTGCAGCTGCTGAACAGCTGTTCTGATGCTGCGGGGCTCCTGCCTACA
GCTTCTCCATCAGTTCCAGCATGGCCACCACCACCGGCGTAGACCCGGTG
GCCAAGTGGTGGGCCTCTCTGACAGCTGTGGTGATCCACTGGCTGCGGCG
GGATGAGGAGGCGGCTGAGCGGCTGTGCCCGCTGGTGGAGCACCTGCCCC
GGGTGCTGCAGGAGTCTGAGAGACCCCTGCCCAGGGCAGCTCTGCACTCC
TTCAAGGCTGCCCGGGCCCTGCTGGGCTGTGCCAAGGCAGAGTCTGGTCC
AGCCAGCCTGACCATCTGTGAGAAGGCCAGTGGGTACCTGCAGGACAGCC
TGGCTACCACACCAGCCAGCAGCTCCATTGACAAGGCCGTGCAGCTGTTC
CTGTGTGACCTGCTTCTTGTGGTGCGCACCAGCCTGTGGCGGCAGCAGCA
GCCCCCGGCCCCGGCCCCAGCAGCCCAGGGCACCAGCAGCAGGCCCCAGG
CTTCCGCCCTTGAGCTGCGTGGCTTCCAACGGGACCTGAGCAGCCTGAGG
CGGCTGGCACAGAGCTTCCGGCCCGCCATGCGGAGGGTGTTCCTACATGA
GGCCACGGCCCGGCTGATGGCGGGGGCCAGCCCCACACGGACACACCAGC
TCCTCGACCGCAGTCTGAGGCGGCGGCAGGCCCCGGTGGCAAAGGAGGC
GCGGTGGCGGAGCTGGAGCCGCGGCCCACGCGGCGGGAGCACGCGGAGGC
CTTGCTGCTGGCCTCCTGCTACCTGCCCCCCGGCTTCCTGTCGGCGCCCG
GGCAGCGCGTGGGCATGCTGGCTGAGGCGGCGCGCACACTCGAGAAGCTT
GGCGATCGCCGGCTGCTGCACGACTGTCAGCAGATGCTCATGCGCCTGGG
CGGTGGGACCACTGTCACTTCCAGCTAGACCCCGTGTCCCCGGCCTCAGC
ACCCCTGTCTCTAGCCACTTTGGTCCCGTGCAGCTTCTGTCCTGCGTCGA
AGCTTTGAAGGCCGAAGGCAGTGCAAGAGACTCTGGCCTCCACAGTTCGA
CCTGCGGCTGCTGTGTGCCTTCGCGGTGGAAGGCCCGAGGGGCGCGATCT
TGACCCTAAGACCGGCGGCCATGATGGTGCTGACCTCTGGTGGCCGATCG
GGGCACTGCAGGGGCCGAGCCATTTTGGGGGGCCCCCCTCCTTGCTCTGC
AGGCACCTTAGTGGCTTTTTTCCTCCTGTGTACAGGGAAGAGAGGGGTAC
ATTTCCCTGTGCTGACGGAAGCCAACTTGGCTTTCCCGGACTGCAAGCAG
GGCTCTGCCCCAGAGGCCTCTCTCTCCGTCGTGGGAGAGAGACGTGTACA
TAGTGTAGGTCAGCGTGCTTAGCCTCCTGACCTGAGGCTCCTGTGCTACT
TTGCCTTTTGCAAACTTTATTTTCATAGATTGAGAAGTTTTGTACAGAGA
ATTAAAAATGAAATTATTTATAATCTGGGTTTTGTGTCTTCAGCTGATGG
ATGTGCTGACTAGTGAGAGTGCTTGGGCCCTCCCCCAGCACCTAGGGAAA
GGCTTCCCCTCCCCCTCCGGCCACAAGGTACACAACTTTTAACTTAGCTC
TTCCCGATGTTTGTTTGTTAGTGGGAGGAGTGGGGAGGGCTGGCTGTATG
GCCTCCAGCCTACCTGTTCCCCCTGCTCCCAGGGCACATGGTTGGGCTGT
```

```
GTCAACCCTTAGGGCCTCCATGGGGTCAGTTGTCCCTTCTCACCTCCCAG

CTCTGTCCCCATCAGGTCCCTGGGTGGCACGGGAGGATGGACTGACTTCC

AGGACCTGTTGTGTGACAGGAGCTACAGCTTGGGTCTCCCTGCAAGAAGT

CTGGCACGTCTCACCTCCCCCATCCCGGCCCCTGGTCATCTCACAGCAAA

GAAGCCTCCTCCCTCCCGACCTGCCGCCACACTGGAGAGGGGGCACAGGG

GCGGGGGAGGTTTCCTGTTCTGTGAAAGGCCGACTCCCTGACTCCATTCA

TGCCCCCCCCCCAGCCCCTCCCTTCATTCCCATTCCCCAACCTAAAGCC

TGGCCCGGCTCCCAGCTGAATCTGGTCGGAATCCACGGGCTGCAGATTTT

CCAAAACAATCGTTGTATCTTTATTGACTTTTTTTTTTTTTTTTCTGA

ATGCAATGACTGTTTTTTACTCTTAAGGAAAATAAACATCTTTTAGAAAC

AAAAAAAAAAAA
```

The amino acid sequence for SREBF1 isoform b (GenBank Accession No. NP_004167.3) is provided below.

```
                                                (SEQ ID NO: 30)
MDEPPFSEAALEQALGEPCDLDAALLTDIEDMLQLINNQDSDFPGLFDPP

YAGSGAGGTDPASPDTSSPGSLSPPPATLSSSLEAFLSGPQAAPSPLSPP

QPAPTPLKMYPSMPAFSPGPGIKEESVPLSILQTPTPQPLPGALLPQSFP

APAPPQFSSTPVLGYPSPPGGFSTGSPPGNTQQPLPGLPLASPPGVPPVS

LHTQVQSVVPQQLLTVTAAPTAAPVTTTVTSQIQQVPVLLQPHFIKADSL

LLTAMKTDGATVKAAGLSPLVSGTTVQTGPLPTLVSGGTILATVPLVVDA

EKLPINRLAAGSKAPASAQSRGEKRTAHNAIEKRYRSSINDKIIELKDLV

VGTEAKLNKSAVLRKAIDYIRFLQHSNQKLKQENLSLRTAVHKSKSLKDL

VSACGSGGNTDVLMEGVKTEVEDTLTPPPSDAGSPFQSSPLSLGSRGSGS

GGSGSDSEPDSPVFEDSKAKPEQRPSLHSRGMLDRSRLALCTLVFLCLSC

NPLASLLGARGLPSPSDTTSVYHSPGRNVLGTESRDGPGWAQWLLPPVVW

LLNGLLVLVSLVLLFVYGEPVTRPHSGPAVYFWRHRKQADLDLARGDFAQ

AAQQLWLALRALGRPLPTSHLDLACSLLWNLIRHLLQRLWVGRWLAGRAG

GLQQDCALRVDASASARDAALVYHKLHQLHTMGKHTGGHLTATNLALSAL

NLAECAGDAVSVATLAEIYVAAALRVKTSLPRALHFLTRFFLSSARQACL

AQSGSVPPAMQWLCHPVGHRFFVDGDWSVLSTPWESLYSLAGNPVDPLAQ

VTQLFREHLLERALNCVTQPNPSPGSADGDKEFSDALGYLQLLNSCSDAA

GAPAYSFSISSSMATTTGVDPVAKWWASLTAVVIHWLRRDEEAAERLCPL

VEHLPRVLQESERPLPRAALHSFKAARALLGCAKAESGPASLTICEKASG

YLQDSLATTPASSSIDKAVQLFLCDLLLVVRTSLWRQQQPPAPAPAAQGT

SSRPQASALELRGFQRDLSSLRRLAQSFRPAMRRVFLHEATARLMAGASP

TRTHQLLDRSLRRRAGPGGKGGAVAELEPRPTRREHAEALLLASCYLPPG

FLSAPGQRVGMLAEAARTLEKLGDRRLLHDCQQMLMRLGGGTTVTSS
```

The nucleic acid sequence, or mRNA sequence, for SREBF1 isoform b (GenBank Accession No. NM_004176.4) is provided below.

```
                                                (SEQ ID NO: 31)
AGCAGAGCTGCGGCCGGGGGAACCCAGTTTCCGAGGAACTTTTCGCCGGC

GCCGGGCCGCCTCTGAGGCCAGGGCAGGACACGAACGCGCGGAGCGGCGG

CGGCGACTGAGAGCCGGGGCCGCGGCGGCGCTCCCTAGGAAGGGCCGTAC

GAGGCGGCGGGCCCGGCGGGCCTCCCGGAGGAGGCGGCTGCGCCATGGAC

GAGCCACCCTTCAGCGAGGCGGCTTTGGAGCAGGCGCTGGGCGAGCCGTG

CGATCTGGACGCGGCGCTGCTGACCGACATCGAAGACATGCTTCAGCTTA

TCAACAACCAAGACAGTGACTTCCCTGGCCTATTTGACCCACCCTATGCT

GGGAGTGGGGCAGGGGGCACAGACCCTGCCAGCCCCGATACCAGCTCCCC

AGGCAGCTTGTCTCCACCTCCTGCCACATTGAGCTCCTCTCTTGAAGCCT

TCCTGAGCGGGCCGCAGGCAGCGCCCTCACCCCTGTCCCCTCCCCAGCCT

GCACCCACTCCATTGAAGATGTACCCGTCCATGCCCGCTTTCTCCCCTGG

GCCTGGTATCAAGGAAGAGTCAGTGCCACTGAGCATCCTGCAGACCCCCA

CCCCACAGCCCCTGCCAGGGGCCCTCCTGCCACAGAGCTTCCCAGCCCCA

GCCCCACCGCAGTTCAGCTCCACCCCTGTGTTAGGCTACCCCAGCCCTCC

GGGAGGCTTCTCTACAGGAAGCCCTCCCGGGAACACCCAGCAGCCGCTGC

CTGGCCTGCCACTGGCTTCCCCGCCAGGGGTCCCGCCCGTCTCCTTGCAC

ACCCAGGTCCAGAGTGTGGTCCCCCAGCAGCTACTGACAGTCACAGCTGC

CCCCACGGCAGCCCCTGTAACGACCACTGTGACCTCGCAGATCCAGCAGG

TCCCGGTCCTGCTGCAGCCCCACTTCATCAAGGCAGACTCGCTGCTTCTG

ACAGCCATGAAGACAGACGGAGCCACTGTGAAGGCGGCAGGTCTCAGTCC

CCTGGTCTCTGGCACCACTGTGCAGACAGGGCCTTTGCCGACCCTGGTGA

GTGGCGGAACCATCTTGGCAACAGTCCCACTGGTCGTAGATGCGGAGAAG

CTGCCTATCAACCGGCTCGCAGCTGGCAGCAAGGCCCCGGCCTCTGCCCA

GAGCCGTGGAGAGAAGCGCACAGCCCACAACGCCATTGAGAAGCGCTACC

GCTCCTCCATCAATGACAAAATCATTGAGCTCAAGGATCTGGTGGTGGGC

ACTGAGGCAAAGCTGAATAAATCTGCTGTCTTGCGCAAGGCCATCGACTA

CATTCGCTTTCTGCAACACAGCAACCAGAAACTCAAGCAGGAGAACCTAA

GTCTGCGCACTGCTGTCCACAAAAGCAAATCTCTGAAGGATCTGGTGTCG

GCCTGTGGCAGTGGAGGGAACACAGACGTGCTCATGGAGGGCGTGAAGAC

TGAGGTGGAGGACACACTGACCCCACCCCCCTCGGATGCTGGCTCACCTT

TCCAGAGCAGCCCCTTGTCCCTTGGCAGCAGGGGCAGTGGCAGCGGTGGC

AGTGGCAGTGACTCGGAGCCTGACAGCCCAGTCTTTGAGGACAGCAAGGC

AAAGCCAGAGCAGCGGCCGTCTCTGCACAGCCGGGGCATGCTGGACCGCT

CCCGCCTGGCCCTGTGCACGCTCGTCTTCCTCTGCCTGTCCTGCAACCCC

TTGGCCTCCTTGCTGGGGGCCGGGGGCTTCCCAGCCCCTCAGATACCAC

CAGCGTCTACCATAGCCCTGGGCGCAACGTGCTGGGCACCGAGAGCAGAG

ATGGCCCTGGCTGGGCCCAGTGGCTGCTGCCCCCAGTGGTCTGGCTGCTC

AATGGGCTGTTGGTGCTCGTCTCCTTGGTGCTTCTCTTTGTCTACGGTGA

GCCAGTCACACGGCCCCACTCAGGCCCCGCCGTGTACTTCTGGAGGCATC

GCAAGCAGGCTGACCTGGACCTGGCCCGGGGAGACTTTGCCCAGGCTGCC
```

-continued
```
CAGCAGCTGTGGCTGGCCCTGCGGGCACTGGGCCGGCCCCTGCCCACCTC
CCACCTGGACCTGGCTTGTAGCCTCCTCTGGAACCTCATCCGTCACCTGC
TGCAGCGTCTCTGGGTGGGCCGCTGGCTGGCAGGCCGGGCAGGGGCCTG
CAGCAGGACTGTGCTCTGCGAGTGGATGCTAGCGCCAGCGCCCGAGACGC
AGCCCTGGTCTACCATAAGCTGCACCAGCTGCACACCATGGGGAAGCACA
CAGGCGGGCACCTCACTGCCACCAACCTGGCGCTGAGTGCCCTGAACCTG
GCAGAGTGTGCAGGGGATGCCGTGTCTGTGGCGACGCTGGCCGAGATCTA
TGTGGCGGCTGCATTGAGAGTGAAGACCAGTCTCCCACGGGCCTTGCATT
TTCTGACACGCTTCTTCCTGAGCAGTGCCCGCCAGGCCTGCCTGGCACAG
AGTGGCTCAGTGCCTCCTGCCATGCAGTGGCTCTGCCACCCCGTGGGCCA
CCGTTTCTTCGTGGATGGGACTGGTCCGTGCTCAGTACCCCATGGGAGA
GCCTGTACAGCTTGGCCGGGAACCCAGTGGACCCCCTGGCCCAGGTGACT
CAGCTATTCCGGGAACATCTCTTAGAGCGAGCACTGAACTGTGTGACCCA
GCCCAACCCCAGCCCTGGGTCAGCTGATGGGACAAGGAATTCTCGGATG
CCCTCGGGTACCTGCAGCTGCTGAACAGCTGTTCTGATGCTGCGGGGCT
CCTGCCTACAGCTTCTCCATCAGTTCCAGCATGGCCACCACCACCGGCGT
AGACCCGGTGGCCAAGTGGTGGGCCTCTCTGACAGCTGTGGTGATCCACT
GGCTGCGGCGGGATGAGGAGGCGGCTGAGCGGCTGTGCCCGCTGGTGGAG
CACCTGCCCCGGGTGCTGCAGGAGTCTGAGAGACCCCTGCCCAGGGCAGC
TCTGCACTCCTTCAAGGCTGCCCGGGCCCTGCTGGGCTGTGCCAAGGCAG
AGTCTGGTCCAGCCAGCCTGACCATCTGTGAGAAGGCCAGTGGGTACCTG
CAGGACAGCCTGGCTACCACACCAGCCAGCAGCTCCATTGACAAGGCCGT
GCAGCTGTTCCTGTGTGACCTGCTTCTTTGTGGTGCGCACCAGCCTGTGGC
GGCAGCAGCAGCCCCCGGCCCCGGCCCCAGCAGCCCAGGGCACCAGCAGC
AGGCCCCAGGCTTCCGCCCTTGAGCTGCGTGGCTTCCAACGGGACCTGAG
CAGCCTGAGGCGGCTGGCACAGAGCTTCCGGCCCGCCATGCGGAGGGTGT
TCCTACATGAGGCCACGGCCCGGCTGATGGCGGGGCCAGCCCCACACGG
ACACACCAGCTCCTCGACCGCAGTCTGAGGCGGCGGGCAGGCCCCGGTGG
CAAAGGAGGCGCGGTGGCGGAGCTGGAGCCGCGGCCCACGCGGCGGGAGC
ACGCGGAGGCCTTGCTGCTGGCCTCCTGCTACCTGCCCCCCGGCTTCCTG
TCGGCGCCCGGGCAGCGCGTGGGCATGCTGGCTGAGGCGGCGCGCACACT
CGAGAAGCTTGGCGATCGCCGGCTGCTGCACGACTGTCAGCAGATGCTCA
TGCGCCTGGGCGGTGGGACCACTGTCACTTCCAGCTAGACCCCGTGTCCC
CGGCCTCAGCACCCCTGTCTCTAGCCACTTTGGTCCCGTGCAGCTTCTGT
CCTGCGTCGAAGCTTTGAAGGCCGAAGGCAGTGCAAGAGACTCTGGCCTC
CACAGTTCGACCTGCGGCTGCTGTGTGCCTTCGCGGTGGAAGGCCCGAGG
GGCGCGATCTTGACCCTAAGACCGGCGGCCATGATGGTGCTGACCTCTGG
TGGCCGATCGGGGCACTGCAGGGGCCGAGCCATTTTGGGGGGCCCCCCTC
CTTGCTCTGCAGGCACCTTAGTGGCTTTTTTCCTCCTGTGTACAGGGAAG
AGAGGGGTACATTTCCCTGTGCTGACGGAAGCCAACTTGGCTTTCCCGGA
CTGCAAGCAGGGCTCTGCCCCAGAGGCCTCTCTCTCCGTCGTGGGAGAGA
```
-continued
```
GACGTGTACATAGTGTAGGTCAGCGTGCTTAGCCTCCTGACCTGAGGCTC
CTGTGCTACTTTGCCTTTTGCAAACTTTATTTTCATAGATTGAGAAGTTT
TGTACAGAGAATTAAAAATGAAATTATTTATAATCTGGGTTTTGTGTCTT
CAGCTGATGGATGTGCTGACTAGTGAGAGTGCTTGGGCCCTCCCCCAGCA
CCTAGGGAAAGGCTTCCCCTCCCCCTCCGGCCACAAGGTACACAACTTTT
AACTTAGCTCTTCCCGATGTTTGTTTGTTAGTGGGAGGAGTGGGGAGGGC
TGGCTGTATGGCCTCCAGCCTACCTGTTCCCCCTGCTCCCAGGGCACATG
GTTGGGCTGTGTCAACCCTTAGGGCCTCCATGGGGTCAGTTGTCCCTTCT
CACCTCCCAGCTCTGTCCCCATCAGGTCCCTGGGTGGCACGGGAGGATGG
ACTGACTTCCAGGACCTGTTGTGTGACAGGAGCTACAGCTTGGGTCTCCC
TGCAAGAAGTCTGGCACGTCTCACCTCCCCCATCCCGGCCCCTGGTCATC
TCACAGCAAAGAAGCCTCCTCCCTCCCGACCTGCCGCCACACTGGAGAGG
GGGCACAGGGGCGGGGAGGTTTCCTGTTCTGTGAAAGGCCGACTCCCTG
ACTCCATTCATGCCCCCCCCCCAGCCCCTCCCTTCATTCCCATTCCCCA
ACCTAAAGCCTGGCCCGGCTCCCAGCTGAATCTGGTCGGAATCCACGGGC
TGCAGATTTTCCAAAACAATCGTTGTATCTTTATTGACTTTTTTTTTTT
TTTTTTCTGAATGCAATGACTGTTTTTTACTCTTAAGGAAAATAAACATC
TTTTAGAAACAAAAAAAAAAAA
```

The nucleic acid sequence, or CDS, for SREBF1 isoform c (GenBank Accession No. NM_001244003) is provided below.

(SEQ ID NO: 32)
```
ATGGACGAGCTGCCTTTCGGTGAGGCGGCTGTGGAACAGGCGCTGGACGA
GCTGGGCGAACTGGACGCCGCACTGCTGACCGACATCCAAGACATGCTTC
AGCTCATCAACAACCAAGACAGTGACTTCCCTGGCCTGTTTGATTCCCCC
TATGCAGGGGGCGGGGCAGGAGACACAGAGCCCACCAGCCCTGGTGCCAA
CTCTCCTGAGAGCTTGTCTTCTCCTGCTTCCCTGGGTTCCTCTCTGGAAG
CCTTCCTGGGGGAACCCAAGGCAACACCTGCATCCTTGTCCCCTGTGCCG
TCTGCATCCACTGCTTTAAAGATGTACCCGTCTGTGCCCCCCTTCTCCCC
TGGGCCTGGAATCAAAGAAGAGCCAGTGCCACTCACCATCCTGCAGCCCC
CAGCAGCAGACCATCACCAGGGACCCTCCTGCCTCCGAGTTTCCCTCCA
CCACCCCTGCAGCTCAGCCCGGCTCCTGTGCTGGGGTATTCTAGCCTTCC
TTCAGGCTTCTCAGGGACCCTTCCTGGAAATACCCAACAGCCACCATCTA
GCCTGTCACTGGCCTCTGCACCAGGAGTCTCGCCCATCTCTTTACACACC
CAGGTCCAGAGCTCAGCCTCCCAGCAGCCACTGCCAGCCTCAACAGCCCC
TAGAACAACCACTGTGACCTCACAGATCCAGCGGGTCCCAGTCGTACTGC
AGCCACATTTCATCAAGGCAGATTCACTGCTACTGACAACTGTAAAAACA
GATACAGGAGCCACGATGAAGACGGCTGGCATCAGTACCTTAGCCCCTGG
CACAGCCGTGCAGGCAGGCCCCTTGCAGACCCTGGTGAGTGGTGGGACCA
TCCTGGCCACAGTACCATTGGTTGTGGATACAGACAAACTGCCCATCCAT
CGACTGGCAGCTGGCAGCAAGGCCCTGGGCTCAGCTCAGAGCCGTGGTGA
```

GAAGCGCACAGCCCACAATGCCATTGAGAAGCGCTACCGTTCCTCTATCA

ATGACAAGATTGTGGAGCTCAAAGACCTGGTGGTGGGCACTGAGGCAAAG

CTGAATAAATCTGCCGTCTTGCGCAAGGCCATCGACTATATCCGCTTCTT

ACAGCACAGCAACCAGAAGCTCAAGCAGGAGAACCTGGCCCTGCGAAATG

CCGCTCACAAAAGCAAATCCCTGAAGGACCTGGTGTCGGCCTGTGGCAGT

GCAGGAGGCACAGATGTGGCTATGGAGGGTGTGAAGCCTGAGGTGGTGGA

TACGCTGACCCCTCCACCCTCAGACGCTGGCTCGCCCTCCCAGAGTAGCC

CCTTGTCCCTCGGCAGCAGAGGTAGCAGCAGTGGTGGCAGTGACTCGGAG

CCTGACAGCCCAGTCTTTGAGGATAGCCAGGTGAAAGCCCAACGGCTGCA

CAGTCATGGCATGCTGGACCGCTCCCGCCTAGCCCTGTGTGCGCTGGTCT

TCCTGTGTCTGACCTGCAACCCCTTGGCATCACTGTTTGGCTGGGGCATC

CCCGGTCCCTCCAGTGCCTCTGGTGCACACCACAGCTCTGGGCGTAGCAT

GCTGGAGGCCGAGAGCAGAGATGGCTCTAATTGGACCCAGTGGTTGCTGC

CACCCCTAGTCTGGCTGGCCAATGGACTACTAGTGTTGGCCTGCCTGGCT

CTTCTCTTTGTCTATGGGGAACCTGTGACCCGGCCACACACTAGCCCAGC

TGTACACTTCTGGAGACATCGCAAACAGGCTGACCTGGACTTGGCTCGGG

GAGATTTTGCCCAGGCTGCTCAGCAGCTGTGGCTGGCCCTGCAGGCATTG

GGACGGCCCCTGCCCACCTCGAACCTAGACTTGGCCTGCAGCCTGCTTTG

GAACCTCATCCGCCACCTGCTGCAGCGTCTCTGGGTTGGCCGCTGGCTGG

CAGGCCGGGCTGGGGGCTTGCGGAGAGACTGTGGACTGAGAATGGATGCA

CGTGCCAGTGCTCGAGATGCGGCTCTCGTCTACCATAAGCTGCACCAGCT

GCATGCCATGGGCAAATACACAGGAGGGCACCTCATTGCTTCTAACCTGG

CACTGAGTGCCCTGAACCTGGCCGAGTGCGCAGGAGATGCTGTATCCATG

GCAACGCTGGCAGAGATCTATGTGGCTGCTGCCCTGAGGGTCAAGACCAG

TCTCCCAAGAGCCTTGCACTTTTTGACACGTTTCTTCCTGAGTAGTGCCC

GCCAGGCCTGCCTGGCACAGAGTGGCTCAGTGCCTCTTGCCATGCAGTGG

CTCTGCCACCCTGTAGGCCACCGTTTCTTCGTGGATGGGGACTGGGCTGT

GCATGGTGCCCCACAGGAGAGCCTGTACAGCGTGGCTGGGAACCCAGTGG

ATCCCCTCGCCCAGGTGACTCGACTATTCTGCGAACATCTCTTGGAGAGA

GCACTGAACTGTATTGCTCAACCCAGCCCGGGACAGCTGATGGAGACAG

GGAGTTCTCTGACGCACTTGGATACCTGCAGTTGCTAAATCGCTGCTCTG

ATGCTGTCGGGACTCCTGCCTGCAGCTTCTCTGTCAGCTCCAGCATGGCT

TCCACCACCGGCACAGACCCAGTGGCCAAGTGGTGGGCCTCACTGACGGC

TGTGGTGATCCACTGGCTGCGGCGGGATGAAGAGGCAGCTGAGCGCCTAT

ACCCGCTGGTAGAGCGTATGCCCCACGTGCTGCAGGAGACTGAGAGACCC

CTGCCCAAGGCAGCTCTGTACTCCTTCAAGGCTGCCCGGGCTCTGCTGGA

CCACAGAAAAGTGGAGTCTGGCCCAGCCAGCCTGGCCATCTGTGAGAAGG

CCAGCGGGTACTTGCGGGACAGCTTAGCCGCTCCACCAACTGGCAGCTCC

ATTGACAAGGCCATGCAGCTGCTCCTGTGTGATCTACTTCTTGTGGCCCG

CACTAGTATGTGGCAGCGCCAGCAGTCACCAGCCTCAGCCCAGGTAGCTC

ACAGTGCCAGCAATGGATCTCAGGCCTCCGCTTTGGAGCTTCGAGGTTTC

CAACAGGACCTGAGCAGCCTGAGGCGCTTGGCACAGAACTTCCGGCCTGC

TATGAGGAGAGTGTTCCTACACGAGGCCACAGCTCGGCTGATGGCAGGGG

CAAGTCCTGCCCGGACACACCAGCTCCTGGACCGAAGTCTGCGGAGGCGG

GCCGGCTCCAGTGGCAAAGGAGGCACTGTAGCTGAGCTGGAGCCTCGACC

CACATGGCGGGAGCACACAGAGGCCTTGCTGCTGGCCTCCTGCTATCTGC

CACCTGCCTTCCTGTCGGCCCCTGGACAGCAAATGAGCATGTTGGCTGAG

GCAGCACGCACTGTAGAGAAGCTTGGTGATCATCGGCTACTGCTTGACTG

CCAGCAGATGCTTCTGCGCCTGGGCGGTGGGACCACTGTCACTTCCAGCT

AA

The nucleic acid sequence, or mRNA sequence, for SREBF1 isoform c (GenBank Accession No. NM_001244003) is provided below.

(SEQ ID NO: 33)
CTCCTGCGAAGCCTGGCGGGCGCCGCCGCCATGGACGAGCTGCCTTTCGG

TGAGGCGGCTGTGGAACAGGCGCTGGACGAGCTGGGCGAACTGGACGCCG

CACTGCTGACCGACATCCAAGACATGCTTCAGCTCATCAACAACCAAGAC

AGTGACTTCCCTGGCCTGTTTGATTCCCCCTATGCAGGGGGCGGGGCAGG

AGACACAGAGCCCACCAGCCCTGGTGCCAACTCTCCTGAGAGCTTGTCTT

CTCCTGCTTCCCTGGGTTCCTCTCTGGAAGCCTTCCTGGGGGAACCCAAG

GCAACACCTGCATCCTTGTCCCCTGTGCCGTCTGCATCCACTGCTTTAAA

GATGTACCCGTCTGTGCCCCCTTCTCCCCTGGGCCTGGAATCAAAGAAG

AGCCAGTGCCACTCACCATCCTGCAGCCCCCAGCAGCACAGCCATCACCA

GGGACCCTCCTGCCTCCGAGTTTCCCTCCACCACCCCTGCAGCTCAGCCC

GGCTCCTGTGCTGGGGTATTCTAGCCTTCCTTCAGGCTTCTCAGGGACCC

TTCCTGGAAATACCCAACAGCCACCATCTAGCCTGTCACTGGCCTCTGCA

CCAGGAGTCTCGCCCATCTCTTTACACACCCAGGTCCAGAGCTCAGCCTC

CCAGCAGCCACTGCCAGCCTCAACAGCCCCTAGAACAACCACTGTGACCT

CACAGATCCAGCGGGTCCCAGTCGTACTGCAGCCACATTTCATCAAGGCA

GATTCACTGCTACTGACAACTGTAAAAACAGATACAGGAGCCACGATGAA

GACGGCTGGCATCAGTACCTTAGCCCCTGGCACAGCCGTGCAGGCAGGCC

CCTTGCAGACCCTGGTGAGTGGTGGGACCATCCTGGCCACAGTACCATTG

GTTGTGGATACAGACAAACTGCCCATCCATCGACTGGCAGCTGGCAGCAA

GGCCCTGGGCTCAGCTCAGAGCCGTGGTGAGAAGCGCACAGCCCACAATG

CCATTGAGAAGCGCTACCGTTCCTCTATCAATGACAAGATTGTGGAGCTC

AAAGACCTGGTGGTGGGCACTGAGGCAAAGCTGAATAAATCTGCCGTCTT

GCGCAAGGCCATCGACTATATCCGCTTCTTACAGCACAGCAACCAGAAGC

TCAAGCAGGAGAACCTGGCCCTGCGAAATGCCGCTCACAAAAGCAAATCC

CTGAAGGACCTGGTGTCGGCCTGTGGCAGTGCAGGAGGCACAGATGTGGC

TATGGAGGGTGTGAAGCCTGAGGTGGTGGATACGCTGACCCCTCCACCCT

CAGACGCTGGCTCGCCCTCCCAGAGTAGCCCCTTGTCCCTCGGCAGCAGA

-continued
```
GGTAGCAGCAGTGGTGGCAGTGACTCGGAGCCTGACAGCCCAGTCTTTGA
GGATAGCCAGGTGAAAGCCCAACGGCTGCACAGTCATGGCATGCTGGACC
GCTCCCGCCTAGCCCTGTGTGCGCTGGTCTTCCTGTGTCTGACCTGCAAC
CCCTTGGCATCACTGTTTGGCTGGGGCATCCCCGGTCCCTCCAGTGCCTC
TGGTGCACACCACAGCTCTGGGCGTAGCATGCTGGAGGCCGAGAGCAGAG
ATGGCTCTAATTGGACCCAGTGGTTGCTGCCACCCCTAGTCTGGCTGGCC
AATGGACTACTAGTGTTGGCCTGCCTGGCTCTTCTCTTTGTCTATGGGGA
ACCTGTGACCCGGCCACACACTAGCCCAGCTGTACACTTCTGGAGACATC
GCAAACAGGCTGACCTGGACTTGGCTCGGGAGATTTTGCCCAGGCTGCT
CAGCAGCTGTGGCTGGCCCTGCAGGCATTGGGACGGCCCCTGCCCACCTC
GAACCTAGACTTGGCCTGCAGCCTGCTTTGGAACCTCATCCGCCACCTGC
TGCAGCGTCTCTGGGTTGGCCGCTGGCTGGCAGGCCGGGCTGGGGGCTTG
CGGAGAGACTGTGGACTGAGAATGGATGCACGTGCCAGTGCTCGAGATGC
GGCTCTCGTCTACCATAAGCTGCACCAGCTGCATGCCATGGGCAAATACA
CAGGAGGGCACCTCATTGCTTCTAACCTGGCACTGAGTGCCCTGAACCTG
GCCGAGTGCGCAGGAGATGCTGTATCCATGGCAACGCTGGCAGAGATCTA
TGTGGCTGCTGCCCTGAGGGTCAAGACCAGTCTCCCAAGAGCCTTGCACT
TTTTGACACGTTTCTTCCTGAGTAGTGCCCGCCAGGCCTGCCTGGCACAG
AGTGGCTCAGTGCCTCTTGCCATGCAGTGGCTCTGCCACCCTGTAGGCCA
CCGTTTCTTCGTGGATGGGGACTGGGCTGTGCATGGTGCCCCACAGGAGA
GCCTGTACAGCGTGGCTGGGAACCCAGTGGATCCCCTCGCCCAGGTGACT
CGACTATTCTGCGAACATCTCTTGGAGAGAGCACTGAACTGTATTGCTCA
ACCCAGCCCGGGACAGCTGATGGAGACAGGGAGTTCTCTGACGCACTTG
GATACCTGCAGTTGCTAAATCGCTGCTCTGATGCTGTCGGGACTCCTGCC
TGCAGCTTCTCTGTCAGCTCCAGCATGGCTTCCACCACCGGCACAGACCC
AGTGGCCAAGTGGTGGGCCTCACTGACGGCGTGGTGATCCACTGGCTGC
GGCGGGATGAAGAGGCAGCTGAGCGCCTATACCCGCTGGTAGAGCGTATG
CCCCACGTGCTGCAGGAGACTGAGAGACCCCTGCCCAAGGCAGCTCTGTA
CTCCTTCAAGGCTGCCCGGGCTCTGCTGGACCACAGAAAAGTGGAGTCTG
GCCCAGCCAGCCTGGCCATCTGTGAGAAGGCCAGCGGGTACTTGCGGGAC
AGCTTAGCCGCTCCACCAACTGGCAGCTCCATTGACAAGGCCATGCAGCT
GCTCCTGTGTGATCTACTTCTTGTGGCCCGCACTAGTATGTGGCAGCGCC
AGCAGTCACCAGCCTCAGCCCAGGTAGCTCACAGTGCCAGCAATGGATCT
CAGGCCTCCGCTTTGGAGCTTCGAGGTTTCCAACAGGACCTGAGCAGCCT
GAGGCGCTTGGCACAGAACTTCCGGCCTGCTATGAGGAGAGTGTTCCTAC
ACGAGGCCACAGCTCGGCTGATGGCAGGGGCAAGTCCTGCCCGGACACAC
CAGCTCCTGGACCGAAGTCTGCGGAGGCGGGCCGGCTCCAGTGGCAAAGG
AGGCACTGTAGCTGAGCTGGAGCCTCGACCCACATGCGGGAGCACACAG
AGGCCTTGCTGCTGGCCTCCTGCTATCTGCCACCTGCCTTCCTGTCGGCC
CCTGGACAGCAAATGAGCATGTTGGCTGAGGCAGCACGCACTGTAGAGAA
GCTTGGTGATCATCGGCTACTGCTTGACTGCCAGCAGATGCTTCTGCGCC
TGGGCGGTGGGACCACTGTCACTTCCAGCTAAACCTTGGATGGTCTCCCC
AGTATTAGAGGCCCTTAAGGACCTTTGTCACTGGCTGTGGTCGTCCAGAG
AGGGTGAGCCTGACAAGCAATCAGGATCATGCCGACCTCTAGTGACAAAT
CTAGAAATTGCAGAGGCTGCACTGGCCCAATGCCACCCTCTTGCTCTGTA
GGCACCTTTTTCCTGTCCTATGGAAAGGAACCTTTCCCCTAGCTGAGGGC
CACCCTGTCCTGAGGCTCTCACCCACTCCTGGAAGACTTGTATATAGTGT
AGATCCAGCTGAGCCAGTTTCCTGTGCAGGCTCATGTACTACTTTAACTT
TTGCAAACTTTATTTTCATAGGTTGAGAAATTTTGTACAGAAAATTAAAA
AGTGAAATTATTTATA
```

The amino acid sequence for SREBF1 isoform c (GenBank Accession No. NM_001244003) is provided below.

(SEQ ID NO: 34)
```
MDELPFGEAAVEQALDELGELDAALLTDIQDMLQLINNQDSDFPGLFDSP
YAGGGAGDTEPTSPGANSPESLSSPASLGSSLEAFLGEPKATPASLSPVP
SASTALKMYPSVPPFSPGPGIKEEPVPLTILQPPAAQPSPGTLLPPSFPP
PPLQLSPAPVLGYSSLPSGFSGTLPGNTQQPPSSLSLASAPGVSPISLHT
QVQSSASQQPLPASTAPRTTTVTSQIQRVPVVLQPHFIKADSLLLTTVKT
DTGATMKTAGISTLAPGTAVQAGPLQTLVSGGTILATVPLVVDTDKLPIH
RLAAGSKALGSAQSRGEKRTAHNAIEKRYRSSINDKIVELKDLVVGTEAK
LNKSAVLRKAIDYIRFLQHSNQKLKQENLALRNAAHKSKSLKDLVSACGS
AGGTDVAMEGVKPEVVDTLTPPPSDAGSPSQSSPLSLGSRGSSSGGSDSE
PDSPVFEDSQVKAQRLHSHGMLDRSRLALCALVFLCLTCNPLASLFGWGI
PGPSSASGAHHSSGRSMLEAESRDGSNWTQWLLPPLVWLANGLLVLACLA
LLFVYGEPVTRPHTSPAVHFWRHRKQADLDLARGDFAQAAQQLWLALQAL
GRPLPTSNLDLACSLLWNLIRHLLQRLWVGRWLAGRAGGLRRDCGLRMDA
RASARDAALVYHKLHQLHAMGKYTGGHLIASNLALSALNLAECAGDAVSM
ATLAEIYVAAALRVKTSLPRALHFLTRFFLSSARQACLAQSGSVPLAMQW
LCHPVGHRFFVDGDWAVHGAPQESLYSVAGNPVDPLAQVTRLFCEHLLER
ALNCIAQPSPGTADGDREFSDALGYLQLLNRCSDAVGTPACSFSVSSSMA
STTGTDPVAKWWASLTAVVIHWLRRDEEAAERLYPLVERMPHVLQETERP
LPKAALYSFKAARALLDHRKVESGPASLAICEKASGYLRDSLAAPPTGSS
IDKAMQLLLCDLLLVARTSMWQRQQSPASAQVAHSASNGSQASALELRGF
QQDLSSLRRLAQNFRPAMRRVFLHEATARLMAGASPARTHQLLDRSLRRR
AGSSGKGGTVAELEPRPTWREHTEALLLASCYLPPAFLSAPGQQMSMLAE
AARTVEKLGDHRLLLDCQQMLLRLGGGTTVTSS
```

The nucleic acid sequence, or mRNA sequence, for truncated SREBF1 isoform c (GenBank Accession No. NM_001244003), e.g., SREB411, is provided below.

(SEQ ID NO: 35)
```
atggacgagctgcctttcggtgaggcggctgtggaacaggcgctggacga
gctgggcgaactggacgccgcactgctgaccgacatccaagacatgcttc
```

-continued

```
agctcatcaacaaccaagacagtgacttccctggcctgtttgattccccc
tatgcaggggcggggcaggagacacagagcccaccagccctggtgccaa
ctctcctgagagcttgtcttctcctgcttccctgggttcctctctggaag
ccttcctgggggaacccaaggcaacacctgcatccttgtccctgtgccg
tctgcatccactgctttaaagatgtacccgtctgtgcccccttctcccc
tgggcctggaatcaaagaagagccagtgccactcaccatcctgcagccc
cagcagcacagccatcaccagggaccctcctgcctccgagtttccctcca
ccaccctgcagctcagcccggctcctgtgctggggtattctagccttcc
ttcaggcttctcagggacccttcctggaaatacccaacagccaccatcta
gcctgtcactggcctctgcaccaggagtctcgcccatctctttacacacc
caggtccagagctcagcctcccagcagccactgccagcctcaacagcccc
tagaacaaccactgtgacctcacagatccagcgggtcccagtcgtactgc
agccacatttcatcaaggcagattcactgctactgacaactgtaaaaaca
gatacaggagccacgatgaagacggctggcatcagtaccttagcccctgg
cacagccgtgcaggcaggcccttgcagaccctggtgagtggtgggacca
tcctggccacagtaccattggttgtggatacagacaaactgcccatccat
cgactggcagctggcagcaaggccctgggctcagctcagagccgtggtga
gaagcgcacagcccacaatgccattgagaagcgctaccgttcctctatca
atgacaagattgtggagctcaaagaccggtggtgggcactgaggcaaag
ctgaataaatctgccgtcttgcgcaaggccatcgactatatccgcttctt
acagcacagcaaccagaagctcaagcaggagaacctggccctgcgaaatg
ccgctcacaaaagcaaatccctgaaggacctggtgtcggcctgtggcagt
gcaggaggcacagatgtggctatggagggtgtg
```

The amino acid sequence for truncated SREBF1 isoform c (GenBank Accession No. NM_001244003), e.g., SREB411, is provided below.

```
                                                (SEQ ID NO: 36)
MDELPFGEAAVEQALDELGELDAALLTDIQDMLQLINNQDSDFPGLFDSP

YAGGGAGDTEPTSPGANSPESLSSPASLGSSLEAFLGEPKATPASLSPVP

SASTALKMYPSVPPFSPGPGIKEEPVPLTILQPPAAQPSPGTLLPPSFPP

PPLQLSPAPVLGYSSLPSGFSGTLPGNTQQPPSSLSLASAPGVSPISLHT

QVQSSASQQPLPASTAPRTTTVTSQIQRVPVVLQPHFIKADSLLLTTVKT

DTGATMKTAGISTLAPGTAVQAGPLQTLVSGGTILATVPLVVDTDKLPIH

RLAAGSKALGSAQSRGEKRTAHNAIEKRYRSSINDKIVELKDLVVGTEAK

LNKSAVLRKAIDYIRFLQHSNQKLKQENLALRNAAHKSKSLKDLVSACGS

AGGTDVAMEGV
```

In one embodiment, the LMM comprises at least 50%, 55%, 60%, 65%, 70%, 75%, 80%, 85%, 90%, 95%, 96%, 97%, 98%, 99%, or 100% identity with the amino acid sequence of an isoform of SREBF1; e.g., SEQ ID NOs: 28, 30, 34, or 36; or differs by 1, 2, or 3 or more amino acid residues but no more than 50, 40, 30, 20, 15, or 10 amino acid residues from the amino acid sequence of an isoform of SREBF1; e.g., SEQ ID NOs: 28, 30, 34, or 36.

In one embodiment, the LMM comprises at least 50%, 55%, 60%, 65%, 70%, 75%, 80%, 85%, 90%, 95%, 96%, 97%, 98%, 99%, or 100% identity with the amino acid sequence of SREBF1; e.g., SEQ ID NO: 34; or differs by 1, 2, or 3 or more amino acid residues but no more than 50, 40, 30, 20, 15, or 10 amino acid residues from the amino acid sequence of SREBF1, e.g., SEQ ID NO: 34.

In another embodiment, the LMM comprises a functional fragment of SREBF1 or an isoform thereof, e.g., a truncated SREBF1. In one embodiment, the LMM comprises a functional fragment of SREBF1, e.g., a functional fragment of SEQ ID NOs: 1 or 34, or a functional fragment of an SREBF1 isoform, e.g., SEQ ID NOs: 28, 30, or 36. In one embodiment, the LMM comprises a functional domain of SREBF1, e.g., the transactivation domain of SREBF1. In one embodiment, the LMM comprises the helix-loop-helix (HLH) domain of SREBF1. In one embodiment, the LMM comprises a functional fragment of SREBF1 that is capable of translocating into the nucleus and/or capable of initiating transcription of SREBF1 target genes.

In one embodiment, the LMM comprises the N-terminal 410 amino acids of SREBF1 (also referred to herein as SREBF410), e.g., amino acids 1-410 of SEQ ID NO: 1. The amino acid sequence of the N-terminal 410 amino acids of SREBF1 is provided below:

```
                                                (SEQ ID NO: 26)
MDELAFGEAALEQTLAEMCELDTAVLNDIEDMLQLINNQDSDFPGLFDAP

YAGGETGDTGPSSPGANSPESFSSASLASSLEAFLGGPKVTPAPLSPPPS

APAALKMYPSVSPFSPGPGIKEEPVPLTILQPAAPQPSPGTLLPPSFPAP

PVQLSPAPVLGYSSLPSGFSGTLPGNTQQPPSSLPLAPAPGVLPTPALHT

QVQSLASQQPLPASAAPRTNTVTSQVQQVPVVLQPHFIKADSLLLTAVKT

DAGATVKTAGISTLAPGTAVQAGPLQTLVSGGTILATVPLVVDTDKLPIH

RLAAGSKALGSAQSRGEKRTAHNAIEKRYRSSINDKIVELKDLVVGTEAK

LNKSAVLRKAIDYIRFLQHSNQKLKQENLTLRSAHKSKSLKDLVSACGSG

GGTDVSMEGM
```

In one embodiment, the LMM comprises at least 50%, 55%, 60%, 65%, 70%, 75%, 80%, 85%, 90%, 95%, 96%, 97%, 98%, 99%, or 100% identity with the amino acid sequence of the N-terminal 410 amino acids of SREBF1; e.g., SEQ ID NO: 26; or differs by 1, 2, or 3 or more amino acid residues but no more than 50, 40, 30, 20, 15, or 10 amino acid residues from the amino acid sequence of the N-terminal 410 amino acids of SREBF1; e.g., SEQ ID NO: 26.

In another embodiment, the LMM comprises amino acids 91-410 of SREBF1, e.g., amino acids 91-410 of SEQ ID NO: 1. The amino acid sequence of the amino acids at positions 91-410 of SREBF1 is provided below:

```
                                                (SEQ ID NO: 27)
MPAPLSPPPSAPAALKMYPSVSPFSPGPGIKEEPVPLTILQPAAPQPSPG

TLLPPSFPAPPVQLSPAPVLGYSSLPSGFSGTLPGNTQQPPSSLPLAPAP

GVLPTPALHTQVQSLASQQPLPASAAPRTNTVTSQVQQVPVVLQPHFIKA

DSLLLTAVKTDAGATVKTAGISTLAPGTAVQAGPLQTLVSGGTILATVPL

VVDTDKLPIHRLAAGSKALGSAQSRGEKRTAHNAIEKRYRSSINDKIVEL
```

-continued
KDLVVGTEAKLNKSAVLRKAIDYIRFLQHSNQKLKQENLTLRSAHKSKSL

KDLVSACGSGGGTDVSMEGM

In one embodiment, the LMM comprises at least 50%, 55%, 60%, 65%, 70%, 75%, 80%, 85%, 90%, 95%, 96%, 97%, 98%, 99%, or 100% identity with the amino acid sequence at positions 91-410 of SREBF1; e.g., SEQ ID NO: 27; or differs by 1, 2, or 3 or more amino acid residues but no more than 50, 40, 30, 20, 15, or 10 amino acid residues from the amino acid sequence at positions 91-410 of SREBF1; e.g., SEQ ID NO: 27. In one embodiment, the LMM comprises at least 50%, 55%, 60%, 65%, 70%, 75%, 80%, 85%, 90%, 95%, 96%, 97%, 98%, 99%, or 100% identity with the nucleic acid sequence encoding SREBF1 or a functional fragment thereof; e.g., encoding the amino acid sequence SEQ ID NO: 1 or a functional fragment thereof. In one embodiment, the LMM comprises at least 50%, 55%, 60%, 65%, 70%, 75%, 80%, 85%, 90%, 95%, 96%, 97%, 98%, 99%, or 100% identity with the nucleic acid of SEQ ID NO: 2.

In another embodiment, the LMM comprises at least 50%, 55%, 60%, 65%, 70%, 75%, 80%, 85%, 90%, 95%, 96%, 97%, 98%, 99%, or 100% identity with SREBF2 or a functional fragment thereof; or differs by 1, 2, or 3 or more amino acid residues but no more than 50, 40, 30, 20, 15, or 10 amino acid residues from SREBF2 or a functional fragment thereof.

In one embodiment, the LMM comprises an enzyme. In one embodiment, the LMM comprises an enzyme that converts saturated fatty acids to unsaturated fatty acids. In one embodiment, the LMM comprises an enzyme that converts saturated fatty acids to monounsaturated fatty acids, e.g., fatty acids with one double bond. In one embodiment, the LMM comprises an enzyme that converts saturated fatty acids to polyunsaturated fatty acids, e.g., fatty acids with more than one, e.g., 2, 3, 4, 5, or more, double bonds. In one embodiment, the LMM comprises stearoyl CoA desaturase 1 (SCD1), stearoyl CoA desaturase 2 (SCD2), stearoyl CoA desaturase 3 (SCD3), stearoyl CoA desaturase 4 (SCD4), stearoyl CoA desaturase 5 (SCD5), an isoform thereof, or a functional fragment thereof.

SCD1 is the rate limiting enzyme responsible for the conversion of saturated fatty acids (SFA) to monounsaturated fatty acids (MUFA). Increased focus has been placed upon SCD1 in recent years due to studies linking expression of this gene to increased cell survival, proliferation and tumorigenesis properties (Angelucci, Maulucci et al. 2015) (Igal 2011). SCD1 has also been shown to play key roles in both cellular metabolic rate control and overall lipogenesis. The latter is controlled through direct interactions with a major biosynthetic pathway regulator acetyl-CoA carboxylase (ACC) as well as conversion of SFA to MUFA which, since SFA is known to inhibit ACC, facilitates enzyme functionality to increase lipid biosynthesis (Igal 2010). The main regulation of SCD1 is through transcriptional activation whereby transcription factors, such as SREBF1, bind to the SRE sequence in the promoter region of the gene. SCD1 is endogenously located in the ER as a membrane integral protein, where SCD1 carries out its enzymatic function of catalyzing the conversion of SFA to MUFA. Its role in conversion of SFA to MUFA (e.g., upregulation of the ratio of MUFA to SFA) can regulate a decrease in lipid raft domains, which can in turn result in increased membrane fluidity. This change in membrane fluidity and membrane lipid composition may also have implications in vesicle formation and thus cellular communication and ER size or morphology (e.g., ER expansion). Knockdown of the SCD1 gene has also been shown to upregulate the unfolded protein response (Ariyama, Kono et al. 2010). Furthermore, SCD1 negatively regulates cellular palmitic acid which, in turn, is a strong negative regulator of ACC. SCD1 also controls the phosphorylation status of AMP activated protein kinase (AMPK), consequentially reducing its ability to phosphorylate and therefore inhibit ACC; a rate-limiting enzyme in the lipid synthesizing process. Lastly, desaturation of SFA prevents its accumulation which can cause cell death. As such, modulation of SCD1 results in increased lipid biosynthesis, cell survival and proliferation rates. (Hagen, Rodriguez-Cuenca et al.), (Scaglia, Chisholm et al. 2009).

In one embodiment, the LMM comprises SCD1. The amino acid sequence of SCD1 is provided below:

(SEQ ID NO: 3)
MPAHMLQEISSSYTTTTTITAPPSGNEREKVKTVPLHLEEDIRPEMKEDI

HDPTYQDEEGPPPKLEYVWRNIILMVLLHLGGLYGIILVPSCKLYTCLFG

IFYYMTSALGITAGAHRLWSHRTYKARLPLRIFLIIANTMAFQNDVYEWA

RDHRAHHKFSETHADPHNSRRGFFFSHVGWLLVRKHPAVKEKGGKLDMSD

LKAEKLVMFQRRYYKPGLLLMCFILPTLVPWYCWGETFVNSLFVSTFLRY

TLVLNATWLVNSAAHLYGYRPYDKNIQSRENILVSLGAVGEGFHNYHHTF

PFDYSASEYRWHINFTTFFIDCMAALGLAYDRKKVSKATVLARIKRTGDG

SHKSS

The nucleotide sequence of SCD1 is provided below:

(SEQ ID NO: 4)
atgccggcccacatgctccaagagatctccagttcttacacgaccaccac caccatcactgcacctccctccggaaatgaacgagagaaggtgaagacgg tgccctccacctggaagaagacatccgtcctgaaatgaaagaagatatt cacgacccacctatcaggatgaggagggacccccgcccaagctggagta cgtctggaggaacatcattctcatggtcctgctgcacttgggaggcctgt acgggatcatactggttccctcctgcaagctctacacctgcctcttcggg attttctactacatgaccagcgctctgggcatcacagccggggctcatcg cctctggagccacagaacttacaaggcacggctgcccctgcggatcttcc ttatcattgccaacaccatggcgttccagaatgacgtgtacgaatgggcc cgagatcaccgcgccaccacaagttctcagaaacacacgccgaccctca caattcccgccgtggcttcttcttctctcacgtgggttggctgcttgtgc gcaaacacccggctgtcaaagagaagggcggaaaactggacatgtctgac ctgaaagccgagaagctggtgatgttccagaggaggtactacaagcccgg cctcctgctgatgtgcttcatcctgcccacgctggtgccctggtactgct ggggcgagacttttgtaaacagcctgttcgttagcaccttcttgcgatac actctggtgctcaacgccacctggctggtgaacagtgccgcgcatctcta tggatatcgcccctacgacaagaacattcaatcccgggagaatatcctgg tttccctgggtgccgtgggcgagggcttccacaactaccaccacaccttc ccccttcgactactctgccagtgagtaccgctggcacatcaacttcaccac

```
-continued
gttcttcatcgactgcatggctgccctgggcctggcttacgaccggaaga aagtttctaaggctactgtcttagccaggattaagagaactggagacggg agtcacaagagtagctga
```

In one embodiment, the LMM comprises at least 50%, 55%, 60%, 65%, 70%, 75%, 80%, 85%, 90%, 95%, 96%, 97%, 98%, 99%, or 100% identity with the amino acid sequence of SCD1; e.g., SEQ ID NO: 3; or differs by 1, 2, or 3 or more amino acid residues but no more than 50, 40, 30, 20, 15, or 10 amino acid residues from the amino acid sequence of SCD1, e.g., SEQ ID NO: 3. In one embodiment, the LMM comprises a functional fragment of SCD1, e.g., a functional fragment of SEQ ID NO: 3.

In one embodiment, the LMM comprises at least 50%, 55%, 60%, 65%, 70%, 75%, 80%, 85%, 90%, 95%, 96%, 97%, 98%, 99%, or 100% identity with the nucleic acid sequence encoding SCD1 or a functional fragment thereof; e.g., encoding the amino acid sequence SEQ ID NO: 3 or a functional fragment thereof. In one embodiment, the LMM comprises at least 50%, 55%, 60%, 65%, 70%, 75%, 80%, 85%, 90%, 95%, 96%, 97%, 98%, 99%, or 100% identity with the nucleic acid of SEQ ID NO: 4.

In another embodiment, the LMM comprises at least 50%, 55%, 60%, 65%, 70%, 75%, 80%, 85%, 90%, 95%, 96%, 97%, 98%, 99%, or 100% identity with the amino acid sequence of SCD2, SCD3, SCD4, SCD5, or a functional fragment thereof; or differs by 1, 2, or 3 or more amino acid residues but no more than 50, 40, 30, 20, 15, or 10 amino acid residues from the amino acid sequence of SCD2, SCD3, SCD4, SCD5, or a functional fragment thereof. In another embodiment, the LMM comprises at least In another embodiment, the LMM comprises a functional fragment of SCD1, SCD2, SCD3, SCD4, or SCD5, e.g., a truncated SCD1, SCD2, SCD3, SCD4, or SCD5. In one embodiment, the LMM comprises a functional fragment of SCD1, SCD2, SCD3, SCD4, or SCD5, e.g., a functional fragment of SEQ ID NO: 3. In one embodiment, the LMM comprises a functional domain of SCD1, SCD2, SCD3, SCD4, or SCD5, e.g., a domain having enzymatic activity for converting saturated fatty acids to monounsaturated fatty acids.

Percent identity in the context of two or more amino acid or nucleic acid sequences, refers to two or more sequences that are the same. Two sequences are "substantially identical" if two sequences have a specified percentage of amino acid residues or nucleotides that are the same (e.g., 60% identity, optionally 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity over a specified region, or, when not specified, over the entire sequence, when compared and aligned for maximum correspondence over a comparison window, or designated region as measured using one of the following sequence comparison algorithms or by manual alignment and visual inspection. In some embodiments, alignment may result in gaps or inserted sequences, in which sequence similarity can be determined for specified regions flanking the gaps or inserted sequences, or sequence similarity can be determined across a region that includes the gaps or inserted sequences. Optionally, the identity exists over a region that is at least about 50 amino acids or nucleotides, 100 amino acids or nucleotides, 150 amino acids or nucleotides, in length. More preferably, the identity exists over a region that is about 200 or more amino acids or nucleotides, or about 500 or 1000 or more amino acids or nucleotides, in length.

For sequence comparison, one sequence typically acts as a reference sequence, to which one or more test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology). Multiple sequence alignments can be performed by algorithms such as ClustalW, Clustal Omega, and MAFFT. Other algorithms for comparing relationships between two or more sequences include the Hidden Markov models. A hidden Markov Model is a model that describes the probability of a having a particular nucleotide (or amino acid) type following another (the probability path being hidden).

It is really a probabilistic model not an algorithm. Example of an algorithm (or program implementing the algorithm) might be HMMER (http://hmmer.org/).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information (NCBI).

Products

Provided herein are methods and compositions for engineering or making a cell or a cell-free expression system capable of producing high yields of a product and/or improved product quality. Products described herein include polypeptides, e.g., recombinant proteins; nucleic acid molecules, e.g., DNA or RNA molecules; multimeric proteins or complexes; lipid-encapsulated particles, e.g., virus-like particles, vesicles, or exosomes; or other molecules, e.g., lipids. In an embodiment, the product is a polypeptide, e.g., a recombinant polypeptide. In an embodiment, the product is an exosome. For example, the recombinant polypeptide can be a difficult to express protein or a protein having complex and/or non-natural structures, such as a next generation biologic, e.g., a bispecific antibody molecule, a fusion protein, or a glycosylated protein.

In embodiments, the cell or cell line generated by the methods or compositions described herein produces a product, e.g., a recombinant polypeptide, useful in the treatment of a medical condition, disorder or disease. Examples of medical conditions, disorders or diseases include, but are not limited to, metabolic disease or disorders (e.g., metabolic enzyme deficiencies), endocrine disorders (e.g., hormone deficiencies), dysregulation of hemostasis, thrombosis, hematopoietic disorders, pulmonary disorders, gastro-intestinal disorders, autoimmune diseases, immuno-dysregulation (e.g., immunodeficiency), infertility, transplantation, cancer, and infectious diseases.

In embodiments, the product is an exogenous protein, e.g., a protein that is not naturally expressed by the cell. In one embodiment, the protein is from one species while the cell is from a different species. In another embodiment, the protein is a non-naturally occurring protein.

In other embodiments, the product is a protein that is endogenously expressed by the cell. In one embodiment, the product is a protein that is endogenously expressed by the cell at endogenous or natural levels. The present methods and compositions described herein are used to increase the production and quality of the endogenous product, e.g., a naturally occurring product that is naturally produced by the cell. In another embodiment, an exogenous nucleic acid encoding the product, e.g., protein, is introduced to and expressed by the cell. In another embodiment, an exogenous nucleic acid that increases the expression of a product that is endogenously expressed by the cell is introduced into the cell. By way of example, the exogenous nucleic acid comprises a sequence that activates the promoter (e.g., SRF promoter sequence, see e.g., The transcription factor Ap-1 regulates monkey 20α-hydroxysteroid dehydrogenase promoter activity in CHO cells. Nanjidsuren T, Min K S. BMC Biotechnol. 2014 Jul. 30; 14:71. doi: 10.1186/1472-6750-14-71.PMID: 25073972) that controls the expression of an endogenous product of the cell.

The recombinant product can be a therapeutic product or a diagnostic product, e.g., useful for drug screening. The therapeutic or diagnostic product can include, but is not limited to, an antibody molecule, e.g., an antibody or an antibody fragment, a fusion protein, a hormone, a cytokine, a growth factor, an enzyme, a glycoprotein, a lipoprotein, a reporter protein, a therapeutic peptide, or a structural and/or functional fragment or hybrid of any of these. In other embodiments, the therapeutic or diagnostic product is a synthetic polypeptide, e.g., wherein the entire polypeptide or portions thereof is not derived from or has any sequence or structural similarity to any naturally occurring polypeptide, e.g., a naturally occurring polypeptide described above.

In one embodiment, the recombinant product is an antibody molecule. In one embodiment, the recombinant product is a therapeutic antibody molecule. In another embodiment, the recombinant product is a diagnostic antibody molecule, e.g., a monoclonal antibody useful for imaging techniques or diagnostic tests.

An antibody molecule, as used herein, is a protein, or polypeptide sequence derived from an immunoglobulin molecule which specifically binds with an antigen. In an embodiment, the antibody molecule is a full-length antibody or an antibody fragment. Antibodies and multiformat proteins can be polyclonal or monoclonal, multiple or single chain, or intact immunoglobulins, and may be derived from natural sources or from recombinant sources. Antibodies can be tetramers of immunoglobulin molecules. In an embodiment, the antibody is a monoclonal antibody. The antibody may be a human or humanized antibody. In one embodiment, the antibody is an IgA, IgG, IgD, or IgE antibody. In one embodiment, the antibody is an IgG1, IgG2, IgG3, or IgG4 antibody.

"Antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

Exemplary recombinant products that can be produced using the methods described herein include, but are not limited to, those provided in the tables below.

TABLE 2

Exemplary Recombinant Products

| Therapeutic Protein type | Therapeutic | Trade Name |
| --- | --- | --- |
| Hormone | Erythropoietin, Epoein-α | Epogen, Procrit |
| | Darbepoetin-α | Aranesp |
| | Insulin | Humulin, Novolin |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |

TABLE 2-continued

Exemplary Recombinant Products

| Therapeutic Protein type | Therapeutic | Trade Name |
|---|---|---|
| Blood Clotting/Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | RegranexAnril, Kineret |
| | Anakinra (recombinant IL1 antagonist) | |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |
| | Etanercept (TNF receptor/Fc fusion) | Enbrel |
| | Cergutuzumab Amunaleukin | |

TABLE 3

Additional Exemplary Recombinant Products: Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |

TABLE 3-continued

Additional Exemplary Recombinant Products: Bispecific Formats

| Name (other names, sponsoring organizations) | BsAb format | Targets | Proposed mechanisms of action | Development stages | Diseases (or healthy volunteers) |
|---|---|---|---|---|---|
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tubingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |

TABLE 3-continued

Additional Exemplary Recombinant Products: Bispecific Formats

| Name (other names, sponsoring organizations) | BsAb format | Targets | Proposed mechanisms of action | Development stages | Diseases (or healthy volunteers) |
|---|---|---|---|---|---|
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| G5K2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

In one embodiment, the product differs from a polypeptide from Table 2 or 3 at no more than 1, 2, 3, 4, 5, 10, 15, 20, 25, 30, 35, 40, 45, or 50 amino acid residues. In another embodiment, the product differs from a polypeptide from Table 2 or 3 at no more than 1%, 2%, 3%, 4%, 5%, 6%, 7%, 8%, 9%, 10%, or 15% of its amino acid residues.

In one embodiment, the product is a nucleic acid molecule, e.g., a DNA or RNA molecule, or hybrid thereof. In one embodiment, the product is an origami nucleic acid molecule, e.g., an origami DNA, in which the nucleic acid molecule has a predetermined secondary, tertiary, or quaternary structure. In one embodiment, the origami nucleic acid molecule has functional activity. In one embodiment, the product comprises an origami nucleic acid molecule encapsulated in a lipid membrane. In one embodiment, the lipid membrane comprises the cell membrane or components of the cell membrane of the host cell from which it was produced. In one embodiment, the lipid-encapsulated DNA is as described in "Cloaked DNA nanodevices survive pilot mission", Apr. 22, 2014, Wyss Institute for Biologically Inspired Engineering at Harvard University website.

Other recombinant products include non-antibody scaffolds or alternative protein scaffolds, such as, but not limited to: DARPins, affibodies and adnectins.

Other exemplary therapeutic or diagnostic proteins include, but are not limited to any protein described in Tables 1-10 of Leader et al., "Protein therapeutics: a summary and pharmacological classification", Nature Reviews Drug Discovery, 2008, 7:21-39 and as described in Walsh, "Biopharmaceutical benchmarks 2014", Nature Biotechnology, 2014, 32:992-1000 (each incorporated herein by reference); or any conjugate, variant, analog, or functional fragment of the recombinant polypeptides described herein.

Nucleic Acids

Also provided herein are nucleic acids, e.g., exogenous nucleic acids, that encode the lipid metabolism modulators and the recombinant products described herein. The nucleic acid sequences coding for the desired LMM or recombinant product, e.g., recombinant polypeptides, can be obtained using recombinant methods known in the art, such as, for example by screening libraries from cells expressing the desired nucleic acid sequence, e.g., gene, by deriving the nucleic acid sequence from a vector known to include the same, or by isolating directly from cells and tissues containing the same, using standard techniques. Alternatively, the nucleic acid encoding the LMM or recombinant polypeptide can be produced synthetically, rather than cloned. Recombinant DNA techniques and technology are highly advanced and well established in the art. Accordingly, the ordinarily skilled artisan having the knowledge of the amino acid sequence of a recombinant polypeptide described herein can readily envision or generate the nucleic acid sequence that would encode the LMM or the recombinant polypeptide.

Exemplary nucleic acid sequences encoding the LMM SREBF1 and SCD1 are provided as SEQ ID NO: 3 and SEQ ID NO: 4, respectively, herein.

The expression of a desired polypeptide, e.g., a LMM or a recombinant polypeptide, is typically achieved by operably linking a nucleic acid encoding the desired polypeptide or portions thereof to a promoter, and incorporating the construct into an expression vector. The vectors can be suitable for replication and integration into eukaryotic or prokaryotic cells. Typical cloning vectors contain other regulatory elements, such as transcription and translation terminators, initiation sequences, promoters, selection markers, or tags useful for regulation or identification of the expression of the desired nucleic acid sequence.

The nucleic acid sequence encoding the LMM or recombinant polypeptide can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. In embodiments, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193). Vectors derived from viruses are suitable tools to achieve long-term gene transfer since they allow long-term, stable integration of a transgene and its propagation in daughter cells.

A vector may also include, in any of the embodiments described herein, one or more of the following: a signal sequence to facilitate secretion, a polyadenylation signal, a transcription terminator (e.g., from Bovine Growth Hormone (BGH) gene), an element allowing episomal replication and replication in prokaryotes (e.g. SV40 origin and ColE1 or others known in the art), and/or elements to allow selection, e.g., a selection marker or a reporter gene.

In one embodiment, the vector comprising a nucleic acid sequence encoding a polypeptide, e.g., a LMM or a recombinant polypeptide, further comprises a promoter sequence responsible for the recruitment of polymerase to enable transcription initiation for expression of the polypeptide, e.g., the LMM or recombinant polypeptide. In one embodiment, promoter sequences suitable for the methods described herein are usually associated with enhancers to drive high amounts of transcription and hence deliver large copies of the target exogenous mRNA. In an embodiment, the promoter comprises cytomegalovirus (CMV) major immediate early promoters (Xia, Bringmann et al. 2006) and the SV40 promoter (Chernajovsky, Mory et al. 1984), both derived from their namesake viruses or promoters derived therefrom. Several other less common viral promoters have been successfully employed to drive transcription upon inclusion in an expression vector in mammalian cells including Rous Sarcoma virus long terminal repeat (RSV-LTR) and Moloney murine leukemia virus (MoMLV) LTR (Papadakis, Nicklin et al. 2004). In another embodiment, specific endogenous mammalian promoters can be utilized to drive constitutive transcription of a gene of interest (Pontiller, Gross et al. 2008). The CHO specific Chinese Hamster elongation factor 1-alpha (CHEF 1a) promoter has provided a high yielding alternative to viral based sequences (Deer, Allison 2004).

Other promoters suitable for expression in non-mammalian cells, e.g., fungi, insect, and plant cells, are also known in the art. Examples of suitable promoters for directing transcription in a fungal or yeast host cell include, but are not limited to, promoters obtained from the fungal genes of Trichoderma Reesei, methanol-inducible alcohol oxidase (AOX promoter), Aspergillus nidulans tryptophan biosynthesis (trpC promoter), Aspergillus niger var. awamori flucoamylase (glaA), Saccharomyces cerevisiae galactokinase (GAL1), Kluyveromyces lactis Plac4-PBI promoter, or those described in PCT Publication WO 2005/100573. Examples of suitable promoters for directing transcription in an insect cell include, but are not limited to, T7 lac promoter and polyhedrin promoter. An example of a suitable promoter for directing transcription in a plant cell includes, but is not limited to, the cauliflower mosaic virus promoter CaMV35S. Examples of suitable promoters for directing transcription of the nucleic acid constructs of the present invention in a prokaryotic host cell, e.g., a bacterial cell, are the promoters obtained from the E. coli lac operon, E. coli tac promoter (hybrid promoter, DeBoer et al, PNAS, 1983, 80:21-25), E. coli rec A, E. coli araBAD, E. coli tetA, and prokaryotic beta-lactamase. Other examples of suitable promoters include viral promoters, such as promoters from bacteriophages, including a T7 promoter, a T5 promoter, a T3 promoter, an M13 promoter, and a SP6 promoter.

In addition to promoters, the vectors described herein may further comprise an enhancer region as described above; a specific nucleotide motif region, proximal to the core promoter, which can recruit transcription factors to upregulate the rate of transcription (Riethoven 2010). Similar to promoter sequences, these regions are often derived from viruses and are encompassed within the promoter sequence such as hCMV and SV40 enhancer sequences, or may be additionally included such as adenovirus derived sequences (Gaillet, Gilbert et al. 2007).

In one embodiment, the vector comprising a nucleic acid sequence encoding a polypeptide, e.g., a LMM or a recombinant product, described herein further comprises a nucleic acid sequence that encodes a selection marker. In one embodiment, the selectable marker comprises glutamine synthetase (GS); dihydrofolate reductase (DHFR) e.g., an enzyme which confers resistance to methotrexate (MTX); or an antibiotic marker, e.g., an enzyme that confers resistance to an antibiotic such as: hygromycin, neomycin (G418), zeocin, puromycin, or blasticidin.

In one embodiment, the vector comprising a nucleic acid sequence encoding a recombinant product described herein comprises a selection marker that is useful in identifying a cell or cells containing the nucleic acid encoding a recombinant product described herein. In another embodiment, the selection marker is useful in identifying or selecting a cell or cells that containing the integration of the nucleic acid sequence encoding the recombinant product into the genome, as described herein. The identification of a cell or cells that have integrated the nucleic acid sequence encoding the recombinant protein can be useful for the selection and engineering of a cell or cell line that stably expresses the product.

In one embodiment, the vector comprising a nucleic acid sequence encoding a LMM described herein comprises a mechanism for site-specific integration of the nucleic acid sequence encoding the LMM. For example, the vector is compatible with the Flp-In™ system and comprises two FRT sites (comprising a specific nucleotide sequence) that, in the presence of Flp recombinase, directs the recombination and subsequent integration of the desired sequence, e.g., the nucleic acid sequence encoding the LMM, at the desired site, e.g., between the two FRT sites, present in the genome of a Flp-In cell, e.g., a Flp-In CHO cell. Other systems used for site-specific integration of nucleic acids encoding a desired product are known in art, e.g., the Cre-lox recombinase system, or CRISPR/CAS-mediated strategies.

Suitable vectors for use are commercially available, and include vectors associated with the GS Expression System™, GS Xceed™ Gene Expression System, or Potelligent® CHOK1SV technology available from Lonza Biologics, Inc, e.g., pCon vectors. Additional vectors include, but are not limited to, other commercially available vectors, such as, pcDNA3.1/Zeo, pcDNA3.1/CAT, pcDNA3.3TOPO (Thermo Fisher, previously Invitrogen); pTarget, HaloTag (Promega); pUC57 (GenScript); pFLAG-CMV (Sigma-Aldrich); pCMV6 (Origene); or pBK-CMV/pCMV-3Tag-7/pCMV-Tag2B (Stratagene).

Cells and Cell Culture

In one aspect, the present disclosure relates to methods and compositions for engineering or making a cell or cell line that produces a product, e.g., a recombinant polypeptide as described herein. In another aspect, the present disclosure relates to methods and compositions for engineering or making a cell or cell line with improved, e.g., increased productivity and product quality. Characteristics associated with improved productivity and product quality are described herein, for example, in the section titled "Modulation of Lipid Metabolism".

In embodiments, the cell is a mammalian or non-mammalian cell, e.g., an insect cell, a yeast cell, a fungal cell, a plant cell, an archaeal cell, e.g., a cell from a species of Archaea, or a bacterial cell. In an embodiment, the cell is from human, mouse, rat, Chinese hamster, Syrian hamster, monkey, ape, dog, duck, horse, parrot, ferret, fish or cat. In an embodiment, the cell is an animal cell. In embodiments, the cell is a mammalian cell, e.g., a human cell or a rodent cell, e.g., a hamster cell, a mouse cell, or a rat cell. In an embodiment, the cell is a prokaryotic cel, e.g., a bacterial cell. In an embodiment, the cell is a species of Actinobacteria, e.g., *Mycobacterium tuberculosis*).

In one embodiment, the cell is a Chinese hamster ovary (CHO) cell. In one embodiment, the cell is a, CHO-K1, CHOK1SV, Potelligent CHOK1SV (FUT8-KO), CHO GS-KO, Exceed (CHOK1SV GS-KO), CHO-S, CHO DG44, CHO DXB11, CHOZN, or a CHO-derived cell. The CHO FUT8 knockout cell is, for example, the Potelligent® CHOK1 SV (Lonza Biologics, Inc.).

In another embodiment, the cell is a HeLa, HEK293, HT1080, H9, HepG2, MCF7, Jurkat, NIH3T3, PC12, PER.C6, BHK (baby hamster kidney cell), VERO, SP2/0, NSO, YB2/0, Y0, EB66, C127, L cell, COS, e.g., COS1 and COS7, QC1-3, CHO-K1, CHOK1SV, Potelligent CHOK1SV (FUT8-KO), CHO GS-KO, Exceed (CHOK1SV GS-KO), CHO-S, CHO DG44, CHO DXB11, CHOZN, or a CHO-derived cell, or any cells derived therefrom. In one embodiment, the cell is a stem cell. In one embodiment, the cell is a differentiated form of any of the cells described herein. In one embodiment, the cell is a cell derived from any primary cell in culture.

In an embodiment, the cell is any one of the cells described herein that produces a product, e.g., a product as described herein. In an embodiment, the cell is any one of the cells described herein that comprises an exogenous nucleic acid encoding a recombinant polypeptide, e.g., expresses a recombinant polypeptide, e.g., a recombinant polypeptide selected from Table 2 or 3.

In an embodiment, the cell culture is carried out as a batch culture, fed-batch culture, draw and fill culture, or a continuous culture. In an embodiment, the cell culture is an adherent culture. In an embodiment, the cell culture is a suspension culture. In one embodiment, the cell or cell culture is placed in vivo for expression of the recombinant polypeptide, e.g., placed in a model organism or a human subject.

In one embodiment, the culture medium is free of serum. Other suitable media and culture methods for mammalian cell lines are well-known in the art, as described in U.S. Pat. No. 5,633,162 for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1p. 173 ff, 1963), Dulbecco's modified Eagle's medium (DMEM), Eagle's minimal essential medium (MEM), Ham's F12 medium (Ham, R. et al., Proc. Natl. Acad. Sc.53, p288 ff. 1965) or Iscoves' modified DMEM lacking albumin, transferrin and lecithin (Iscoves et al., J. Exp. med. 1, p. 923 ff., 1978). For instance, Ham's F10 or F12 media were specially designed for CHO cell culture. Other media specially adapted to CHO cell culture are described in EP-481 791. Other suitable cultivation methods are known to the skilled artisan and may depend upon the recombinant polypeptide product and the host cell utilized. It is within the skill of an ordinarily skilled artisan to determine or optimize conditions suitable for the expression and production of the product, e.g., the recombinant polypeptide, to be expressed by the cell.

Methods for Engineering a Cell and Producing a Product

The methods and compositions described herein are useful for engineering a cell or cell line with improved productivity and improved product quality. In embodiments, a cell is modified such that the lipid metabolism of the cell is modulated. For example, an exogenous nucleic acid encoding an LMM is introduced into the cell. The cell is subsequently cultured under conditions suitable for the expression of the LMM and LMM-mediated modulation of lipid metabolism. The characteristics of a cell having its lipid metabolism modulated are described herein, e.g., in the section titled "Modulation of Lipid Metabolism".

In some embodiments, the cell further comprises an exogenous nucleic acid that encodes a product, e.g., a recombinant polypeptide. In another embodiment, the cell further comprises an exogenous nucleic acid that increases the expression of an endogenous product. In any of such embodiments, the exogenous nucleic acid that encodes a product or increases expression of an endogenous product is introduced prior to the modification of lipid metabolism, e.g., the introduction of an exogenous nucleic acid encoding a LMM described herein. Alternatively, in other embodiments, the exogenous nucleic acid that encodes a product or increases expression of an endogenous product is introduced after the modification of lipid metabolism, e.g., the introduction of an exogenous nucleic acid encoding a LMM described herein. In any of the embodiments, the product is a therapeutic or diagnostic protein. In any of the embodiments, the product is selected from Table 2 or 3.

Methods for genetically modifying or engineering a cell to express a desired polypeptide or protein, e.g., an LMM described herein or a product described herein, are well known in the art, and include, for example, transfection, transduction (e.g., viral transduction), or electroporation.

Physical methods for introducing a nucleic acid, e.g., an exogenous nucleic acid or vector described herein, into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Chemical means for introducing a nucleic acid, e.g., an exogenous nucleic acid or vector described herein, into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

Nucleic acids containing the sequence for a desired polypeptide, e.g., a LMM and/or product described herein, are delivered into a cell and can be integrated into its genome via recombination. The resulting recombinant cells are then capable of stable expression of the desired polypeptide, e.g., a LMM and/or product described herein, thus enabling consistent and efficient protein production over long periods of time. Several advantages accompany stable integration of a gene of interest including the fact that only a single DNA delivery process is required to induce prolonged expression since the gene of interest is simultaneously replicated with host chromosomes; this means that the gene is transferred from one generation to the next without the necessity for additional machinery. This also, in theory, produces a more consistent product and yield across batch-to-batch fermentations. In line with this, stable expression methods are capable of generating high product yields compared to those generated without a modification that modulates lipid metabolism described herein, e.g., introduction of an exogenous nucleic acid encoding a LMM.

Protocols to establish recombinant cell lines that stably overexpress the desired polypeptides, e.g., a LMM and/or product described herein, typically involve integration of linearized DNA (usually plasmid based) at random sites into the host genome facilitated by random recombination. Site specific protocols have also been developed and implemented which promote integration of an expression cassette at specific regions of the host genome (O'Gorman, Fox et al. 1991). These protocols often exploit recombinases capable of site specific recombination, and include, but are not limited to, the Flp-In™ system (e.g., utilizing Flp-In CHO cells), CHOK1SV Flp cell line (Lonza) (as described in Zhang L. et al. (2015). Biotechnol. Prog. 31:1645-5; incorporated by reference herein in its entirety), or the Cre-lox system.

As described above, in some embodiments, the vector comprising a nucleic acid encoding a product and/or a LMM, further comprises a selection marker to facilitate selection of successfully expressing cells from a transfected pool (Browne, Al-Rubeai 2007). Although numerous selection methods are commercially available, the most commonly used of these are methotrexate (MTX) and Lonza's glutamine synthetase (GS) system (Bebbington, Renner et al. 1992, Lai, Yang et al. 2013). Dihydrofolate reductase (DHFR) is a protein responsible for the conversion of folic acid to tetrahydrofolate and is necessary for essential biosynthetic pathways that produce glycine, purines, and thymidylic acid. MTX can be used to inhibit DHFR activity and inclusion of DHFR in a stably transfected culture can therefore be used to select for stably integrated cells; only those cells successfully expressing sufficient recombinant DHFR will survive selection using MTX (Cacciatore, Chasin et al. 2010). Another selection method commonly employed is the use of GS; an enzyme responsible for the synthesis of glutamine from glutamate and ammonia and, since glutamine is vital for mammalian cell survival, cells lacking sufficient GS will not survive in culture. Initially the addition of methionine sulphoximine (MSX), an inhibitor of GS, ensures that the presence of endogenous GS in CHOK1SV cells is not adequate to maintain cell survival and therefore only cells expressing additional GS brought about through stable integration of a recombinant construct survive the selection process. Lonza and others have now established CHO host cell lines in which the endogenous GS gene has been knocked down/out such that all cells perish that are not successfully integrated with the construct of interest without the presence of exogenous glutamine in the media (Fan, Kadura et al. 2012). Many other selection methods are available which elicit a resistance to a particular selection agent such that only cells harboring the resistance gene will survive the selection process; these include hygromycin, neomycin, blasticidin and zeocin (Browne, Al-Rubeai 2007). In embodiments, the vector comprising an exogenous nucleic acid encoding a LMM and the vector comprising an exogenous nucleic acid encoding a product, e.g., a recombinant polypeptide as described herein, further comprise different selection markers.

Following the successful recovery of stably expressing cell pools, the isolation of individual clones, originating from a single cell, facilitates' the selection of cell lines that are capable of high product yields and quality, or the cell lines with the highest capability of high product yields and high quality product. Differences in cellular properties are likely associated with heterogeneity observed in cells and both the number and specific integration site(s) of recombinant DNA. Clonal screening properties have therefore been developed to rapidly assess multiple clones and subsequently select high expressing cells. Fluorescence Activated Cell Sorting (FACS) is a method which can rapidly sort cells based on fluorescence intensity and therefore can be employed to select for high expressing clones. Several protocols have been established which involve fluorescent tagging of the protein of interest (Powell, Weaver 1990), fluorescent tagging of cell surface molecules co-expressed with the recombinant gene (Holmes, Al-Rubeai 1999) and detection of fluorescence intensity based on eGFP expression co-expressed with the gene of interest (Meng, Liang et al. 2000). A high fluorescence intensity observed with these methods suggests a high level of recombinant protein production and thus these cells can be preferentially selected from a recombinant cell pool. FACS-based selection methods to isolate high expressing recombinant clones are more suited to recombinant products which remain associated with the cell and, since mammalian expressed biotherapeutic recombinant protein products are secreted, methods have been developed which are more appropriate for the selection of clones for secreted recombinant proteins. For example, ClonePix is an automated colony selection method which picks clones grown on a semi-solid media based on secretion of recombinant products into the media surrounding the colony and associating with Fluorescin Isothiocyanante (FITC) therefore creating a fluorescent halo around the colonies (Lee, Ly et al. 2006). Clones are selected based on the fluorescence intensity of the halo surrounding the colony. Many other clone selection protocols have been established which rapidly isolate recombinant cells based on desired biological properties with particular interest on productivity and are reviewed in Browne and Al-Rubeai (Browne, Al-Rubeai 2007). Expansion of a clone selected as described herein results in the production of a cell line.

In one embodiment, the methods described herein produce a cell with improved productivity. Improved productivity or production capacity of a cell includes a higher yield or amount of product that is produced, and/or an increased rate of production (as determined by the yield or amount of product produced over a unit of time). In one embodiment, improvement of the productivity of a cell, e.g., the capacity to produce a product, results in an increase, e.g., a 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% increase; or a 1-fold, 2-fold, 3-fold, 4-fold, 5-fold, 6-fold, 7-fold, 8-fold, 9-fold, 10-fold, 20-fold, 50-fold, or 100-fold, or more increase in the amount, level, or quantity of product produced, e.g., compared to the amount, level, or quantity of product produced by a cell that does not have a lipid metabolism pathway modulated. In one embodiment, improvement of the productivity of a cell, e.g., the rate of production of the product, results in an increase, e.g., a 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% increase; or a 1-fold, 2-fold, 3-fold, 4-fold, 5-fold, 6-fold, 7-fold, 8-fold, 9-fold, 10-fold, 20-fold, 50-fold, or 100-fold, or more increase in the rate of production of the product, e.g., compared to the rate of production of the product produced by a cell that does not have a lipid metabolism pathway modulated.

The methods described herein for engineering a cell produce a high production cell or a high production cell line. A high production cell or cell line is capable of producing higher yields of a recombinant polypeptide product than compared to a reference cell or a cell that has not been selected or engineered by the methods described herein. In an embodiment, a high production cell line is capable of producing 100 mg/L, 200 mg/L, 300 mg/L, 400 mg/L, 500 mg/L, 600 mg/L, 700 mg/L, 800 mg/L, 900 mg/L, 1 g/L, 2 g/L, 3 g/L, 4 g/L, 5 g/L, 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, or 100 g/L or more of a product, e.g., a recombinant polypeptide product. In an embodiment, a high production cell line is produces 100 mg/L, 200 mg/L, 300 mg/L, 400 mg/L, 500 mg/L, 600 mg/L, 700 mg/L, 800 mg/L, 900 mg/L, 1 g/L, 2 g/L, 3 g/L, 4 g/L, 5 g/L, 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, or 100 g/L or more of a product, e.g., a recombinant polypeptide product. The quantity of product produced may vary depending on the cell type, e.g., species, and the product, e.g., recombinant polypeptide, to be expressed. By way of example, a high production CHO cell that expresses a monoclonal antibody may be capable of producing at least 1 g/L, 2 g/L, 5 g/L, 10 g/L, 15 g/L, 20 g/L, or 25 g/L of a monoclonal antibody.

Described herein are methods and compositions that may be particularly useful for the expression of products that are difficult to express or produce in cells or cell-free systems using the conventional methods presently known in the art. As such, a production cell line producing such difficult to express products, e.g., next generation biologics described herein, may produce at least 1 mg/L, 5 mg/L, 10 mg/L, 15 mg/L, 20 mg/L, 25 mg/L, 30 mg/L, 35 mg/L, 40 mg/L, 45 mg/L, 50 mg/L, 55 mg/L, 60 mg/L, 65 mg/L, 70 mg/L, 75 mg/L, 80 mg/L, 85 mg/L, 90 mg/L, 95 mg/L, or 100 mg/L or more. Production capacity (e.g., yield, amount, or quantity of product or rate of production of product) achieved by the methods and compositions described herein for difficult to express proteins can be increased by 5%, 10%, 20%, 30%, 40%, 50%, 60%, 70%, 80%, 90%, 95%, 99%, or more, or 1-fold, 2-fold, 3-fold, 4-fold, 5-fold, 10-fold, 20-fold, 50-fold, or 100-fold or more, in comparison to the production capacity of a cell or system that does not have a modification that modulates lipid metabolism as described herein.

Assays for quantifying the amount, level, or quantity of product produced or secreted, e.g., secreted into the culture media, include protein quantification assays, such as the Bradford protein assay, SDS-PAGE analysis, immunoblotting, e.g., western blot, and automated means, e.g., using a nanodrop device. Other methods for measuring increased protein production are well-known to those skilled in the art. For example, an increase in recombinant protein production might be determined at small-scale by measuring the concentration in tissue culture medium by ELISA (Smales et al. 2004 Biotechnology Bioengineering 88:474-488). It can also be determined quantitatively by the ForteBio Octet, for example for high throughput determination of recombinant monoclonal antibody (mAb) concentration in medium (Mason et al. 2012 Biotechnology Progress 28:846-855) or at a larger-scale by protein A HPLC (Stansfield et al. 2007 Biotechnology Bioengineering 97:410-424). Other methods for determining production of a product, e.g., a recombinant polypeptide described herein, can refer to specific production rate (qP) of the product, in particular the recombinant polypeptide in the cell and/or to a time integral of viable cell concentration (IVC). In an embodiment, the method for determining production includes the combination of determining qP and IVC. Recombinant polypeptide production or productivity, being defined as concentration of the polypeptide in the culture medium, is a function of these two parameters (qP and IVC), calculated according to Porter et al. (Porter et al. 2010 Biotechnology Progress 26:1446-1455). Methods for measuring protein production are also described in further detail in the Examples provided herein.

In one embodiment, the methods described herein produce a cell with improved product quality. In one embodiment, improvement of the quality of the product results in the increase, e.g., a 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99%, or more, increase in product quality; or a 1-fold, 2-fold, 3-fold, 4-fold, 5-fold, 6-fold, 7-fold, 8-fold, 9-fold, 10-fold, 20-fold, 50-fold, or 100-fold, or more increase, in product quality, e.g., as compared to the amount, level, or quantity of product produced by a cell that does not have a lipid metabolism pathway modulated. Such increases in product quality can be exemplified, for example, by one or more of the following:

i) an increase in the amount or quantity of non-aggregated product (or a decrease in the amount or quantity of aggregated product);

ii) an increase in the amount or quantity of properly folded or assembled product (or a decrease in the amount or quantity of misfolded, unfolded, partially assembled, or non-assembled product), or an increase in the ratio of properly folded or assembled product to unfolded, misfolded, partially assembled, or non-assembled product;

iii) an increase in the amount or quantity of full-length product (or a decrease in fragmentation of the product);

iv) an increase in the desired post-translational modifications (or a decrease in unmodified or incorrectly modified product);

v) an increase or decrease in glycan heterogeneity (e.g., for glycosylated products); vi) an increase in the amount or quantity of functional product (or a decrease in the amount or quantity of a nonfunctional or dysfunctional product), or an increase in the ratio of function to nonfunctional or dysfunctional product; and/or vii) an increase or decrease in disulfide bond scrambling (e.g., an increase or decrease the desired isoform or structure as a result to increased or decreased disulfide bond scrambling, e.g., for antibody molecule products).

Methods for measuring product quality, e.g., the improvement of the product quality, of a cell or cell line generated as described herein are known in the art. In one embodiment, methods for determining the fidelity of the primary sequence of the expressed recombinant polypeptide product are known in the art, e.g., mass spectrometry. An increase in the amount or concentration of properly folded product, e.g., expressed recombinant polypeptide, can be determined by circular dichroism or assessing the intrinsic fluorescence of the expressed recombinant polypeptide. An increase in the amount or concentration of functional product can be tested using various functional assays depending on the identity of the recombinant product, e.g., recombinant polypeptide. For example, antibodies can be tested by the ELISA or other immunoaffinity assay. Other methods for determining an increase in product quality, e.g., determining aggregation, post-translational modifications, disulfide bond scrambling, can be assessed by size exclusion chromatography, high performance liquid chromatography, dynamic light scattering (DLS) approaches, and protein electrophoresis (PAGE) methods.

In an embodiment, the methods for producing a product, e.g., as described herein, comprise providing a cell engineered to comprise a modification that modulates lipid metabolism, as described above. In one embodiment, the cell comprising a modification that modulates lipid metabolism further comprises an exogenous nucleic acid encoding a product, e.g., a recombinant polypeptide as described herein. In one embodiment, the exogenous nucleic acid encoding a product, e.g., a recombinant polypeptide described herein is introduced to the engineered cell comprising a modification that modulates lipid metabolism. In another embodiment, the exogenous nucleic acid encoding a product, e.g., a recombinant polypeptide described herein, is introduced to a cell prior to the introduction of an exogenous nucleic acid encoding a LMM as described herein. The exogenous nucleic acid encoding a product further comprises a selection marker, for efficient selection of cells that stably express, e.g., overexpress, the product as described herein.

In some embodiments, additional steps may be performed to improve the expression of the product, e.g., transcription, translation, and/or secretion of the product, or the quality of the product, e.g., proper folding and/or fidelity of the primary sequence. Such additional steps include introducing an agent that improves product expression or product quality. In an embodiment, an agent that improves product expression or product quality can be a small molecule, a polypeptide, or a nucleic acid that encodes a polypeptide that improves protein folding, e.g., a chaperone protein. In an embodiment, the agent that assists in protein folding comprises a nucleic acid that encodes a chaperone protein, e.g., BiP, PD1, or ERO1 (Chakravarthi & Bulleid 2004; Borth et al. 2005; Davis et al. 2000). Other additional steps to improve yield and quality of the product include overexpression of transcription factors such as XBP1 and ATF6 (Tigges & Fussenegger 2006; Cain et al. 2013; Ku et al. 2008) and of lectin binding chaperone proteins such as calnexin and calreticulin (Chung et al. 2004). Overexpression of the agents that assist or improve protein folding, product quality, and product yield described herein can be achieved by introduction of exogenous nucleic acids encoding the agent. In another embodiment, the agent that improves product expression or product quality is a small molecule that can be added to the cell culture to increase expression of the product or quality of the product, e.g., DMSO. In one embodiment, culturing the cells at a lower temperature, e.g., 1° C., 2° C., 3° C., 4° C., 5° C., 6° C., 7° C., 8° C., 9° C., or 10° C. lower, than the temperature that the cells are normally grown can improve productivity.

Any of the methods described herein can further include additional selection steps for identifying cells that have high productivity or produce high quality products. For example, FACS selection can be utilized to select specific cells with desired characteristics, e.g., higher expression of a protein folding proteins, e.g., chaperones.

In one aspect, the disclosure provides methods that include a step for recovering or retrieving the recombinant polypeptide product. In embodiments where the recombinant polypeptide is secreted from the cell, the methods can include a step for retrieving, collecting, or separating the recombinant polypeptide from the cell, cell population, or the culture medium in which the cells were cultured. In embodiments where the recombinant polypeptide is within the cell, the purification of the recombinant polypeptide product comprises separation of the recombinant polypeptide produced by the cell from one or more of any of the following: host cell proteins, host cell nucleic acids, host cell lipids, and/or other debris from the host cell.

In embodiments, the process described herein provides a substantially pure protein product. As used herein, "substantially pure" is meant substantially free of pyrogenic materials, substantially free of nucleic acids, and/or substantially free of endogenous cellular proteins enzymes and components from the host cell, such as polymerases, ribosomal proteins, and chaperone proteins. A substantially pure protein product contains, for example, less than 25%, 20%, 15%, 10%, 9%, 8%, 7%, 6%, 5%, 4%, 3%, 2%, or 1% of contaminating endogenous protein, nucleic acid, or other macromolecule from the host cell.

Methods for recovering and purification of a product, e.g., a recombinant polypeptide, are well established in the art. For recovering the recombinant polypeptide product, a physical or chemical or physical-chemical method is used. The physical or chemical or physical-chemical method can be a filtering method, a centrifugation method, an ultracentrifugation method, an extraction method, a lyophilization method, a precipitation method, a chromatography method or a combination of two or more methods thereof. In an embodiment, the chromatography method comprises one or more of size-exclusion chromatography (or gel filtration), ion exchange chromatography, e.g., anion or cation exchange chromatography, affinity chromatography, hydrophobic interaction chromatography, and/or multimodal chromatography.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Generation of Stable Cells Overexpressing a Lipid Metabolism Modulator In order to investigate the effect of overexpression of two lipid metabolism modulators, SCD1 and SREBF1, in CHO cells, these genes were successfully cloned and stably integrated into adherent CHO Flp-In cells using a site directed approach, and into suspension GS knockout (GSKO) CHO cells using a random integration approach.

Molecular Cloning of SCD1 and SREBF1 Containing FRT Vectors

Molecular cloning was carried out in order to generate FRT based vectors which facilitate the expression of SCD1 and SREBF1 proteins both with and without a V5/His tag at the C-terminus of each protein. The use of these vectors, in conjunction with Thermo Fisher's commercially available Flp-In host CHO cell pool enabled site specific integration of the genes of interest to generate stable CHO adherent cell pools. The primers described in Table 4 were used in a Phusion® Polymerase based PCR reaction to amplify these genes such that double stranded DNA fragments were produced flanked by the restriction sites also detailed in Table 4. SCD1 and SREBF1 genes were amplified from Mouse P19 derived cDNA and Origene mouse cDNA clone (NCBI accession no. NM_011480), respectively.

Following successful amplification of the target genes, double restriction digests were undertaken on FRT-V5 vectors as well as the previously generated PCR products of the genes of interest using the appropriate restriction enzymes. Ligations were incubated overnight before subsequent transformations and miniprep purification was carried out on the resulting colonies.

Generation of SCD1 and SREBF1 Overexpressing Adherent Flp-In CHO Cells

The aforementioned FRT-based constructs were used in conjunction with Thermo Fisher's commercially available adherent Flp-In CHO cells to generate stable cell pools. FRT vectors containing the genes of interest and an empty FRT construct (used to generate a control cell pool) were co-transfected with recombinase containing pOG44 vector into Flp-In cells. Recombinase sites present in the FRT vectors and Flp-In CHO genome initiate site specific recombination and successful clones can be isolated using hygromycin as a selection agent. Stably expressing recombinant CHO adherent cell pools in a site specific manner were generated according to the manufacturer's instructions, e.g., as described in the Thermo Fisher's Flp-In manual, e.g., available from the Thermo Fisher's references and protocols website. This method was used to generate and recover control, SCD1-V5, and SREBF1-V5 Flp-In CHO polyclonal cell pools.

Molecular Cloning of SCD1 and SREBF1 into pcDNA3.1 Vectors

Expression vectors were generated to stably integrate, and therefore overexpress, in industrially relevant CHO suspension cells with one of SCD1, SREBF1 or a truncated SREBF1 gene. The pcDNA3.1V5-His/TOPO vector consists of an appropriate CMV promoter and downstream multiple cloning site, facilitating expression of the gene of interest, while also including elements enabling expression of a neomycin gene which can be utilized for selection of successful clones following integration of DNA into the genome.

Initially, the Phusion® PCR protocol was used to amplify SCD1, SREBF1 and a SREBF1 truncation using the primers indicated in Table 4, designed so that restriction sites were simultaneously added to the flanks of the resulting PCR products. The previously generated SCD1-FRT vector was used as a template to amplify the SCD1 genes while Origene mouse cDNA (NCBI accession no. NM_011480) was used to amplify the SREBF1 gene and its truncation. The SREBF1 truncation hereby referred to as SREB410, codes for a 410 amino acid long polypeptide sequence, which includes the helix-loop-helix (HLH) domain of SREBF1. This domain is endogenously cleaved from the full-length protein allowing migration of this fragment to the nucleus and subsequent gene transcription activation as previously outlined. Primers were designed to amplify this region with the aim to express a protein (encoded by this sequence) which is localized directly in the nucleus and thus to carry out its function as a transcriptional activator without the need for endogenous processing.

Double restriction digests were carried out on purified PCR products as appropriate (see Table 4), and pcDNA3.1/V5-His/TOPO, where primers amplified a gene with no stop codon, in order to allow read through into an in-frame sequence encoding a V5 and His tag. The resulting DNA fragments were ligated to yield vectors containing SCD1, SREBF1 or SREB410 genes with a V5-His tag. These reactions were transformed and mini preps were carried out on a number of the resulting colonies. Restriction digests were carried out and the resulting DNA fragments were run on an agarose gel to ascertain which samples were successful.

Generation of SCD1 and SREBF1 Overexpressing Suspension GSKO CHO Cells

Suspension CHOK1SV GS-KO cell pools grown in chemically-defined, protein and serum-free media, stably transfected with the previously synthesized pcDNA3.1V5-His/TOPO derived constructs were generated in order to investigate the effect of constitutive expression of the inserted genes in an industrially relevant cell line. In order to achieve this, stable integration was carried out using Lonza's CHOK1SV GS-KO host cell line. Initially, SCD1-V5, SREBF1-V5, SREB410-V5 and control (empty pcDNA3.1V5-His/TOPO) constructs were linearized by overnight digestion with PvuI restriction enzyme (NEB). Following linearization, DNA was purified using ethanol precipitation and CHOK1SV GS-KO cells were electroporated using 20 μg DNA and $1 \times 10^7$ viable cells before immediate transfer to T75 flasks containing CD-CHO medium (Thermo Fisher) at 37° C. to make a final volume of 20 mL. Flasks were placed in a humidified static incubator at 37° C. with a 5% $CO_2$ in air atmosphere for 24 hours. A concentrated stock of G418 (Melford) selection agent was diluted in CD-CHO medium and 5 mL of this stock was added to the T75 flasks and gently mixed to yield a final concentration of 750 μg/mL in a 25 mL total volume. Cell counts were performed every 3-4 days to determine growth and culture viability and 750 μg/ml G418 in CD-CHO media was renewed approximately every 6 days by centrifugation and resuspension. Cells were transferred to 125 mL Erlenmeyer flasks and routine suspension cell culture was established once cells had reached a concentration of $2 \times 10^5$ viable cells/mL.

TABLE 4

Summary of primer sequences

| Primer Name | Primer Sequence (5'-3') | Restriction Sites | SEQ ID NO: |
|---|---|---|---|
| eGFP SV40 For | TAT GCTAGC GGTACCATGGTGAGCAAGGGCGAGGA | NheI, KpnI* | 5 |
| SREBF1 For FRT | TAT GGTACC ATGGACGAGCT | KpnI | 6 |
| SREBF1 Rev FRT | ATA GGGCCC TTAGCTGGAA | ApaI | 7 |
| SREBF1 V5 For FRT | TAT GCGGCCGC ATGGACGAG | NotI | 8 |
| SREBF1 V5 Rev | ATA CTCGAG CGGCTACTCTT | ApaI | 9 |
| SCD1 For FRT | TAT GGTACC ATGCCGGCC | KpnI | 10 |
| SCD1 Rev FRT | ATA CTCGAG TCAGCTACTCTTGT | XhoI | 11 |
| SCD1 V5 For FRT | TAT GGTACC ATGCCGGCC | KpnI | 12 |
| SCD1 V5 Rev FRT | ATA CTCGAG CGGCTACTCTT | XhoI | 13 |
| SREBF1 For 3.1 | TAT GCGGCCGC ATGGACGAG | NotI | 14 |
| SREBF1 Rev 3.1 | ATA TCTAGA CTAGCTGGAAGTGACGGTGGTTCC | XbaI | 15 |
| SREBF1 V5 For 3.1 | TAT GCGGCCGC ATGGACGAG | NotI | 16 |
| SREBF1 V5 Rev 3.1 | ATA TCTAGA CTGCTGGAAGTGACGGTGGTTC | XbaI | 17 |
| SREB410 For 3.1 | TAT GCGGCCGC ATGGACGAG | NotI | 18 |
| SREBF410 Rev 3.1 | ATA TCTAGA TCACATGCCCTCCATAGACACATCTGTG | XbaI | 19 |
| SREB410 V5 For | TAT GCGGCCGC ATGGACGAG | NotI | 20 |
| SREB410 V5 Rev | ATA TCTAGA CTCATGCCCTCCATAGACACATCTGTG | XbaI | 21 |
| SCD1 For 3.1 | TAT GGTACC ATGCCGGCC | KpnI | 22 |
| SCD1 Rev 3.1 | ATA CTCGAG TCAGCTACTCTTGT | XhoI | 23 |
| SCD1 V5 For 3.1 | TAT GGTACC ATGCCGGCC | KpnI | 24 |
| SCD1 V5 Rev 3.1 | ATA CTCGAG CGGCTACTCTT | XhoI | 25 |

Example 2: Expression Analysis of LMM in Stable Cells Overexpressing a LMM

Figure 1:
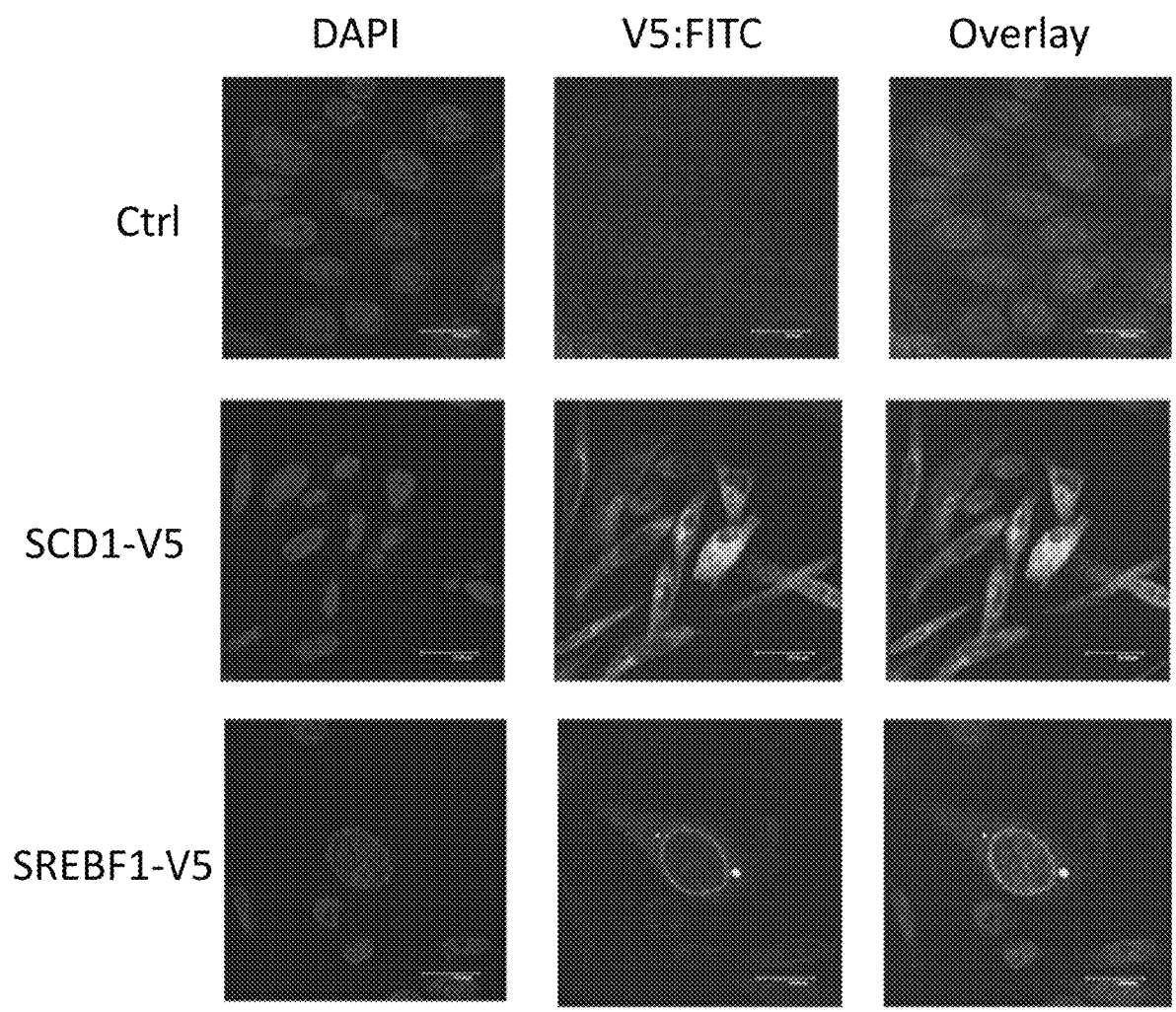
FIG. 1 is a series of immunofluorescent images obtained of Flp-In CHO engineered cell pools, separately transfected with either a control expression vector (Ctrl), or ones encoding SCD1 fused at its C-terminus to a V5 epitope tag (SCD1-V5) or SREBF1 fused at its C-terminus to a V5 epitope tag (SREBF1-V5). The pools were imaged with an anti-V5 primary antibody and a secondary anti-mouse FITC antibody (middle images) as well as DAPI (left images) and an overlay of both the left and middle images (right hand column) is shown. Images were generated using a Leica Confocal Microscope.

Following the establishment of stable Flp-In CHO cell pools stably integrated with either a control (empty pcDNA5 FRT), SCD1-V5 or SREBF1 V5, immunofluorescence was undertaken to confirm both the expression of the stably exogenous integrated genes and additionally the intracellular location of the expressed proteins. Control, SCD1-V5 and SREBF1-V5 cell lines were seeded at 2×10⁵ viable cells per well in a 24 well plate in Ham Nutrient Mix F12 medium supplemented with 10% FBS. Samples were methanol-fixed and first exposed to anti-V5 antibody (produced in mouse-Sigma V8012) and successively anti-mouse FITC secondary conjugate (raised in goat-Sigma F0257). Furthermore, the cells were exposed to DAPI stain (10 µg/mL working stock) in order to stain cellular DNA thus highlighting the nuclei. The resulting immunofluorescent images are shown in FIG. 1.

The presence of the FITC stains in SCD1-V5 and SREBF1-V5 cell lines shows that the exogenous/recombinant genes were successfully expressed and, moreover, the cellular localization of SCD1-V5 and SREBF1-V5 proteins was clearly evident. Constitutively expressed SCD1-V5 protein was present and abundant throughout the cell, with the images showing their localization to be in the cytoplasm and in the ER. Conversely, the SREBF1-V5 protein was expressed to a much lower amount, but it was very prominently located at the peri-nucleus forming a ring around the nuclei. It is important to consider that the V5 epitope sequence was added to the 3' end of the gene and, because of the natural regulation of SREBF1, specific domains are cleaved and relocated within the cell. The mature, cleaved bHLH (basic helix loop helix) region is of particular importance as it is responsible for transcriptional activation of many genes with implications on lipid biosynthesis and conformation. Because this region is encoded at the 5' end of the gene, this region would not be detected upon staining of the 3' V5 tag and thus it is impossible to determine whether any of the constitutively expressed, cleaved portion of the translated protein is present in the imaged cells.

Figure 2:
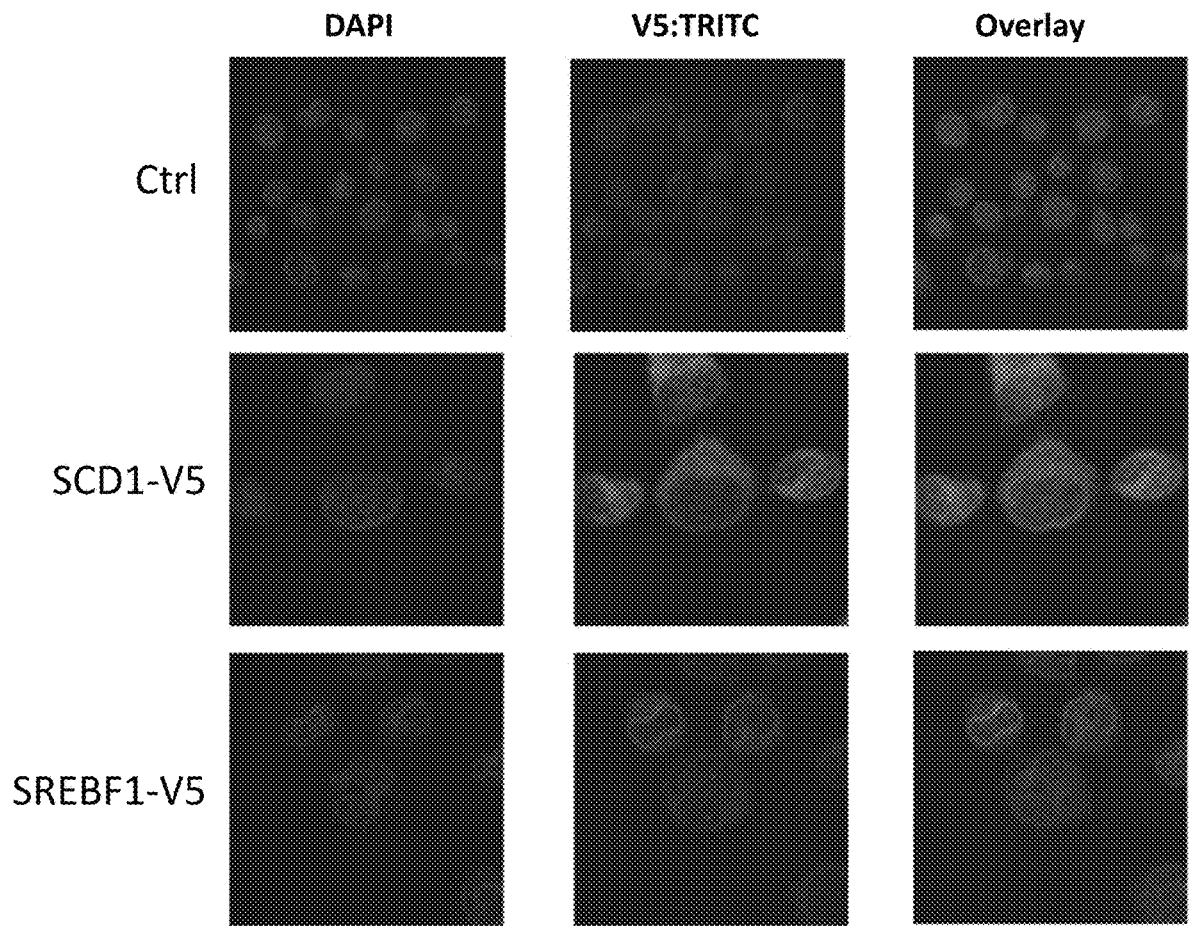
FIG. 2 shows a series of immunofluorescent images obtained of CHOK1SV glutamine synthetase knock-out (GS-KO) cell pools, transfected with either a control expression vector (Ctrl), or ones encoding SCD1-V5 or SREBF1-V5. The pools were imaged with an anti-V5 primary and anti-mouse secondary TRITC antibody (middle images) as well as DAPI (left images) and an overlay of both the left and middle images (right hand column) is also shown. Images were generated using a Leica Confocal Microscope.

Staining of intracellular V5-tagged stable proteins was carried out to determine the presence of SCD1-V5 and SREBF1-V5 in engineered CHOK1SV GS-KO suspension cell lines. In order to adhere these cells to a coverslip in a 24 well plate, coverslips were first treated with poly-L-lysine and cells were seeded at 2×10⁵ cells per well and left to incubate at 37° C. in a 5% CO₂ environment static humidified incubator overnight. Following methanol fixing and permeablisation, anti-V5 (produced in mouse—Sigma V8012) was conjugated with anti-mouse TRITC (produced in goat-T5393) secondary antibody. The resulting images are shown in FIG. 2.

Western blots were performed using an anti-V5 antibody, an anti-mouse HRP conjugated secondary antibody, and the appropriate detection system, was used to further confirm expression of the lipid constructs with the V5 tag. Equivalent amounts of total protein (determined using the Bradford assay) were loaded for SDS-PAGE followed by western blotting onto nitrocellulose. The resulting blots are shown in FIGS. 3A, 3B, and 3C with the V5 tag only detected in those cells expressing the SCD1 construct. However, the low levels of expression achieved with the SREBF1 construct may explain the lack of detection of V5 in cell lines expressing this construct.

Example 3: Growth Characteristics of Stable Cells Overexpressing a LMM

In this example, the growth characteristics, such as viable cell counts, cell number, and culture viability were assessed in two different cell lines engineered to overexpress LMMs, a CHO Flp-In™ and the CHOK1SV GS-KO (Lonza Biologics) cell lines. The LMM-engineered cell lines were generated as described in Example 1. Control cell lines were engineered to express an empty V5 tagged expression vector. An eGFP encoding expression vector was transfected into the LMM-engineered cell lines by electroporation. Electroporations were carried out using $1\times10^7$ viable LMM-engineered Flp-In CHO cells or CHOK1SV GS-KO cells and 20 μg of plasmid DNA (eGFP encoding expressing vector) and these cells were diluted to a final volume of about 20 or 32 mL in Ham Nutrient Mix F12 medium. Viable cell concentrations were determined using a ViCell cell counter and recorded at 24, 48, 72, and 96 hours post transfection of the eGFP encoding expression vector.

Figure 4:
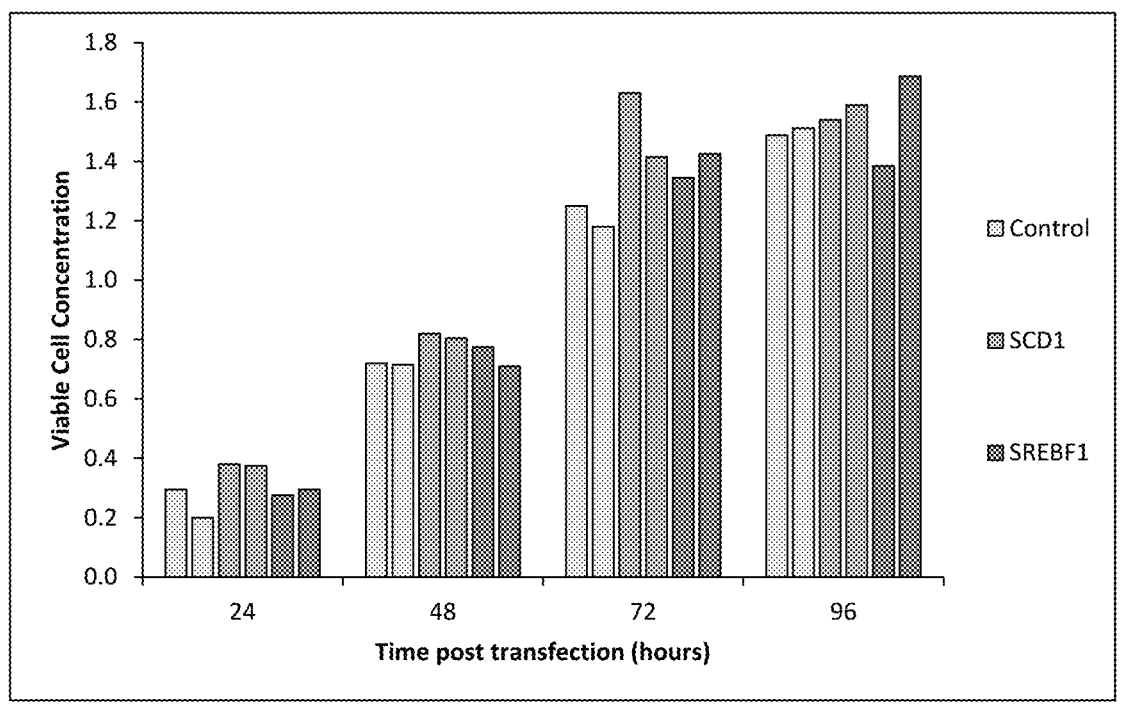
FIG. 4 shows the viable cell concentration, as determined using a ViCell cell counter, of the CHO Flp-In cell pools engineered to stably overexpress the LMM SCD1-V5 and SREBF1-V5 post transfection with eGFP-containing construct JB3.3 (n=2).

The results for the Flp-In™ cells engineered to express SCD1 and SREBF1 are shown in FIG. 4. Cells overexpressing SCD1 and SREBF1 generally showed some increase in the viable cell concentration compared to control cells across all time points.

Figure 5A:
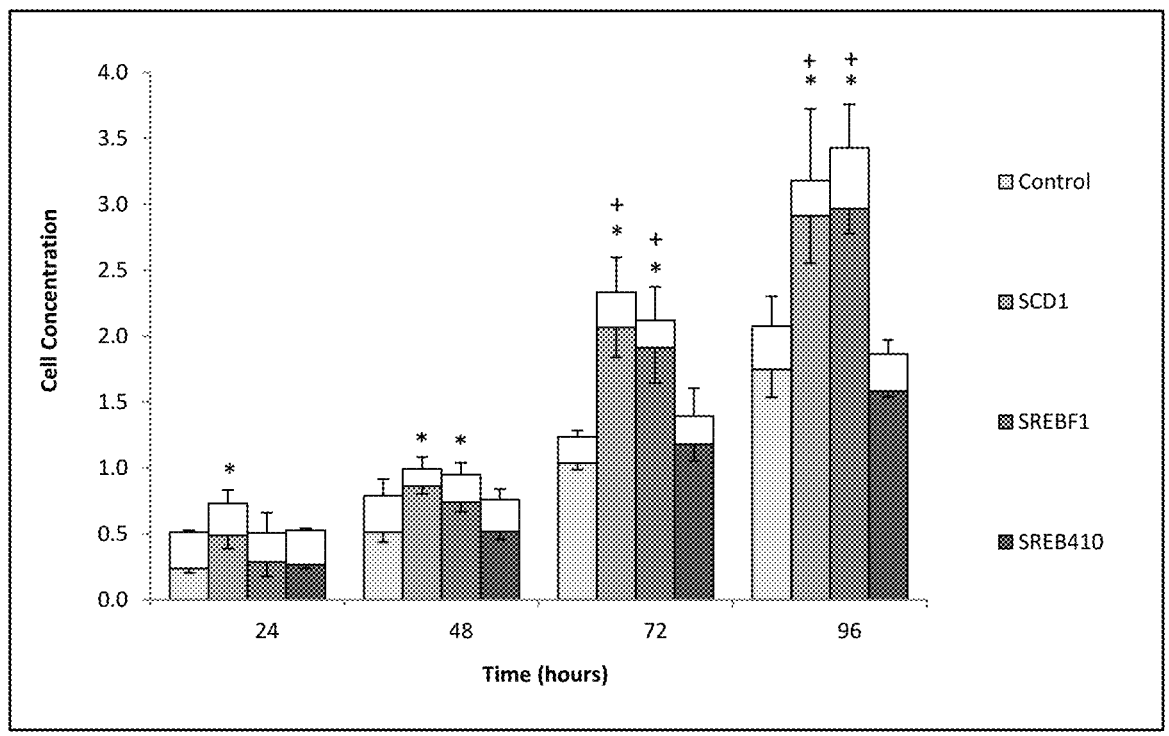
FIGS. 5A and 5B show the cell culture concentration and culture viability at 24, 48, 72, and 96 hours after transfection of control, SCD1-V5, SREBF1-V5 and SREBF410-V5 over-expressing CHOK1SV GS-KO cell pools with an eGFP containing plasmid.
Figure 5B:
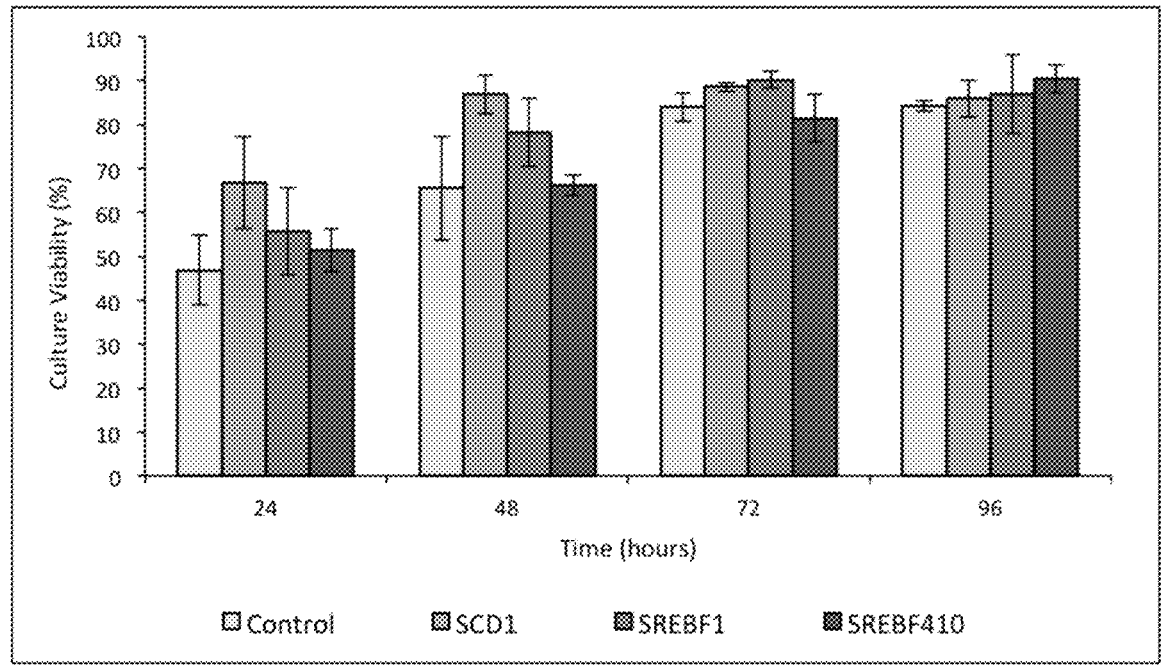

The results for the CHOK1SV GS-KO cells engineered to express SCD1, SREBF1, and SREBF410 are shown in FIGS. 5A and 5B. Viable cell concentration compared to total cell concentration are shown in FIG. 5A, with the viable cell concentration represented by the lower column, and the whole column representing the total number of cells counted. As shown in FIG. 5A, expression of LMM (SCD1 and SREBF1) results in a general increase in viable and total cell numbers across all time points. By 48, 72 and 96 hours, viable and total cell concentration were significantly higher in SCD1 and SREBF1-engineered cells. At 96 hours, viable cell counts for SCD1 and SREBF1-engineered cells were more than $1\times10^6$ cells/mL higher than control cells. Culture viability was also calculated and shown in FIG. 5B. The LMM-engineered cells generally showed an increase in culture viability as compared to control cells.

Example 4: Increased eGFP Induced Fluorescence in Stable Cells Overexpressing a LMM In this example, the production capacity for producing a recombinant protein was assessed in the CHO-Flp-In™ and the CHOK1SV GS-KO cell lines that were engineered to stably express LMMs, as described in Example 1. The LMM-engineered cells were transfected with an eGFP encoding expression vector as described in Example 3, and production capacity was assessed by measuring the amount of eGFP produced by flow cytometry at 24, 48, 72, and 96 hours after transfection. A FACSCalibur (BD Biosciences) instrument was used to measure the eGFP-mediated fluorescence of the cells and generate the data shown here.

Figure 6A:
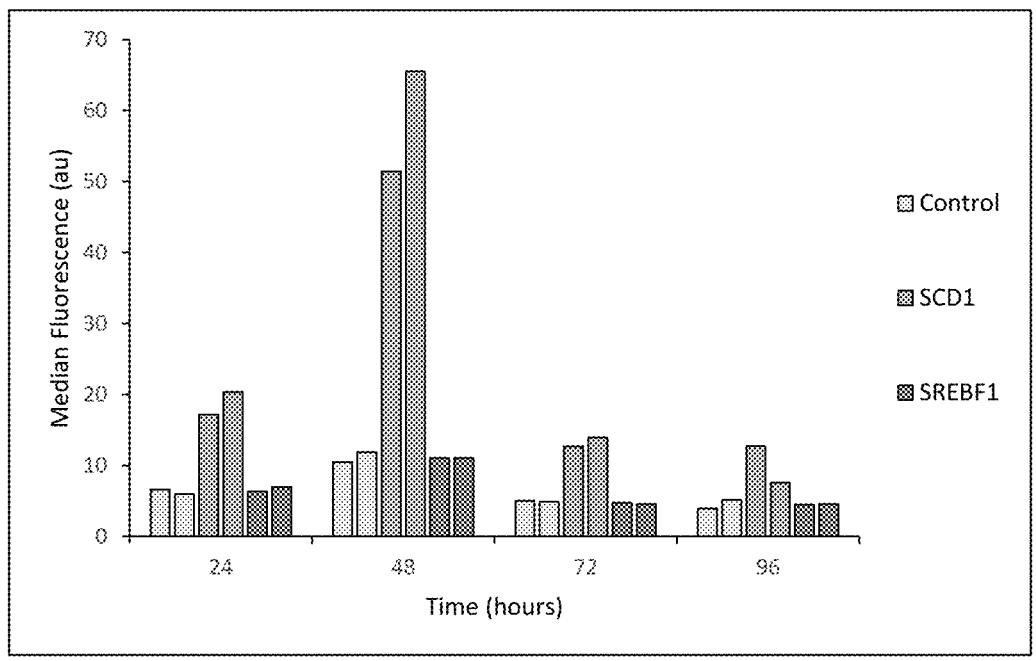
FIGS. 6A, 6B and 6C show flow cytometry generated data using a FACSCalibur instrument (BD Biosciences). Median (FIG. 6A), geometric mean (FIG. 6B) and arithmetic mean (FIG. 6C) values were acquired at 24, 48, 72 and 96 hours post transfection with an eGFP containing plasmid where samples were taken from control, SCD1-V5 or SREBF1-V5 overexpressing Flp-In CHO cell pools (n=2).
Figure 6B:
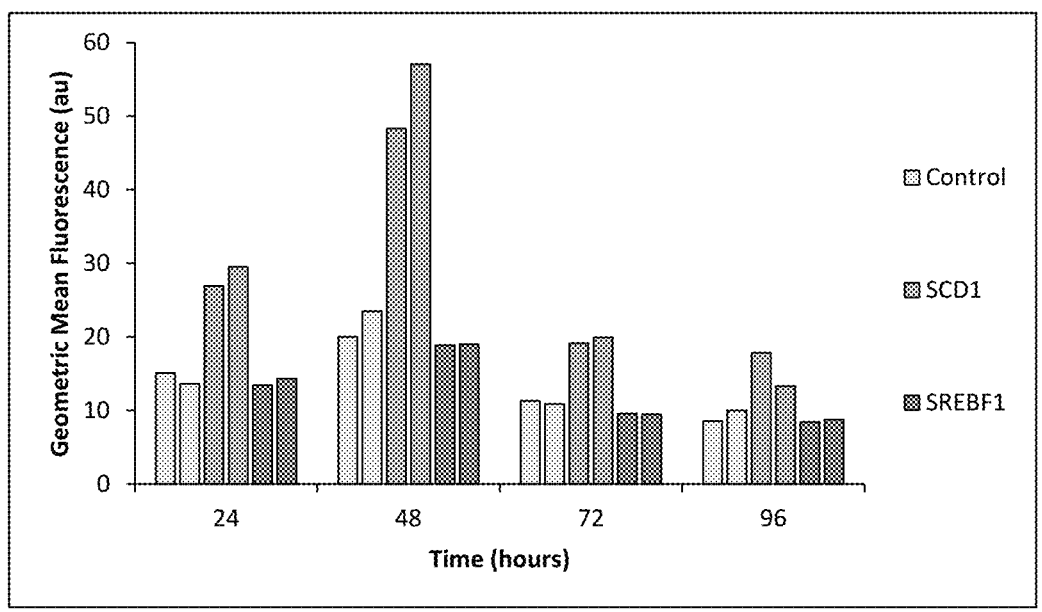
Figure 6C:
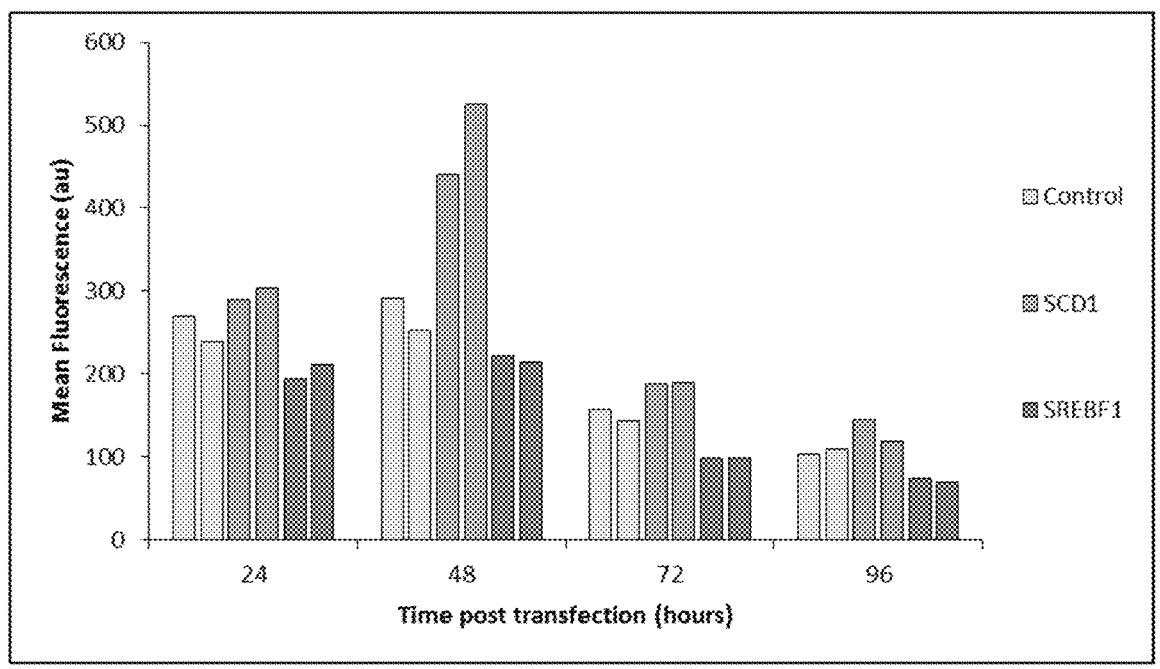

Production of eGFP was measured in Flp-In cells engineered to express V5-tagged SCD1 and SREBF1. FIGS. 6A, 6B, and 6C show the median fluorescence, the geometric mean fluorescence, and the arithmetic mean fluorescence, respectively, of the LMM-engineered Flp-In cells recorded using flow cytometry at the specified time points. These values are increased in SCD1 overexpressing cells for median fluorescence, geometric mean fluorescence, and arithmetic mean fluorescence, thereby demonstrating that cells stably expressing SCD1 are capable of producing more eGFP compared to the control cells.

Figure 7A:
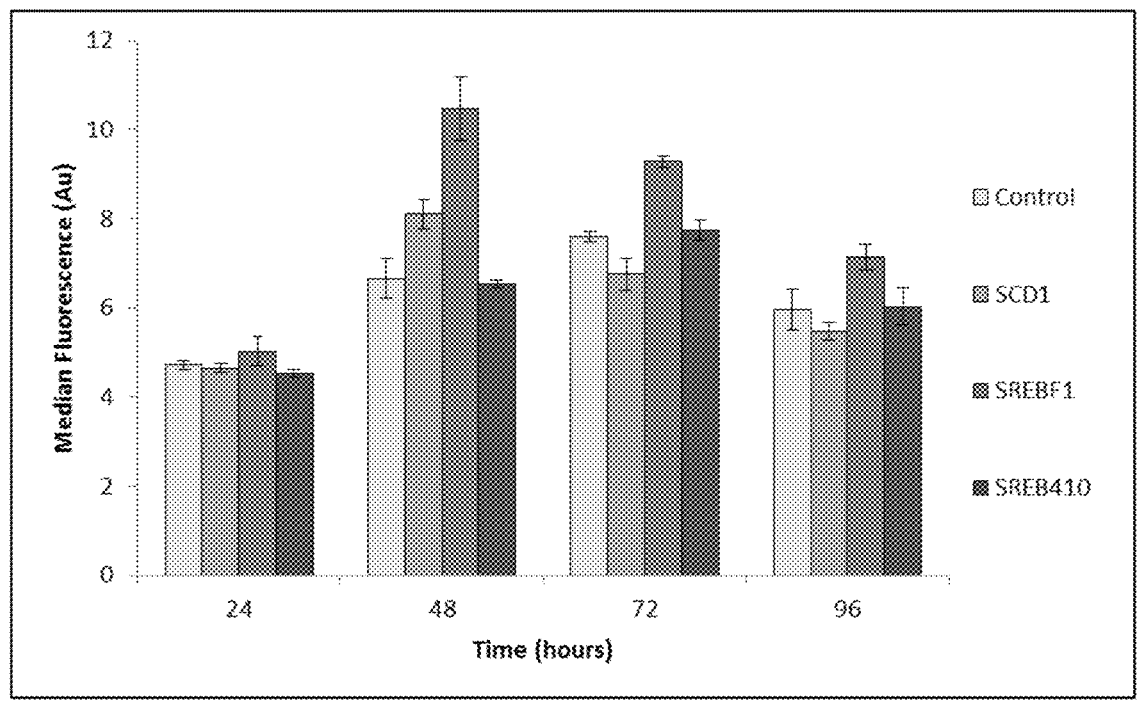
FIGS. 7A, 7B and 7C show flow cytometry generated data using a FACSCalibur instrument (BD Biosciences). Median (FIG. 7A), geometric mean (FIG. 7B) values were acquired at 24, 48, 72 and 96 hours post transfection with an eGFP containing plasmid where samples were taken from control, SCD1-V5, SREBF1-V5 or SREBF410-V5 overexpressing CHOK1SV GS-KO derived cells.
Figure 7B:
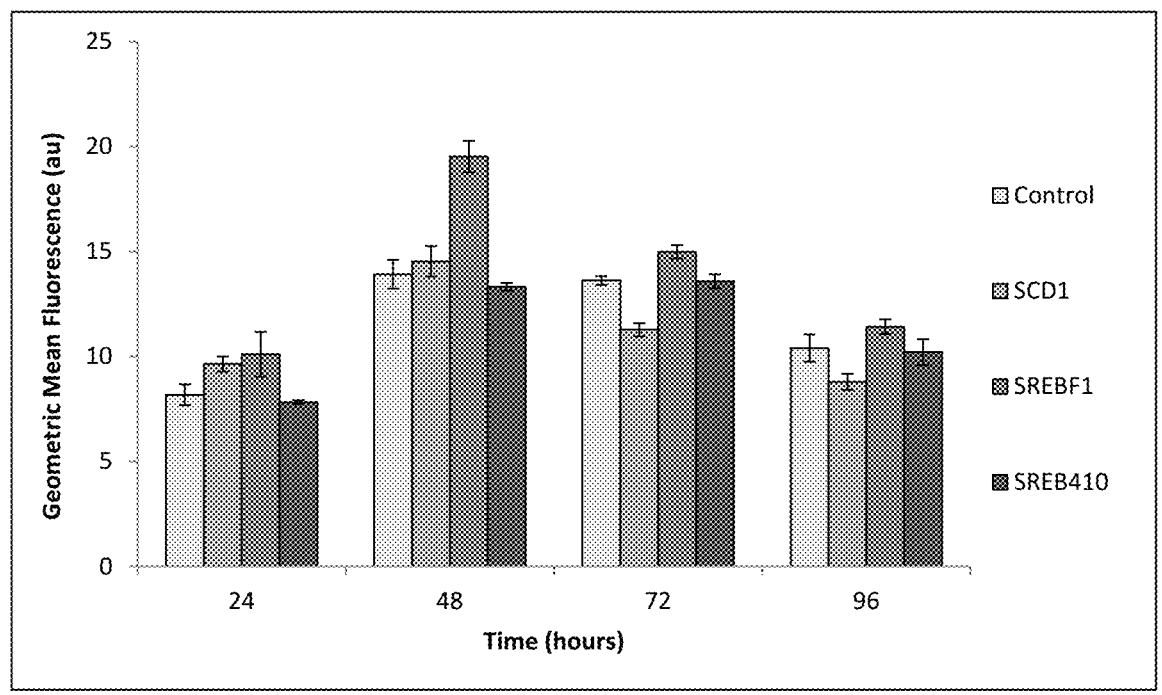

Production of eGFP was measured in CHOK1SV GS-KO cells engineered to express V5-tagged SCD1, SREBF1, and SREBF410. Median fluorescence is shown in FIG. 7A and geometric mean fluorescence is shown in FIG. 7B. Increased median fluorescence and geometric mean fluorescence was observed for cells engineered to overexpress SREBF1.

Figure 7C:
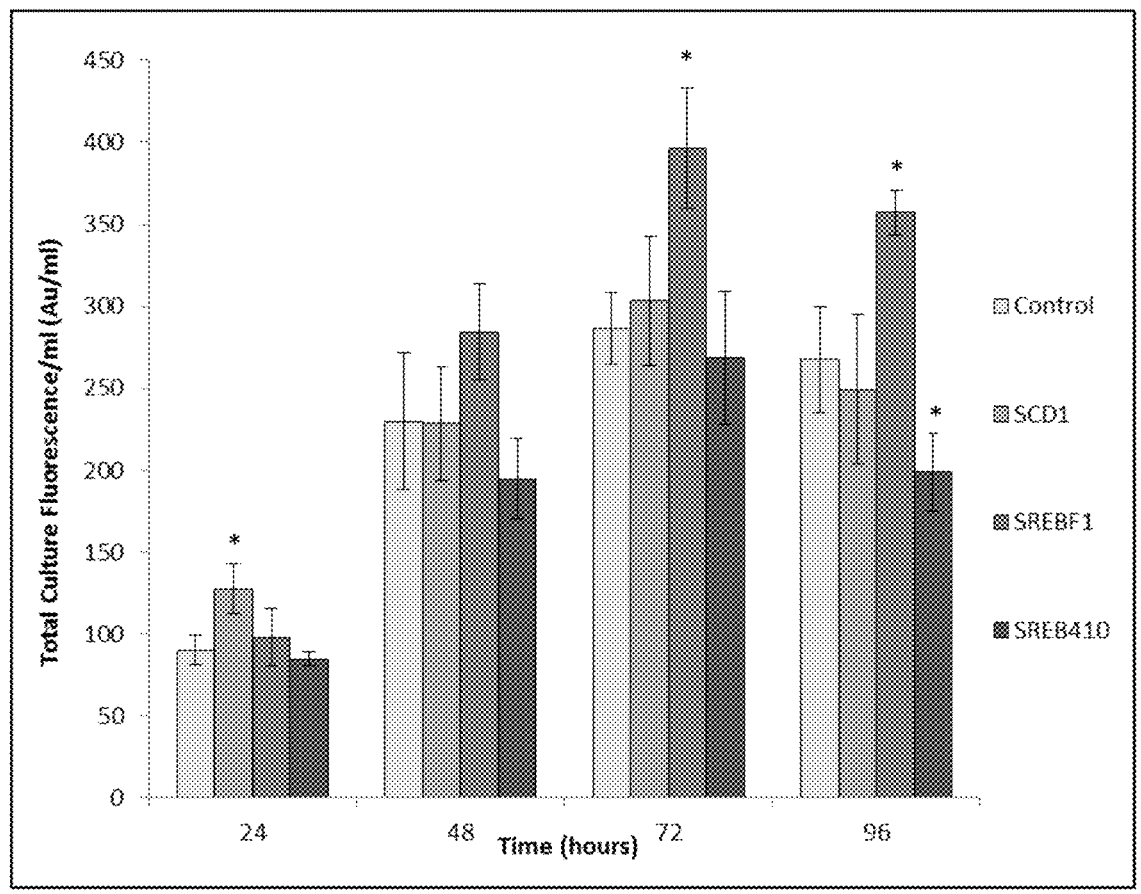

In order to account for differences in cell concentration and proliferation properties observed in CHOK1SV GS-KO derived cell lines. Total fluorescence per mL of culture was calculated by multiplying the measured arithmetic mean fluorescence by the total cell concentration ($\times10^6$ per mL), and the calculated values are shown in FIG. 7C. As shown in FIG. 7C, SCD1 overexpressing cells produced a significantly increased amount of recombinant protein (eGFP) at 24 hours after transfection as compared to control cells. SREBF1 overexpressing cells generally produced an increased amount of eGFP at all time points tested as compared to control cells, and significantly increased amounts at 72 and 96 hours after transfection.

Collectively, these data show that engineering cells to express an LMM, such as SCD1 and SREBF1, increases production capacity of a transiently expressed recombinant protein such as eGFP. Furthermore, as demonstrated by the fluorescence measured, the cells produced increased correctly folded and functional eGFP as compared to cells that did not have a modification that modulates lipid metabolism, thereby demonstrating that modulation of lipid metabolism increases both production yields and quality.

Example 5: Improved Productivity in Stable Cells Overexpressing an LMM

Similar to the experiments described in Example 4, cell lines that stably express LMMs were assessed for production capacity of different products, such as a model IgG4 antibody molecule (referred to herein as antibody A) and a fusion protein (referred to herein as Fc fusion protein or FP).

Figure 8A:
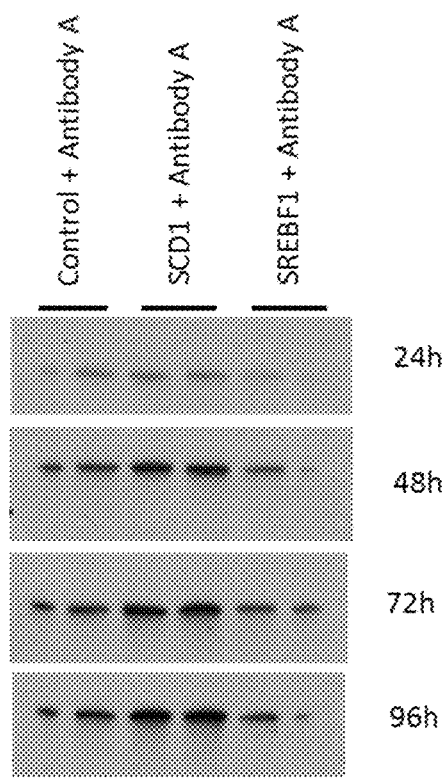
FIGS. 8A and 8B show antibody A production in CHO Flp-In cells stably overexpressing SCD1-V5 and SREBF1-V5 after transient transfection of a nucleic acid construct encoding antibody A heavy and light chains.
Figure 8B:
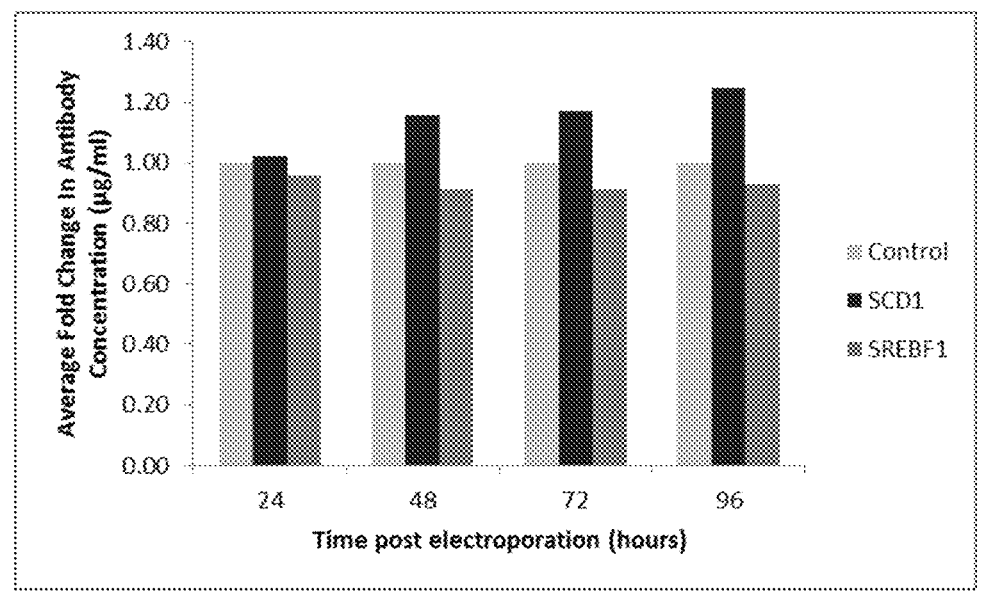
Figure 9A:
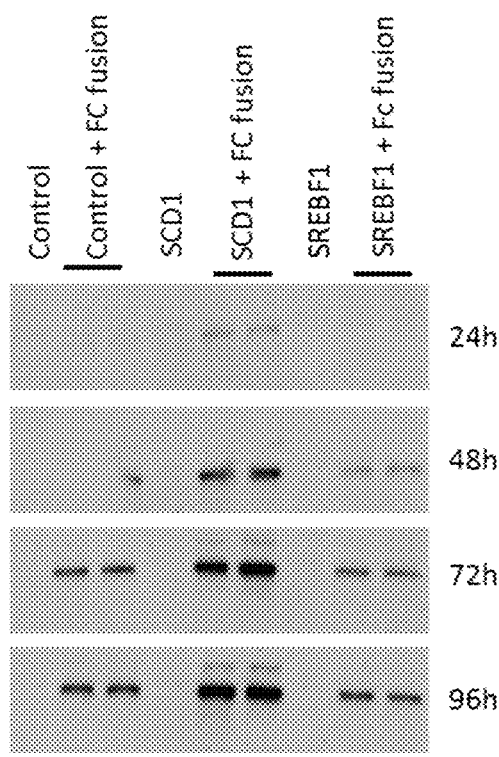
FIGS. 9A and 9B show the production of an Fc fusion protein in CHO Flp-In cell pools stably overexpressing SCD1-V5 and SREBF1-V5 after transient transfection of a nucleic acid construct encoding the fusion protein.
Figure 9B:
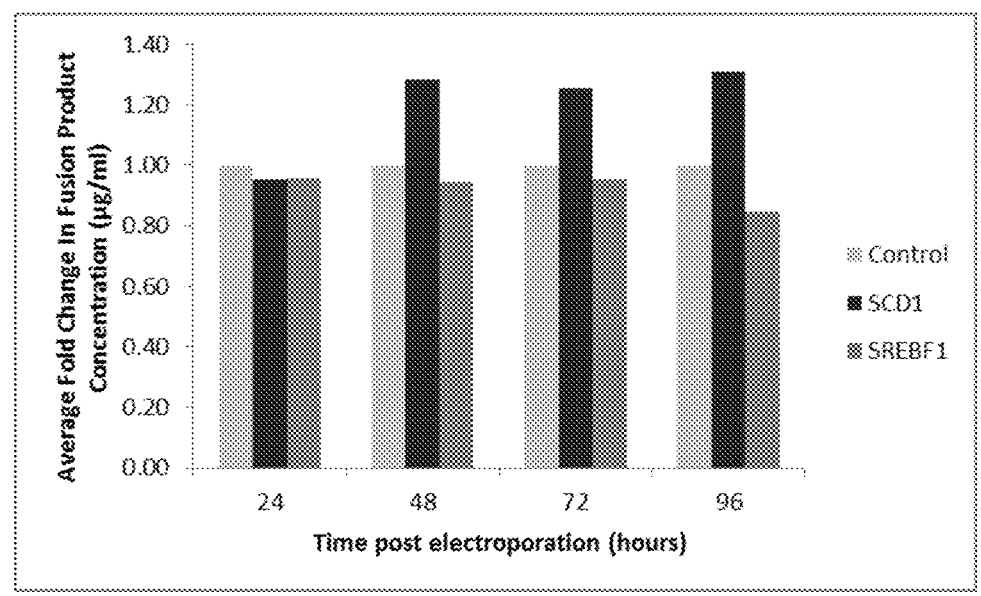

Flp-In cells stably expressing V5-tagged SCD1 and SREBF1 (engineered as described in Example 1) were electroporated with expression vectors encoding antibody A or a Fc fusion protein. Following electroporation, the quantity of recombinant antibody A and FP in culture supernatant was determined at 24, 48, 72, and 96 hours after electroporation by western blotting. An anti-heavy chain primary antibody, an anti-rabbit-HRP conjugated secondary antibody, and the appropriate detection reagent were used to detect antibody A (FIG. 8A) and the Fc fusion protein (FIG. 9A). Average fold change in production of the antibody A and Fc fusion protein was determined by Protein A HPLC, and shown in FIGS. 8B and 9B, respectively. Cell lines expressing exogenous SCD1 demonstrated increased productivity compared to the control cell lines with both recombinant proteins. Furthermore, this effect was consistent across the 24, 48, 72, and 96 hour time points analyzed.

Figure 10A:
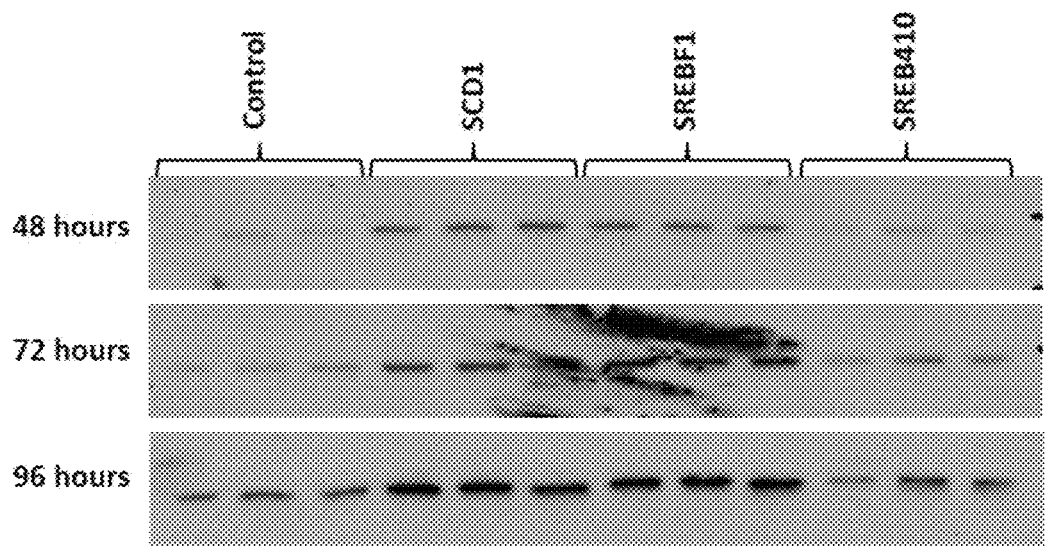
FIGS. 10A and 10B show the production of a well expressed antibody A in CHO GSKO cell pools stably overexpressing SCD1-V5, SREBF1-V5 and SREBF410-V5 after transient transfection of a nucleic acid construct encoding antibody A heavy and light chains at 48, 72 and 96 h post transfection and in a control, Null CHOK1SV GS-KO cell pool (a control pool of cells generated using an empty plasmid to express selection GS gene only, no LMM agents).
Figure 10B:
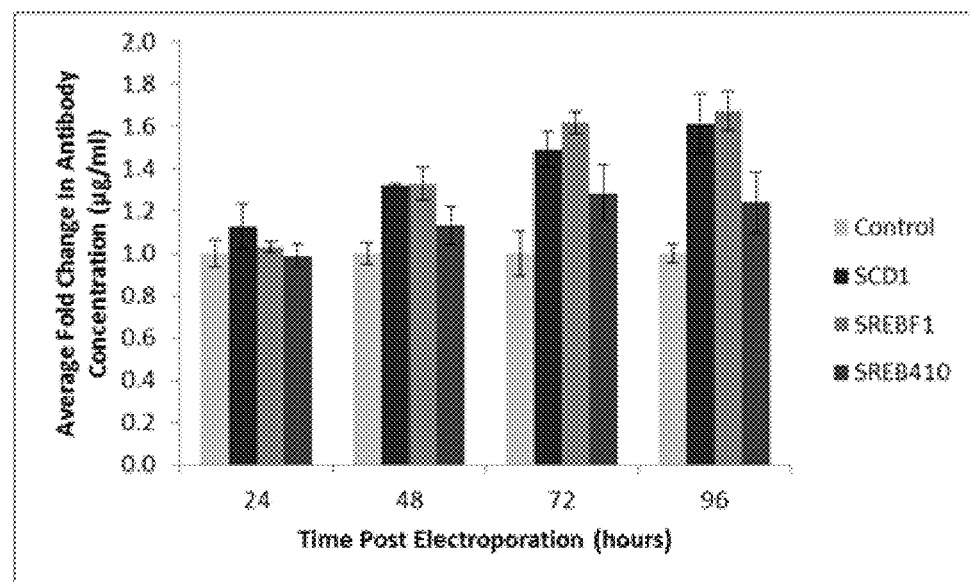
Figure 11A:
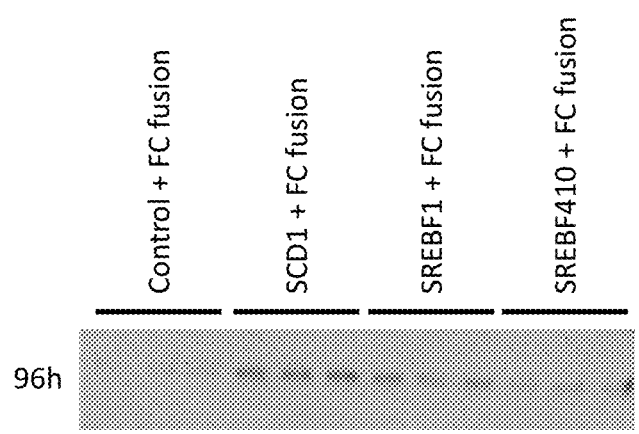
FIGS. 11A and 11B shows the relative production of a difficult to express Fc fusion protein in CHOK1SV GS-KO cell pools stably overexpressing SCD1-V5 and SREBF1-V5 or in a control cell pool after transient transfection of a nucleic acid construct encoding the Fc fusion protein.
Figure 11B:
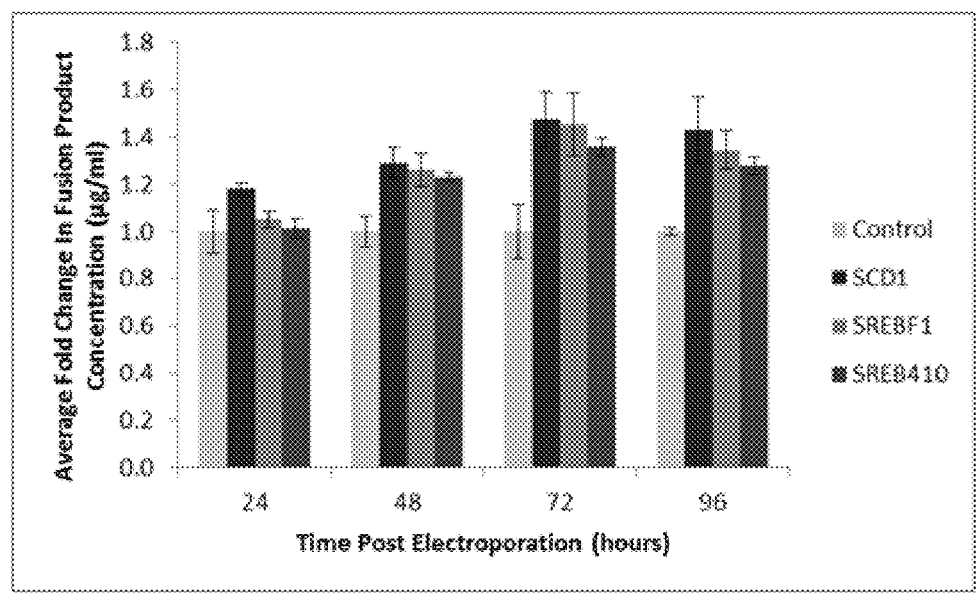

Lonza's CHOK1SV GS-KO (Xceed™) cells stably expressing the SCD1, SREBF1, and SREBF410 constructs (engineered as described in Example 1) were transiently transfected with two recombinant proteins; a model IgG4 (antibody A) and an Fc fusion protein. Following electroporation, the quantity of recombinant antibody A and FP in culture supernatant was determined every 24 hours up to 96 hours by western blotting using an anti-heavy chain primary antibody, an anti-rabbit-HRP conjugated secondary antibody, and the appropriate detection reagent (FIGS. 10A and 11A). Average fold change in production of the antibody A and Fc fusion protein was determined by Protein A HPLC, and shown in FIGS. 10B and 11B, respectively. CHOK1SV GS-KO cells lines expressing exogenous SCD1, SREBF1, and SREBF410 demonstrated increased productivity compared to the control cell lines with both recombinant proteins (FIGS. 10B and 11B). Furthermore, this effect was consistent across the 48, 72, and 96 hour time points analyzed.

Lonza's CHOK1SV GS-KO (Xceed™) cells stably expressing the SCD1, SREBF1, and SREBF410 constructs (engineered as described in Example 1) were stably transfected with two recombinant proteins; a model IgG4 (antibody A) and an Fc fusion protein. FIGS. 15A and 16A show volumetric productivity of antibody A and FC fusion protein respectively at 48, 96, 144 and 192 hours after initial seeding at $0.2 \times 10^6$ viable cells/ml. Results show that the SCD1 overexpressing cell pools improve the absolute yield of both recombinant molecules. Furthermore, upon calculations to include cell numbers, the specific productivity of both recombinant molecules was also greatly increased in SCD1 overexpressing cell pools (FIGS. 15B and 16B).

These results collectively show that engineering cells to express an LMM, such as SCD1, SREBF1, and a functional fragment of SREBF1 (SREBF410) increases production capacity of transiently expressed recombinant proteins, such as antibody molecules and fusion proteins.

Example 6: Improving Established Production Cell Lines

Examples 4 and 5 demonstrate that cell lines stably expressing LMMs have improved production when transiently expressing a recombinant product, such as a GFP, an antibody molecule, or a fusion protein. In this example, analysis was performed to determine the effect of LMMs on the enhancing existing stable yields of a recombinant product in established cell lines.

Figure 12A:
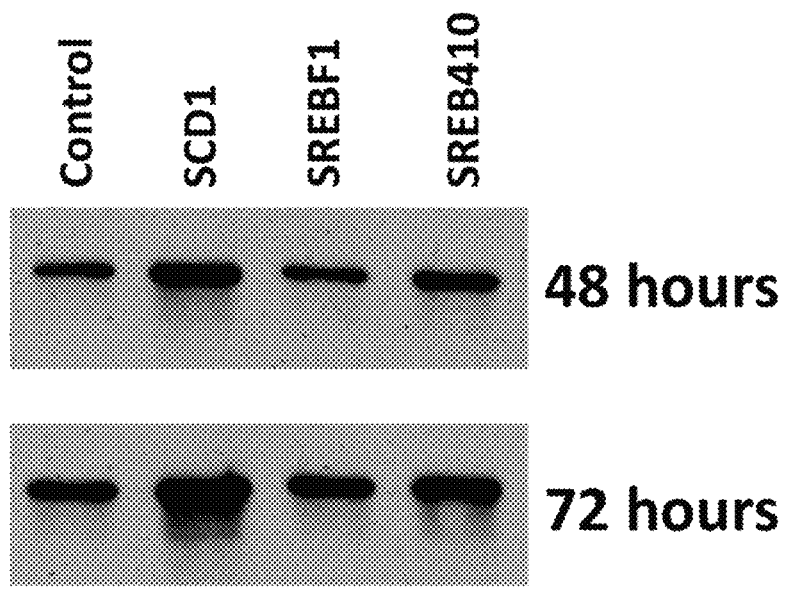
FIGS. 12A and 12B show the analysis of antibody A production from supernatant harvested after 48 and 72 hours from a CHO cell line stably expressing antibody A which have been transiently transfected with plasmid constructs containing either control (empty), SCD1-V5, SREBF1-V5 or SREBF410-V5 genes.
Figure 12B:
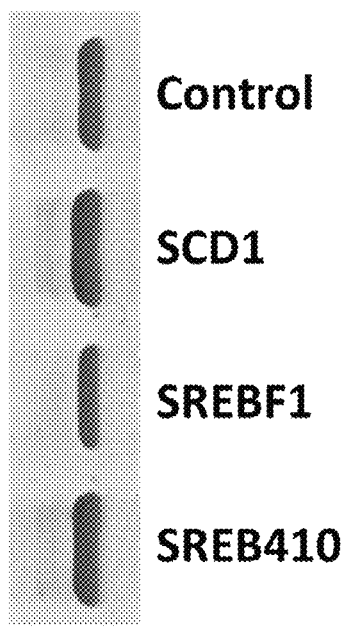
Figure 13:
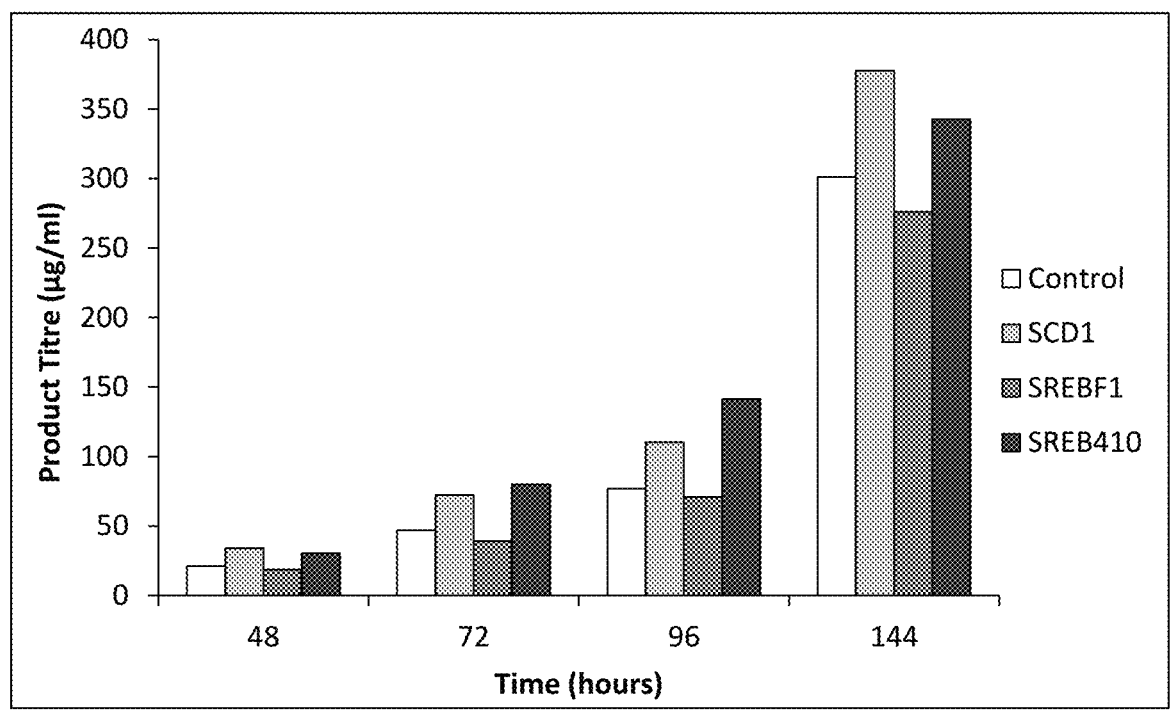
FIG. 13 shows analysis of antibody A production from supernatant harvested after 48, 72, 96 and 144 hours from a CHO cell line stably expressing antibody A which had been transiently transfected with plasmid constructs containing either control (empty), SCD1-V5, SREBF1-V5 or SREBF410-V5 genes where protein A Octet analysis was used to determine volumetric antibody concentration (n=2).
Figure 14:
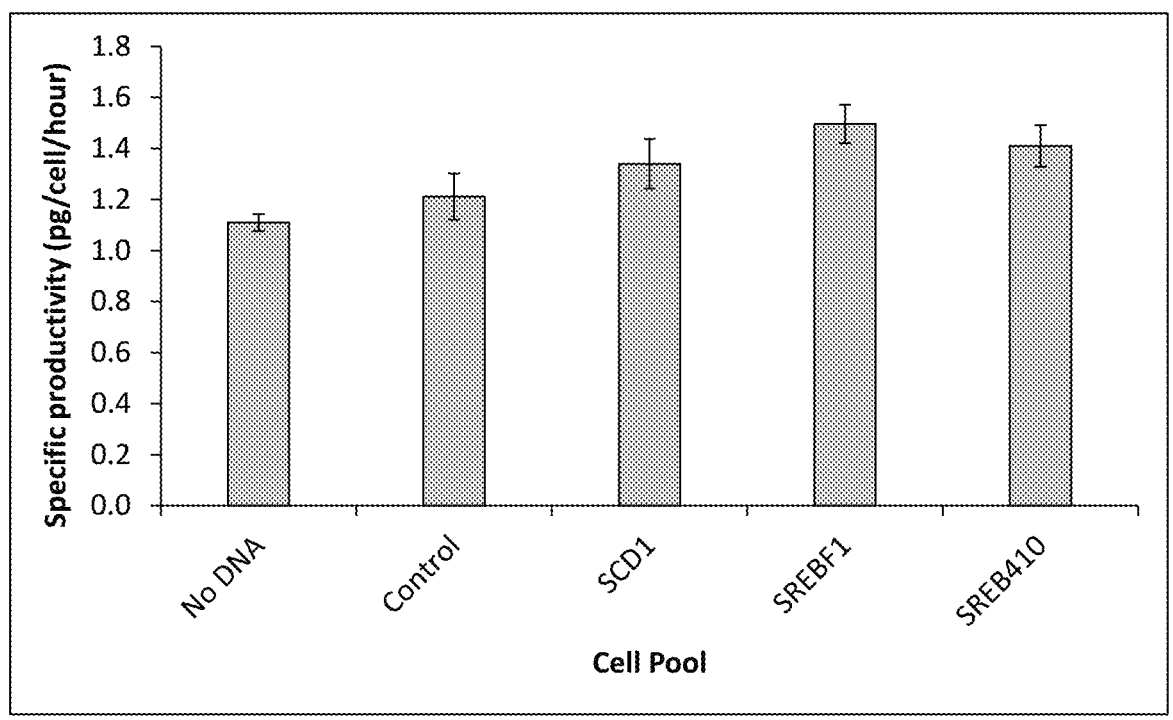
FIG. 14 shows analysis of an FC fusion protein from supernatant samples harvested after 48, 72, 96 and 144 hours from a CHO cell line stably expressing antibody A which had been transiently transfected with plasmid constructs containing either control (empty), SCD1-V5, SREBF1-V5 or SREBF410-V5 genes where viable cell number and protein A titre measurements were used to determine specific productivity of the FC fusion protein Error bars show standard deviation (n=3).

CHO121 cells that have been previously engineered to stably express a model IgG4 antibody molecule (antibody A) were used. Constructs encoding V5-tagged SCD1, SREBF1 and a truncated SREBF1 (SREBF410) were transiently expressed in the antibody A-stably expressing cells. Control cells were transfected with an empty V5 tag vector. Supernatants from the cells were harvested at 48, 72, and 168 hours. Western blot analysis was performed to determine the amount of antibody A produced by using an anti-heavy chain primary antibody (Sigma 19764), followed by anti-rabbit HRP conjugated secondary antibody (Sigma A6154), and the results are shown in FIG. 12A. As shown, expression of LMMs SCD1 and SREBF410 resulted in an increase in the amount of antibody A produced by the cells as compared to control at both 48 and 72 hours after introduction of the LMMs. Supernatants from cells were subjected to Coomassie analysis to show the amount of antibody A produced after 168 hours after introduction of the LMMs, and demonstrate that LMM transient expression (SCD1 and SREBF410) resulted in improved production of the recombinant protein (FIG. 12B). FIG. 13 shows quantitative analysis of antibody A using protein A HPLC highlighting a marked increase in the average product titre following transient transfections with SCD1 and SREB410 containing plasmids at 48, 72, 96 and 144 hours post transfection. FIG. 14 shows quantitative analysis of the FC fusion protein using protein A analysis to determine product titres and viable cell numbers to determine specific productivity. This data shows an increase in the average specific productivity of cells transiently transfected with vectors containing LMM elements and the SREBF1 containing construct yields the highest average value.

These results show that modulation of the lipid metabolism in established cell lines can further improve production capacity compared to established yields.

Example 7: Improved Productivity by Simultaneous Introduction of Recombinant Genes and LMMs Plasmids/constructs were generated which comprise of genes for appropriate expression of both an exemplary immunocytokine and either a control (no LMM), SCD1, SREBF1 or SREB411 (SREBF1 derived sequences were CHO specific; NM 001244003, SEQ ID NOs: 34 and 36). These constructs were then used to transiently transfect Lonza's CHOK1SV GS-KO cells. FIG. 17A shows western analysis of supernatants harvested at 48 and 96 hours post transfection. The supernatant samples used were reduced and the transient product was detected by probing with an anti-heavy chain primary antibody and HRP conjugated anti-rabbit secondary to highlight a native heavy chain (lower band) and cytokine fused heavy chain (upper band). Inclusion of SCD1, SREBF1 and SREB411 genes in the transfected construct resulted in an increase in both band intensities at both 48 and 96 hours post transfection. Furthermore, FIG. 17B shows quantitative analysis of samples obtained at 96 hours post transfection using protein A analysis. Relative abundances of the immunocytokine support the data presented in western analysis (FIG. 17A).

These data show that the simultaneous inclusion of an LMM, such as SCD1, SREBF1, and a functional fragment of SREBF1 (SREBF411), with recombinant product genes can improve production capacity.

What is claimed is:

1. A cell comprising:
    a first exogenous nucleic acid encoding a first lipid metabolism modulator (LMM), wherein the first LMM comprises a sterol regulatory element-binding transcription factor 1 (SREBF1) or a functional fragment or isoform thereof; and
    an exogenous nucleic acid encoding a recombinant polypeptide,
    wherein the first exogenous nucleic acid is integrated into the chromosomal genome of the cell; and
    wherein the cell is a CHO-derived cell.

2. The cell of claim 1, wherein the cell is selected from the group consisting of CHO-K1, CHOK1SV, Potelligent CHOK1SV (FUT8-KO), CHO GS-KO, Exceed (CHOK1SV GS-KO), CHO-S, CHO DG44, CHO DXB11, and CHOZN.

3. The cell of claim 1, wherein the first LMM modulates the expression of the recombinant polypeptide.

4. The cell of claim 3, wherein the first LMM alters the expression of a component involved in a lipid metabolism pathway.

5. The cell of claim 1, further comprising a second exogenous nucleic acid encoding a second LMM, wherein the second exogenous nucleic acid encoding a second LMM is integrated into the chromosomal genome of the cell.

6. The cell of claim 5, wherein the second LMM is selected from a transcription regulator that mediates the expression of a lipid metabolism gene product selected from SREBF2 (sterol regulatory element-binding transcription factor 2), PRMT5, FAS (fatty acid synthase), ACC (acetyl-coA carboxylase), ACL (ATP citrate lyase), DGAT (diglyceride acyltransferase), GPAT (glycerol 3-phosphate acyltransferase), LPL (lipoprotein lipase), AGPAT (1-actyl-sn-glycerol-3-phosphate O-acyltransferase), AGNPR (acyl/alkylglycerone-phosphate reductase), CCT (phosphocholine cytidyltransferase), CDS (phosphatidate cytidylyltransferase), CEPT (diacylglycerol choline/ethanolaminephosphotransferase), CERT (ceramide transfer protein), CGT (N-acylsphingosine galactosyltransferase), CPT (diacylglycerol cholinephosphotransferase), CLS (cardiolipin synthase), CRD (ceramidase), GNPAT (glycerone-phosphate O-acyltransferase), KDSR (3-ketosphinganine reductase), LCS (polypeptide N-acetylgalactosaminyltransferase), PAP (phosphatidic acid phosphatase), PEMT (phosphatidylethanolamine N-methyltransferase), PGP (phosphatidylglycerophosphatase), PGS (CDP-diacylglycerol-glycerol-3-phosphate 3-phosphatidyltransferase), PIS (CDP-diacylglycerol-inositol 3-phosphatidyltransferase), PSD (phosphatidylserine decarboxylase), PSS1 (phosphatidylserine synthase 1), PSS2 (phosphatidylserine synthase 2), SGMS (ceramide choline phosphotransferase), SNAT (sphingosine N-acyltransferase), SPK (sphinganine kinase), SPP (sphingosine-1-phosphate phosphatase), SPT (serine Co-palmitoyltransferase), PED (plasmanylethanolamine desaturase), S1P (site-1 protease), S2P (site-2 protease), SCAP (SREBF cleavage-activating protein), INSIG1 (insulin induced gene 1), INSIG2 (insulin induced gene 2), HMG CoA reductase (2-hydroxy-3-methylgulatryl-CoA reductase), a PPAR receptor, or a functional fragment or analog of any of the same.

7. The cell of claim 5, wherein the second LMM is selected from: SCD1 (stearoyl CoA desaturase-1), SCD2 (stearoyl CoA desaturase-2), SCD3 (stearoyl CoA desaturase-3), SCD4 (stearoyl CoA desaturase-4), SCD5 (Steoryl CoA desaturase-5).

* * * * *